(12) United States Patent
Ohtomo et al.

(10) Patent No.: US 10,782,300 B2
(45) Date of Patent: Sep. 22, 2020

(54) GPC3-TARGETING DRUG WHICH IS ADMINISTERED TO PATIENT RESPONSIVE TO GPC3-TARGETING DRUG THERAPY

(71) Applicants: CHUGAI SEIYAKU KABUSHIKI KAISHA, Tokyo (JP); F. Hoffmann-La Roche AG, Basel (CH)

(72) Inventors: Toshihiko Ohtomo, Tokyo (JP); Ya-Chi Chen, New York City, NY (US); Jun Amano, Shizuoka (JP); Mikiko Nakamura, Tokyo (JP)

(73) Assignees: CHUGAI SEIYAKU KABUSHIKI KAISHA, Kita-ku, Tokyo (JP); F. Hoffmann-La Roche AG, Basel (CH)

( * ) Notice: Subject to any disclaimer, the term of this patent is extended or adjusted under 35 U.S.C. 154(b) by 0 days.

(21) Appl. No.: 14/441,551

(22) PCT Filed: Dec. 24, 2013

(86) PCT No.: PCT/JP2013/007529
§ 371 (c)(1),
(2) Date: May 8, 2015

(87) PCT Pub. No.: WO2014/097648
PCT Pub. Date: Jun. 26, 2014

(65) Prior Publication Data
US 2015/0285806 A1   Oct. 8, 2015

(30) Foreign Application Priority Data
Dec. 21, 2012   (JP) .................. 2012-280304

(51) Int. Cl.
| | | |
|---|---|---|
| G01N 33/574 | (2006.01) | |
| C07K 16/30 | (2006.01) | |
| C07K 16/28 | (2006.01) | |
| A61K 39/00 | (2006.01) | |

(52) U.S. Cl.
CPC ....... *G01N 33/57438* (2013.01); *C07K 16/28* (2013.01); *C07K 16/303* (2013.01); *A61K 2039/505* (2013.01); *A61K 2039/54* (2013.01); *A61K 2039/545* (2013.01); *C07K 2317/34* (2013.01); *C07K 2317/73* (2013.01); *G01N 2333/4722* (2013.01); *G01N 2400/00* (2013.01); *G01N 2800/52* (2013.01)

(58) Field of Classification Search
CPC ..... G01N 33/57438; G01N 2333/4722; G01N 2800/52
See application file for complete search history.

(56) References Cited

U.S. PATENT DOCUMENTS

| | | | |
|---|---|---|---|
| 5,322,678 A | | 6/1994 | Morgan, Jr. et al. |
| 6,436,411 B1 * | | 8/2002 | Riordan ............... A61K 38/191 424/278.1 |
| 6,617,156 B1 | | 9/2003 | Doucette-Stamm et al. |
| 6,737,056 B1 | | 5/2004 | Presta |
| 7,297,775 B2 | | 11/2007 | Idusogie et al. |
| 7,317,091 B2 | | 1/2008 | Lazar et al. |
| 7,691,586 B2 * | | 4/2010 | Watanabe ........ G01N 33/57438 435/7.1 |
| 7,744,880 B2 | | 6/2010 | Aburatani et al. |
| 7,867,734 B2 | | 1/2011 | Nakano et al. |
| 7,871,613 B2 * | | 1/2011 | Kinoshita ............ C07K 16/303 424/130.1 |
| 7,919,086 B2 | | 4/2011 | Nakano et al. |
| 8,263,077 B2 | | 9/2012 | Aburatani et al. |
| 8,497,355 B2 | | 7/2013 | Igawa et al. |
| 8,663,929 B2 | | 3/2014 | Kataoka et al. |
| 8,937,158 B2 | | 1/2015 | Lazar et al. |
| 9,096,651 B2 | | 8/2015 | Igawa et al. |
| 9,102,739 B2 | | 8/2015 | Lazar et al. |
| 9,513,292 B2 | | 12/2016 | Aburatani et al. |
| 2002/0102254 A1 | | 8/2002 | Leung et al. |
| 2004/0110226 A1 | | 6/2004 | Lazar et al. |
| 2004/0228856 A1 | | 11/2004 | Presta |
| 2004/0236080 A1 | | 11/2004 | Aburatani et al. |
| 2005/0054832 A1 | | 3/2005 | Lazar et al. |
| 2005/0171339 A1 | | 8/2005 | Sugo et al. |
| 2005/0233392 A1 | | 10/2005 | Filmus et al. |
| 2006/0014223 A1 | | 1/2006 | Aburatani et al. |
| 2006/0040325 A1 | | 2/2006 | Wu et al. |
| 2006/0167232 A1 | | 7/2006 | Aburatani et al. |
| 2006/0188510 A1 | | 8/2006 | Aburatani et al. |

(Continued)

FOREIGN PATENT DOCUMENTS

| | | |
|---|---|---|
| CA | 2451493 A1 | 1/2003 |
| CA | 2801911 A1 | 3/2004 |

(Continued)

OTHER PUBLICATIONS

ClinicalTrials.gov (NCT00746317 on Nov. 16, 2010).*

(Continued)

*Primary Examiner* — Karen A. Canella
(74) *Attorney, Agent, or Firm* — Sughrue Mion, PLLC

(57) ABSTRACT

The present invention discloses a method for determining the efficacy of GPC3-targeting drug therapy for cancer in a patient before the start of GPC3-targeting drug therapy or a patient or determining the continuation of GPC3-targeting drug therapy for a patient, including monitoring a concentration of free GPC3 in a biological sample isolated from the patient before the start of GPC3-targeting drug therapy and/or the patient treated with the GPC3-targeting drug therapy, wherein when the concentration of free GPC3 is a predetermined value, the efficacy of the GPC3-targeting drug therapy is determined or the continuation of the GPC3-targeting drug therapy is determined. The present invention also discloses a GPC3-targeting drug or a preparation which is to be further administered to a patient for which the efficacy of the GPC3-targeting drug therapy has been determined or the continuation of the GPC3-targeting drug therapy has been determined.

21 Claims, 20 Drawing Sheets
(1 of 20 Drawing Sheet(s) Filed in Color)
Specification includes a Sequence Listing.

(56) References Cited

U.S. PATENT DOCUMENTS

| | | |
|---|---|---|
| 2006/0246550 A1 | 11/2006 | Okumura |
| 2007/0087005 A1 | 4/2007 | Lazar et al. |
| 2007/0190599 A1 | 8/2007 | Nakano et al. |
| 2007/0269444 A1 | 11/2007 | Kinoshita et al. |
| 2008/0003623 A1 | 1/2008 | Nakajima et al. |
| 2008/0008710 A1 | 1/2008 | Aburatani et al. |
| 2008/0124330 A1 | 5/2008 | Nakano et al. |
| 2008/0138827 A1 | 6/2008 | Watanabe et al. |
| 2008/0166756 A1 | 7/2008 | Tsuchiya et al. |
| 2009/0060907 A1 | 3/2009 | Aburatani et al. |
| 2010/0167315 A1 | 7/2010 | Thibault et al. |
| 2010/0239577 A1* | 9/2010 | Igawa ............ C07K 16/303 424/133.1 |
| 2010/0248359 A1* | 9/2010 | Nakano ........... C07K 16/303 435/325 |
| 2011/0033452 A1 | 2/2011 | Nakano et al. |
| 2011/0091907 A1 | 4/2011 | Kataoka et al. |
| 2011/0104157 A1 | 5/2011 | Kinoshita et al. |
| 2015/0098941 A1 | 4/2015 | Lazar et al. |
| 2015/0210763 A1 | 7/2015 | Kuramochi et al. |
| 2015/0259417 A1 | 9/2015 | Nakano et al. |
| 2015/0285806 A1 | 10/2015 | Ohtomo et al. |
| 2015/0315278 A1 | 11/2015 | Igawa et al. |

FOREIGN PATENT DOCUMENTS

| | | |
|---|---|---|
| CN | 1678740 A | 10/2005 |
| CN | 101377506 A | 3/2009 |
| CN | 102027372 A | 4/2011 |
| CN | 102046200 A | 5/2011 |
| CN | 102276721 A | 12/2011 |
| EP | 0329185 A2 | 8/1989 |
| EP | 1411118 A1 | 4/2004 |
| EP | 1 541 686 A1 | 6/2005 |
| EP | 1 548 442 A1 | 6/2005 |
| EP | 1541680 A1 | 6/2005 |
| EP | 1674111 A1 | 6/2006 |
| EP | 1816140 A1 | 8/2007 |
| EP | 1829962 A1 | 9/2007 |
| EP | 1548442 B1 | 1/2011 |
| EP | 2647706 A1 | 10/2013 |
| EP | 2863224 A1 | 4/2015 |
| EP | 2 937 697 A1 | 10/2015 |
| JP | H02-28200 A | 1/1990 |
| JP | 2007-93274 A | 4/2007 |
| JP | 2007-300927 A | 11/2007 |
| JP | 2009232848 A | 10/2009 |
| JP | 201168682 A | 4/2011 |
| JP | 2015-511702 A | 4/2015 |
| RU | 2001124907 A | 6/2003 |
| WO | 200047228 A1 | 8/2000 |
| WO | 02/40545 A2 | 5/2002 |
| WO | 03000883 A1 | 1/2003 |
| WO | 2003/057881 A1 | 7/2003 |
| WO | 03100429 A2 | 12/2003 |
| WO | 2004/022739 A1 | 3/2004 |
| WO | 2004022597 A1 | 3/2004 |
| WO | 2004022754 A1 | 3/2004 |
| WO | 2004023145 A1 | 3/2004 |
| WO | 2004/029207 A2 | 4/2004 |
| WO | 2004038420 A1 | 5/2004 |
| WO | 2004099249 A2 | 11/2004 |
| WO | 2005023301 A1 | 3/2005 |
| WO | 2005106485 A1 | 11/2005 |
| WO | 2006006693 A1 | 1/2006 |
| WO | 2006038588 A1 | 4/2006 |
| WO | 2006046751 A1 | 5/2006 |
| WO | 2006/067913 A1 | 6/2006 |
| WO | 2007/005612 A2 | 1/2007 |
| WO | 2007047291 A2 | 4/2007 |
| WO | 2007/059782 A1 | 5/2007 |
| WO | 2007081790 A2 | 7/2007 |
| WO | 2007137170 A2 | 11/2007 |
| WO | 2008/032217 A2 | 3/2008 |
| WO | 2009041062 A1 | 4/2009 |
| WO | 2009116659 A1 | 9/2009 |
| WO | 2009122667 A1 | 10/2009 |
| WO | 2012/145469 A1 | 10/2012 |
| WO | 2013070468 A1 | 5/2013 |
| WO | 2013/118858 A1 | 8/2013 |
| WO | 2013/127465 A1 | 9/2013 |
| WO | 2013181543 A1 | 12/2013 |

OTHER PUBLICATIONS

Office Action dated Jan. 4, 2016 from the State Intellectual Property Office of the P.R. China issued in corresponding Application No. 201380067139.1.

Notice of Allowance dated Jan. 4, 2016 from the Korean Intellectual Property Office issued in corresponding Application No. 10-2010-7008895.

Kawaida et al., "Clinicopathological significance of the expression of Glypican-3 in hepatocellular carcinoma", Proceeding of the Japanese Society of Pathology, 104th conference of the Japanese Society of Pathology-Nagoya Congress Center, Mar. 23, 2015, vol. 104, No. 1, p. 324 (total 4 pages).

Ikeda et al., "Japanese phase I study of GC33, a humanized antibody against glypican-3 for advanced hepatocellular carcinoma", Cancer Science, Apr. 2014, vol. 105, No. 4, pp. 455-462.

Endo, "A novel molecular targeted therapy, humanized anti-glypican 3 antibody (GC33), for the treatment of unresectable hepatocellular cancer", Medical Science Digest, Aug. 2013, vol. 39, No. 9, pp. 440-443 (total 10 pages).

Hashiguchi et al., "Using immunofluorescent digital slide technology to quantify protein expression in archival paraffin-embedded tissue sections", Pathology International, 2010, vol. 60, pp. 720-725.

International Search Report dated Sep. 20, 2016, issued by the International Searching Authority in application No. PCT/JP2016/069493.

Office Action dated Mar. 28, 2016 from the United States Patent and Trademark Office issued in U.S. Appl. No. 14/629,967.

Office Action dated Mar. 30, 2016 from the United States Patent and Trademark Office issued in U.S. Appl. No. 12/584,728.

Konno et al., "Fucose content of monoclonal antibodies can be controlled by culture medium osmolality for high antibody-dependent cellular cytotoxicity", Cytotechnology (2012) 64 pp. 249-265.

Kunkel et al., "Comparisons of the Glycosylation of a Monoclonal Antibody Produced under Nominally Identical Cell Culture Conditions in Two Different Bioreactors", Biotechnol. Prog. 2000, 16, pp. 462-470.

Raju, "Glycosylation Variations with Expression Systems and Their Impact on Biological Activity of Therapeutic Immunoglobulins", BioProcess International, Apr. 2003, pp. 44-53 ( 8 pages total).

Summons to Oral Proceedings dated Mar. 4, 2016 from the European Patent Office issued in corresponding Application No. 05800031.6.

Communication dated Mar. 4, 2016 from the European Patent Office issued in corresponding Application No. 12179554.6.

Communication dated Jun. 8, 2016 from U.S. Patent & Trademark Office in counterpart U.S. Appl. No. 10/526,741.

Communication dated Jun. 22, 2016, from the European Patent Office in counterpart European application No. 15153329.6.

Capurro et al.,"Glypican-3: A Novel Serum and Histochemical Marker for Hepatocellular Carcinoma", Gastroenterology, 2003, vol. 125, pp. 89-97.

Sung et al.,"Glypican-3 is overexpressed in human hepatocellular carcinoma", Cancer Sci, Mar. 2003, vol. 94, No. 3, pp. 259-262.

Lage et al., "Expression of a glypican-related 62-kDa antigen is decreased in hepatocellular carcinoma in correspondence to the grade of tumor differentiation", Virchows Arch, (2001) vol. 438, pp. 567-573.

Midorikawa et al., "Glypican-3, overexpressed in hepatocellular carcinoma, modulates FGF2 and BMP-7 signaling", International Journal of Cancer, 2003, vol. 103, pp. 455-465.

(56) References Cited

OTHER PUBLICATIONS

Portolano et al., "Lack of Promiscuity in Autoantigen-Specific H and L Chain Combinations as Revealed by Human H and L Chain 'Roulette'", The Journal of Immunology, 1993, vol. 150, No. 3, pp. 880-887.
Communication dated Jun. 10, 2016, from the European Patent Office in counterpart European Application No. 13864465.3.
Mitchell Ho et al. "Glypican-3: A new target for cancer immunotherapy", European Journal of Cancer, Pergamon, GB, vol. 47, No. 3, Oct. 27, 2010, pp. 333-338 (total 1 page).
Communication dated Feb. 5, 2016 from the Ecuadorian Intellectual Property Office in counterpart application No. 2016-007.
Yamane-Ohnuki et al., "Establishment of FUT8 Knockout Chinese Hamster Ovary Cells: An Ideal Host Cell Line for Producing Completely Defucosylated Antibodies With Enhanced Antibody-Dependent Cellular Cytotoxicity," Biotechnology and Bioengineering, (2004) vol. 87, No. 5, pp. 614-622.
International Search Report dated Mar. 18, 2014 issued by the International Searching Authority in counterpart Application No. PCT/JP2013007529.
International Search Report dated Jun. 25, 2014, issued by the International Searching Authority in counterpart International Application No. PCT/JP2014/003409.
Bosch et al., Primary Liver Cancer: Worldwide Incidence and Trends, Gastroenterology vol. 127, No. 5, (2004) pp. S5-S14.
Llovet et al., Hepatocellular carcinoma, The Lancet, vol. 362, Dec. 6, 2003, pp. 1907-1917.
Yeo et al., Randomized Phase III Study of Doxorubicin Versus Cisplatin/Interferon α-2b/Doxorubicin/Fluorouracil (PIAF) Combination Chemotherapy for Unresectable Hepatocellular Carcinoma, Journal of the National Cancer Institute, vol. 97, No. 20, Oct. 19, 2005, pp. 1532-1538.
Takenaka et al., Results of 280 Liver Resections for Hepatocellular Carcinoma, Arch Surg, vol. 131, Jan. 1996, pp. 71-76.
Cheng et al., Efficacy and safety of sorafenib in patients in the Asia-Pacific region with advanced hepatocellular carcinoma: a phase III randomised, double-blind, placebo-controlled trial, The Lancet Oncology, vol. 10, Jan. 2009, pp. 25-34.
Llovet et al., Sorafenib in Advanced Hepatocellular Carcinoma, The New England Journal of Medicine, vol. 359, (2008) No. 4, pp. 378-390.
De Cat B et al., Processing by proprotein convertases is required for glypican-3 modulation of cell survival, Wnt signaling, and gastrulation movements, The Journal of Cell Biology, vol. 163, No. 3, (2003) pp. 625-635.
Traister et al., Mammalian Notum induces the release of glypicans and other GPI-anchored proteins from the cell surface, Biochemical Journal, vol. 410, (2008) pp. 503-511.
Ho et al., Glypican-3: A new target for cancer immunotherapy, European Journal of Cancer, vol. 47, (2011) pp. 333-338.
Zhu, Andrew X et al, First-in-Man Phase I Study of GC33, a Novel Recombinant Humanized Antibody Against Glypican-3, in Patients with Advanced Hepatocellular Carcinoma, Jan. 29, 2013, Clinical Cancer Research vol. 19 No. 4, pp. 920-928.
Sawada, Yu et al. Phase I Trial of a Glypican-3—Derived Peptide Vaccine for Advanced Hepatocellular Carcinoma: Immunologic Evidence and Potential for Improving Overall Survival, May 10, 2012, Clinical Cancer Research, vol. 18, No. 13, pp. 3686-3696.
Communication dated Feb. 5, 2016 from the Ecuadorian Intellectual Property Office in counterpart application No. SP-07-7463.
Tetsuya Nakatsura et al., "Glypican-3, overexpressed specifically in human hepatocellular carcinoma, is a novel tumor marker", Biochemical and Biophysical Research Communications, 2003, vol. 306, XP-002261242, pp. 16-25.
Josep M. Llovet et al., "A Molecular Signature to Discriminate Dysplastic Nodules From Early Hepatocellular Carcinoma in HCV Cirrhosis", Gastroenterology, 2006, vol. 131, No. 6, pp. 1758-1767.
Communication, dated Apr. 12, 2017, issued by the Indian Patent Office in counterpart Application No. 6501/CHENP/2010.
Communication, dated Jul. 19, 2017, issued by the Intellectual Property Office of India in counterpart Indian Patent Application No. 1929/CHENP/2006.
Communication dated Mar. 3, 2017, from the Indian Patent Office in Indian application No. 2347/CHENP/2008.
Office Action dated Apr. 4, 2017, issued in U.S. Appl. No. 14/505,932.
Office Action dated Mar. 24, 2017, issued in U.S. Appl. No. 14/629,967.
John Lund et al., "Multiple Interactions of IgG with its Core Oligosaccharide Can Modulate Recognition by Complement and Human Fcγ-Receptor I and Influence the Synthesis of Its Oligosaccharide Chains", The Journal of immunology, vol. 157,1996, p. 4963-4969.
Lazar, "Declaration of Dr. Greg A. Lazar Under 35 U.S.C. §1.131", dated Dec. 27, 2010 submitted in U.S. Appl. No. 11/841,564, p. 1-4 (141 pages in total).
Kappel et al., "Regulating gene expression in transgenic animals," Current Opinion in Biotechnology, vol. 3, 1992, pp. 548-553.
Paul, Fundamental Immunology, Third Edition, 1993, pp. 292-295, 6 pages in total.
Houdebine, "Production of pharmaceutical proteins from transgenic animals," Journal of Biotechnology, vol. 34, 1994, pp. 269-287.
Wall, "Transgenic Livestock: Progress and Prospects for the Future," Theriogenology, vol. 45, 1996, pp. 57-68.
Bendig, "Humanization of Rodent Monoclonal Antibodies by CDR Grafting," Methods: A Companion to Methods in Enzymology, vol. 8, 1995, pp. 83-93.
Office Action dated Jan. 19, 2017, issued by the USPTO in U.S. Appl. No. 14/713,461.
Notice of Allowance dated Oct. 27, 2016, from the Russian Patent Office in Russian application No. 2011 115 845/10.
Ed Harlow et al., "Antibodies, A Laboratory Manual", Cold Spring Harbor Laboratory, 1988, pp. 141-142 (total 7 pages).
Hirotake Takai et al., "Histopathological analyses of the antitumor activity of anti-glypican-3 antibody (GC33) in human liver cancer xenograft models", Cancer Biology & Therapy vol. 8, Issue 10, pp. 930-938; May 15, 2009, XP009142005.
Giuseppe Pilia et al., "Mutations in GPC3, a glypican gene, cause the Simpson-Golabi-Behmel overgrowth syndrome", Nature Genetics, vol. 12, Mar. 1996, pp. 241-247.
Chia-Jui Yen et al., "Randomized phase Two trial of intravenous RO5137382/GC33 at 1600 mg every other week and placebo in previously treated patients with unresectable advanced hepatocellular carcinoma (HCC; NCT01507168).", Gastrointestinal (Noncolorectal) Cancer, total 1 page.
Ghassan K. Abou-Alfa et al., "Randomized phase Two placebo controlled study of codrituzumab in previously treated patients with advanced hepatocellular carcinoma", Journal of Hepatology, 2016, vol. 65, pp. 289-295.
A.I. Semenova, "Monitoring of Treatment Efficacy and Detection of Recurrences Using Biomarkers", Practical Oncology vol. 12, No. 4, pp. 171-177 (2011), total 13 pages.
Lars Fischer et al., "The anti-lymphoma effect of antibody-mediated immunotherapy is based on an increased degranulation of peripheral blood natural killer (NK) cells", Elsevier, Experimental Hematology (2006) vol. 34, pp. 753-759.
Kazuya Ofuji et al., "2. Vaccine Therapy for Hepatic Cancer", Consensus of Cancer Therapy, May 31, 2013, vol. 12, No. 2, total 12 pages.
Communication, dated Nov. 28, 2017, from the European Patent Office in application No. 15789676.2.
Communication, dated Oct. 16, 2017, from the State Intellectual Property Office of the P.R.C. in application No. 201480071111.X.
Communication, dated Oct. 16, 2017, from the Intellectual Property Office of Singapore in application No. 11201609014T.
Office Action, dated Jan. 9, 2018, issued by the United States Patent and Trademark Office in U.S. Appl. No. 15/288,508.
Office Action, dated Jan. 19, 2018, issued by the United States Patent and Trademark Office in U.S. Appl. No. 15/309,391.
Communication, dated Feb. 8, 2018, from the Norwegian Industrial Property Office in application No. 20063539.
Communication, dated Dec. 7, 2017, from the Russian Patent and Trademark Office in application No. 2015129697.

(56) References Cited

OTHER PUBLICATIONS

Communication, dated Jan. 29, 2018, from Indian Intellectual Property Office in application No. 2357/CHENP/2010.
Lei, et al., "Prediction of HLA-A2 restricted cytotoxic T lymphocyte epitope in high expression of tumor antigen glypican-3 in primary liver cancer", Jiefangjun Yiyao Zazhishe, 2013, pp. 26-28, vol. 25, No. 8 (1 page total).
Zhang, et al., "Comparison of chemiluminescence enzyme immunoassay based on magnetic microparticles with traditional colorimetric ELISA for the detection of serum a-fetoprotein", J. of Pharmaceutical Analysis, 2012, pp. 130-135, vol. 2, No. 2 (6 pages total).
Hatjiharissi, et al., "Individuals Expressing FcγRIIIA-158 V/V and V/F Show Increased NK Cell Surface Expression of FcgRIIIA (CD16), Rituximab Binding, and Demonstrate Higher Levels of ADCC Activity in Response to Rituximab", Blood, 2005, vol. 106 (2 pages total).
Communication, dated Oct. 16, 2018, issued by the Brazilian Patent Office in application No. PI0506125-3.
Communication, dated Oct. 24, 2018, issued by the European Patent Office in application No. 16818042.0.
Communication, dated Sep. 26, 2018, issued by the Mexican Patent Office in application No. MX/a/2015/007714.
Communication, dated Nov. 7, 2018, issued by the European Patent Office in application No. 14874331.3.
Communication, dated Nov. 15, 2018, issued by the U.S. Patent and Trademark Office in U.S. Appl. No. 15/309,391.
Communication, dated Nov. 7, 2018, issued by the Brazilian Patent Office in application No. PI0617412-4.
Communication, dated Dec. 13, 2018, issued by the Australian Patent Office in application No. 2013365430.
Communication, dated Jan. 9, 2019, issued by the Intellectual Property Office of the P.R.C. in application No. 20161018223.5.
Communication, dated Feb. 7, 2019, issued by the European Patent Office in application No. 14874331.3.
Capurro M.I. et al; "Overexpression of Glypican-3 in human hepatocellular carcinomas determined by immunohistochemistry using a monoclonal antibody", Proceedings of The American Association for Cancer Research, 93rd Annual Meeting, vol. 43, Apr. 6-10, 2002, p. 219.
Hippo et al., "Identification of Soluble NH2-Terminal Fragment of Glypican-3 as a Serological Marker for Early-Stage Hepatocellular Carcinoma", Cancer Research, vol. 64, No. 7, Apr. 1, 2004, pp. 2418-2423.
Chen Min et al., Reevaluation of glypican-3 as a serological marker for hepatocellular carcinoma, Clinica Chimica Acta, vol. 423, 2013, pp. 105-111.
Yorita et al., "Prognostic significance of circumferential cell surface immunoreactivity of glypican-3 in hepatocellular carcinoma", Liver International, vol. 21, No. 1, Jan. 1, 2011, pp. 120-131.
Sun et al., "Suppression of Glypican 3 Inhibits Growth of Hepatocellular Carcinoma Cells through Up-Regulation of TGF-β2", Neoplasia, vol. 13, No. 8, Aug. 1, 2011, pp. 735-747 (14 pages).
Mavilio et al., "Characterization of CD56−/CD16+ natural killer (NK) cells: A highly dysfunctional NK subset expanded in HIV-infected viremic individuals", PNAS, vol. 102, No. 8, Feb. 22, 2005, pp. 2886-2891.
Hatjiharissi et al., "Increased natural killer cell expression of CD16, augmented binding and ADCC activity to rituximab among individuals expressing the FcγRIIIa-158 V/V and V/F polymorphism", Blood, vol. 110, No. 7, 2007, pp. 2561-2564.
Li S et al., "Prokaryotic Expression of GPC3/MXR7 and Preparation of Anti-GPC3/MXR7 Antibody", China Journal of Modern Medicine, vol. 13, No. 8, Apr. 30, 2003, pp. 15-17.
Haruyama Y et al., High preoperative levels of serum glypican-3 containing N-terminal subunit are associated with poor prognosis in patients with hepatocellular carcinoma after partial hepatectomy, International Journal of Cancer, vol. 137, No. 7, Oct. 1, 2015, pp. 1643-1651.
Communication, dated Sep. 18, 2019, issued by the Thailand Patent Office in Thailand Application No. 0501003166.
Office Action, dated May 4, 2018, issued by the United States Patent and Trademark Office in U.S. Appl. No. 15/107,316.
Office Action, dated May 15, 2018, issued by the United States Patent and Trademark Office in U.S. Appl. No. 15/309,391.
Office Action, dated Aug. 15, 2018, issued by the United States Patent and Trademark Office in U.S. Appl. No. 14/713,416.
Office Action, dated Sep. 21, 2018, issued by the United States Patent and Trademark Office in U.S. Appl. No. 15/288,508.
Communication, dated Apr. 18, 2018, issued by the Brazilian Patent Office in Application No. PI0909672-8.
Communication, dated Jun. 19, 2018, issued by the Japanese Patent Office in Application No. 2015-554492.
Communication, dated Sep. 5, 2018, issued by the State Intellectual Property Office of the People's Republic of China, in Application No. 201580024198.X.
Rudikoff, et al., "Single amino acid substitution altering antigen-binding specificity", Proc Natl. Acad. Sci., Mar. 1982, pp. 1979-1983, vol. 79, No. 6 (5 page total).
Amit, et al., "Three-Dimensional Structure of an Antigen-Antibody Complex at 2.8 A Resolution", Science, Aug. 15, 1986, pp. 747-753, vol. 233, No. 4765 (7 pages total).
Vajdos, et al., "Comprehensive Functional Maps of the Antigen-binding Site of an Anti-ErbB2 Antibody Obtained with Shotgun Scanning Mutagenesis", J. Mol. Biol., 2002, pp. 415-428, vol. 320, No. 2 (14 pages total).
Brown, et al., "Tolerance to Single, but Not Multiple, Amino Acid Replacements to Antibody VH CDR2", The Journal of Immunology, 1996, pp. 3285-3291, vol. 156 (7 pages total).
Zynger, et al., "Glypican 3: A Novel Marker in Testicular Germ Cell Tumors", American Journal of Surgical Pathology, Dec. 2006, pp. 1570-1575, vol. 30, No. 12 (6 pages total).
Ishiguro, et al., "Anti-Glypican 3 Antibody as a Potential Antitumor Agent for Human Liver Cancer", Cancer Res, Dec. 1, 2008, pp. 9832-9838, vol. 68, No. 23 (7 pages total).
Nakano, et al., "Anti-Glypican 3 antibodies cause Adcc against human hepatocellular carcinoma cells", Biochemical and Biophysical Research Communications, 2009, pp. 279-284, vol. 378, No. 2 (6 pages total).
Colman, "Effects of amino acid sequence changes on antibody-antigen interactions", Research in Immunology, 1994, pp. 33-36, vol. 145 (4 pages total).
Van Regenmortel, "Mapping Epitope Structure and Activity: From One-Dimensional Prediction to Four-Dimensional Description of Antigenic Specificity", a Companion to Methods in Enzymology, 1996, pp. 465-472, vol. 9 (8 pages total).
Kim, et al., "Structure of the protein core of the glypican Dally-like and localization of a region important for hedgehog signaling", PNAS, Aug. 9, 2011, pp. 13122-13117, vol. 108, No. 32 (8 pages total).
Lei, et al., "Prediction of HLA-A2 restricted cytotoxic T lymphocyte epitope in high expression of tumor antigen glypican-3 in primary liver cancer", Jiefangjun Yiyao Zazhishe, 2013, pp. 26-28, vol. 25, No. 8 (1 page total) English.
Creative Diagnostics, "Lateral Flow Immunoassays", Test & Assay Development, 2009 (4 pages total).
Zhang, et al., "Comparison of chemiluminescence enzyme immunoassay based on magnetic microparticles with traditional colorimetric ELISA for the detection of serum α-fetoprotein", J. of Pharmaceutical Analysis, 2012, pp. 130-135, vol. 2, No. 2 (6 pages total).
Harlow, et al., "Antibodies a Laboratory Manual", Cold Spring Harbor Laboratory Press, 1988 (4 pages total).
Weisstein, "Combination", MathWorld—A Wolfram Web Resource, downloaded from http://mathworld.wolfram.com/Combination.html, 2018 (1 page total).
Department of Commerce, United States Patent and Trademark Office, Federal Register, Jan. 5, 2001, pp. 1099-1111, vol. 66, No. 4 (13 pages total).
Khantasup, et al., "Design and Generation of Humanized Single-chain Fv Derived from Mouse Hybridoma for Potential Targeting Application", Monoclonal Antibodies in Immunodiagnosis and Immunotherapy, 2015, pp. 404-417, vol. 34, No. 6 (14 pages total).

(56) References Cited

OTHER PUBLICATIONS

Gluck, et al., "Phase I Studies of Interleukin (IL)-2 and Rituximab in B-Cell Non-Hodgkin's Lymphoma: Il-2 Mediated Natural Killer Cell Expansion Correlations with Clinical Response", Clinical Cancer Research, Apr. 1, 2004, pp. 2253-2264, vol. 10 (13 pages total).

Yamauchi, et al., "The glypican 3 oncofetal protein is a promising diagnostic marker for hepatocellular carcinoma", Modern Pathology, 2005, pp. 1591-1598, vol. 18 (8 pages total).

Almagro, et al., "Humanization of antibodies", Frontiers in Bioscience, Jan. 1, 2008, pp. 1619-1633, vol. 13 (15 pages total).

Hatjiharissi, et al., "Individuals Expressing FcTRIIIA-158 V/V and V/F Show Increased NK Cell Surface Expression of FcgRIIIA (CD16), Rituximab Binding, and Demonstrate Higher Levels of ADCC Activity in Response to Rituximab", Blood, 2005, vol. 106 (2 pages total).

\* cited by examiner

```
                          SEQUENCE LISTING

<160> NUMBER OF SEQ ID NOS: 90

<210> SEQ ID NO 1
<211> LENGTH: 580
<212> TYPE: PRT
<213> ORGANISM: homo sapiens

<400> SEQUENCE: 1

Met Ala Gly Thr Val Arg Thr Ala Cys Leu Val Val Ala Met Leu Leu
1               5                   10                  15

Ser Leu Asp Phe Pro Gly Gln Ala Gln Pro Pro Pro Pro Pro Asp
            20                  25                  30

Ala Thr Cys His Gln Val Arg Ser Phe Phe Gln Arg Leu Gln Pro Gly
        35                  40                  45

Leu Lys Trp Val Pro Glu Thr Pro Val Pro Gly Ser Asp Leu Gln Val
    50                  55                  60

Cys Leu Pro Lys Gly Pro Thr Cys Cys Ser Arg Lys Met Glu Glu Lys
65                  70                  75                  80

Tyr Gln Leu Thr Ala Arg Leu Asn Met Glu Gln Leu Leu Gln Ser Ala
                85                  90                  95

Ser Met Glu Leu Lys Phe Leu Ile Ile Gln Asn Ala Ala Val Phe Gln
            100                 105                 110

Glu Ala Phe Glu Ile Val Val Arg His Ala Lys Asn Tyr Thr Asn Ala
        115                 120                 125

Met Phe Lys Asn Asn Tyr Pro Ser Leu Thr Pro Gln Ala Phe Glu Phe
    130                 135                 140

Val Gly Glu Phe Phe Thr Asp Val Ser Leu Tyr Ile Leu Gly Ser Asp
145                 150                 155                 160

Ile Asn Val Asp Asp Met Val Asn Glu Leu Phe Asp Ser Leu Phe Pro
                165                 170                 175
```

```
Val Ile Tyr Thr Gln Leu Met Asn Pro Gly Leu Pro Asp Ser Ala Leu
            180                 185                 190

Asp Ile Asn Glu Cys Leu Arg Gly Ala Arg Arg Asp Leu Lys Val Phe
            195                 200                 205

Gly Asn Phe Pro Lys Leu Ile Met Thr Gln Val Ser Lys Ser Leu Gln
            210                 215                 220

Val Thr Arg Ile Phe Leu Gln Ala Leu Asn Leu Gly Ile Glu Val Ile
225                 230                 235                 240

Asn Thr Thr Asp His Leu Lys Phe Ser Lys Asp Cys Gly Arg Met Leu
            245                 250                 255

Thr Arg Met Trp Tyr Cys Ser Tyr Cys Gln Gly Leu Met Met Val Lys
            260                 265                 270

Pro Cys Gly Gly Tyr Cys Asn Val Val Met Gln Gly Cys Met Ala Gly
            275                 280                 285

Val Val Glu Ile Asp Lys Tyr Trp Arg Glu Tyr Ile Leu Ser Leu Glu
            290                 295                 300

Glu Leu Val Asn Gly Met Tyr Arg Ile Tyr Asp Met Glu Asn Val Leu
305                 310                 315                 320

Leu Gly Leu Phe Ser Thr Ile His Asp Ser Ile Gln Tyr Val Gln Lys
            325                 330                 335

Asn Ala Gly Lys Leu Thr Thr Ile Gly Lys Leu Cys Ala His Ser
            340                 345                 350

Gln Gln Arg Gln Tyr Arg Ser Ala Tyr Tyr Pro Glu Asp Leu Phe Ile
            355                 360                 365

Asp Lys Lys Val Leu Lys Val Ala His Val Glu His Glu Thr Leu
            370                 375                 380

Ser Ser Arg Arg Arg Glu Leu Ile Gln Lys Leu Lys Ser Phe Ile Ser
385                 390                 395                 400

Phe Tyr Ser Ala Leu Pro Gly Tyr Ile Cys Ser His Ser Pro Val Ala
            405                 410                 415

Glu Asn Asp Thr Leu Cys Trp Asn Gly Gln Glu Leu Val Glu Arg Tyr
            420                 425                 430

Ser Gln Lys Ala Ala Arg Asn Gly Met Lys Asn Gln Phe Asn Leu His
            435                 440                 445

Glu Leu Lys Met Lys Gly Pro Glu Pro Val Val Ser Gln Ile Ile Asp
            450                 455                 460

Lys Leu Lys His Ile Asn Gln Leu Leu Arg Thr Met Ser Met Pro Lys
465                 470                 475                 480

Gly Arg Val Leu Asp Lys Asn Leu Asp Glu Glu Gly Phe Glu Ser Gly
            485                 490                 495

Asp Cys Gly Asp Asp Glu Asp Glu Cys Ile Gly Gly Ser Gly Asp Gly
            500                 505                 510

Met Ile Lys Val Lys Asn Gln Leu Arg Phe Leu Ala Glu Leu Ala Tyr
            515                 520                 525

Asp Leu Asp Val Asp Asp Ala Pro Gly Asn Ser Gln Gln Ala Thr Pro
            530                 535                 540

Lys Asp Asn Glu Ile Ser Thr Phe His Asn Leu Gly Asn Val His Ser
545                 550                 555                 560

Pro Leu Lys Leu Leu Thr Ser Met Ala Ile Ser Val Val Cys Phe Phe
            565                 570                 575

Phe Leu Val His
            580
```

```
<210> SEQ ID NO 2
<211> LENGTH: 9
<212> TYPE: PRT
<213> ORGANISM: homo sapiens

<400> SEQUENCE: 2

Phe Val Gly Glu Phe Phe Thr Asp Val
1               5

<210> SEQ ID NO 3
<211> LENGTH: 9
<212> TYPE: PRT
<213> ORGANISM: homo sapiens

<400> SEQUENCE: 3

Glu Tyr Ile Leu Ser Leu Glu Glu Leu
1               5

<210> SEQ ID NO 4
<211> LENGTH: 5
<212> TYPE: PRT
<213> ORGANISM: Mus musculus

<400> SEQUENCE: 4

Asp Tyr Ser Met His
1               5

<210> SEQ ID NO 5
<211> LENGTH: 17
<212> TYPE: PRT
<213> ORGANISM: Mus musculus

<400> SEQUENCE: 5

Trp Ile Asn Thr Glu Thr Gly Glu Pro Thr Tyr Ala Asp Asp Phe Lys
1               5                   10                  15

Gly

<210> SEQ ID NO 6
<211> LENGTH: 2
<212> TYPE: PRT
<213> ORGANISM: Mus musculus

<400> SEQUENCE: 6

Leu Tyr
1

<210> SEQ ID NO 7
<211> LENGTH: 16
<212> TYPE: PRT
<213> ORGANISM: Mus musculus

<400> SEQUENCE: 7

Lys Ser Ser Gln Ser Leu Leu His Ser Asp Gly Lys Thr Phe Leu Asn
1               5                   10                  15

<210> SEQ ID NO 8
<211> LENGTH: 7
<212> TYPE: PRT
<213> ORGANISM: Mus musculus

<400> SEQUENCE: 8

Leu Val Ser Arg Leu Asp Ser
1               5
```

```
<210> SEQ ID NO 9
<211> LENGTH: 9
<212> TYPE: PRT
<213> ORGANISM: Mus musculus

<400> SEQUENCE: 9

Cys Gln Gly Thr His Phe Pro Arg Thr
1               5

<210> SEQ ID NO 10
<211> LENGTH: 111
<212> TYPE: PRT
<213> ORGANISM: Mus musculus

<400> SEQUENCE: 10

Gln Ile Gln Leu Glu Gln Ser Gly Pro Glu Leu Lys Lys Pro Gly Glu
1               5                   10                  15

Thr Val Lys Ile Ser Cys Lys Ala Ser Gly Tyr Ile Phe Arg Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Thr Ser Leu Tyr Trp Gly Gln Gly Thr Leu Val Thr Val Ser Ala
            100                 105                 110

<210> SEQ ID NO 11
<211> LENGTH: 112
<212> TYPE: PRT
<213> ORGANISM: Mus musculus

<400> SEQUENCE: 11

Asp Val Val Met Thr Gln Thr Pro Leu Thr Leu Ser Val Thr Leu Gly
1               5                   10                  15

Gln Pro Ala Ser Ile Ser Cys Lys Ser Ser Gln Ser Leu Leu His Ser
            20                  25                  30

Asp Gly Lys Thr Phe Leu Asn Trp Leu Leu Gln Arg Pro Gly Gln Ser
        35                  40                  45

Pro Lys Arg Leu Ile Tyr Leu Val Ser Arg Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Cys Gln Gly
                85                  90                  95

Thr His Phe Pro Arg Thr Phe Gly Gly Gly Thr Arg Leu Glu Ile Lys
            100                 105                 110

<210> SEQ ID NO 12
<211> LENGTH: 7
<212> TYPE: PRT
<213> ORGANISM: Mus musculus

<400> SEQUENCE: 12

Thr Tyr Gly Met Gly Val Gly
1               5
```

```
<210> SEQ ID NO 13
<211> LENGTH: 16
<212> TYPE: PRT
<213> ORGANISM: Mus musculus

<400> SEQUENCE: 13

Asn Ile Trp Trp His Asp Asp Lys Tyr Tyr Asn Ser Ala Leu Lys Ser
1               5                   10                  15

<210> SEQ ID NO 14
<211> LENGTH: 14
<212> TYPE: PRT
<213> ORGANISM: Mus musculus

<400> SEQUENCE: 14

Ile Ala Pro Arg Tyr Asn Lys Tyr Glu Gly Phe Phe Ala Phe
1               5                   10

<210> SEQ ID NO 15
<211> LENGTH: 16
<212> TYPE: PRT
<213> ORGANISM: Mus musculus

<400> SEQUENCE: 15

Arg Ser Ser Gln Ser Ile Val His Ser Asn Gly Asn Thr Tyr Leu Glu
1               5                   10                  15

<210> SEQ ID NO 16
<211> LENGTH: 7
<212> TYPE: PRT
<213> ORGANISM: Mus musculus

<400> SEQUENCE: 16

Lys Val Ser Asn Arg Phe Ser
1               5

<210> SEQ ID NO 17
<211> LENGTH: 9
<212> TYPE: PRT
<213> ORGANISM: Mus musculus

<400> SEQUENCE: 17

Phe Gln Gly Ser His Val Pro Trp Thr
1               5

<210> SEQ ID NO 18
<211> LENGTH: 124
<212> TYPE: PRT
<213> ORGANISM: Mus musculus

<400> SEQUENCE: 18

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Met Gly Val Gly Trp Ile Arg Gln Pro Ser Gly Lys Gly Leu Glu
        35                  40                  45

Trp Leu Ala Asn Ile Trp Trp His Asp Asp Lys Tyr Tyr Asn Ser Ala
    50                  55                  60

Leu Lys Ser Arg Leu Thr Ile Ser Lys Asp Ile Ser Asn Asn Gln Val
65                  70                  75                  80

Phe Leu Lys Ile Ser Ser Val Asp Thr Ala Asp Thr Ala Thr Tyr Tyr
                85                  90                  95
```

```
Cys Ala Gln Ile Ala Pro Arg Tyr Asn Lys Tyr Glu Gly Phe Ala
            100                 105                 110
Phe Trp Gly Gln Gly Thr Leu Val Thr Val Ser Ala
        115                 120

<210> SEQ ID NO 19
<211> LENGTH: 112
<212> TYPE: PRT
<213> ORGANISM: Mus musculus

<400> SEQUENCE: 19

Asp Val Leu Met Thr Gln Thr Pro Leu Ser Leu Pro Val Ser Leu Gly
1               5                   10                  15
Asp Gln Ala Ser Ile Ser Cys Arg Ser Ser Gln Ser Ile Val His Ser
            20                  25                  30
Asn Gly Asn Thr Tyr Leu Glu Trp Tyr Leu Gln Lys Pro Gly Gln Ser
        35                  40                  45
Pro Lys Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Tyr Cys Phe Gln Gly
                85                  90                  95
Ser His Val Pro Trp Thr Phe Gly Gly Gly Thr Lys Leu Glu Ile Lys
            100                 105                 110

<210> SEQ ID NO 20
<211> LENGTH: 5
<212> TYPE: PRT
<213> ORGANISM: Mus musculus

<400> SEQUENCE: 20

Asp Tyr Glu Met His
1               5

<210> SEQ ID NO 21
<211> LENGTH: 17
<212> TYPE: PRT
<213> ORGANISM: Mus musculus

<400> SEQUENCE: 21

Ala Leu Asp Pro Lys Thr Gly Asp Thr Ala Tyr Ser Gln Lys Phe Lys
1               5                   10                  15
Gly

<210> SEQ ID NO 22
<211> LENGTH: 6
<212> TYPE: PRT
<213> ORGANISM: Mus musculus

<400> SEQUENCE: 22

Phe Tyr Ser Tyr Thr Tyr
1               5

<210> SEQ ID NO 23
<211> LENGTH: 16
<212> TYPE: PRT
<213> ORGANISM: Mus musculus
```

```
<400> SEQUENCE: 23

Arg Ser Ser Gln Ser Leu Val His Ser Asn Gly Asn Thr Tyr Leu His
1               5                   10                  15

<210> SEQ ID NO 24
<211> LENGTH: 7
<212> TYPE: PRT
<213> ORGANISM: Mus musculus

<400> SEQUENCE: 24

Lys Val Ser Asn Arg Phe Ser
1               5

<210> SEQ ID NO 25
<211> LENGTH: 9
<212> TYPE: PRT
<213> ORGANISM: Mus musculus

<400> SEQUENCE: 25

Ser Gln Asn Thr His Val Pro Pro Thr
1               5

<210> SEQ ID NO 26
<211> LENGTH: 115
<212> TYPE: PRT
<213> ORGANISM: Mus musculus

<400> SEQUENCE: 26

Gln Val Gln Leu Gln Gln Ser Gly Ala Glu Leu Val Arg Pro Gly Ala
1               5                   10                  15

Ser Val Lys Leu Ser Cys Lys Ala Ser Gly Tyr Thr Phe Thr Asp Tyr
                20                  25                  30

Glu Met His Trp Val Lys Gln Thr Pro Val His Gly Leu Lys Trp Ile
            35                  40                  45

Gly Ala Leu Asp Pro Lys Thr Gly Asp Thr Ala Tyr Ser Gln Lys Phe
        50                  55                  60

Lys Gly Lys Ala Thr Leu Thr Ala Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Phe Tyr Ser Tyr Thr Tyr Trp Gly Gln Gly Thr Leu Val Thr
                100                 105                 110

Val Ser Ala
        115

<210> SEQ ID NO 27
<211> LENGTH: 112
<212> TYPE: PRT
<213> ORGANISM: Mus musculus

<400> SEQUENCE: 27

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asn
            85                  90                  95

Thr His Val Pro Pro Thr Phe Gly Ser Gly Thr Lys Leu Glu Ile Lys
            100                 105                 110

<210> SEQ ID NO 28
<211> LENGTH: 5
<212> TYPE: PRT
<213> ORGANISM: Mus musculus

<400> SEQUENCE: 28

Ile Asn Ala Met Asn
1               5

<210> SEQ ID NO 29
<211> LENGTH: 19
<212> TYPE: PRT
<213> ORGANISM: Mus musculus

<400> SEQUENCE: 29

Arg Ile Arg Ser Glu Ser Asn Asn Tyr Ala Thr Tyr Tyr Gly Asp Ser
1               5                   10                  15

Val Lys Asp

<210> SEQ ID NO 30
<211> LENGTH: 8
<212> TYPE: PRT
<213> ORGANISM: Mus musculus

<400> SEQUENCE: 30

Glu Val Thr Thr Ser Phe Ala Tyr
1               5

<210> SEQ ID NO 31
<211> LENGTH: 16
<212> TYPE: PRT
<213> ORGANISM: Mus musculus

<400> SEQUENCE: 31

Lys Ser Ser Lys Ser Leu Leu His Ser Asn Gly Asn Thr Tyr Leu Asn
1               5                   10                  15

<210> SEQ ID NO 32
<211> LENGTH: 7
<212> TYPE: PRT
<213> ORGANISM: Mus musculus

<400> SEQUENCE: 32

Trp Met Ser Asn Leu Ala Ser
1               5

<210> SEQ ID NO 33
<211> LENGTH: 9
<212> TYPE: PRT
<213> ORGANISM: Mus musculus

<400> SEQUENCE: 33

Met Gln His Ile Glu Tyr Pro Phe Thr
1               5

<210> SEQ ID NO 34
<211> LENGTH: 119
<212> TYPE: PRT
<213> ORGANISM: Mus musculus

<400> SEQUENCE: 34

```
Glu Val Gln Leu Val Glu Thr Gly Gly Gly Leu Val Gln Pro Glu Gly
1               5                   10                  15

Ser Leu Lys Leu Ser Cys Ala Ala Ser Gly Phe Ser Phe Asn Ile Asn
            20                  25                  30

Ala Met Asn Trp Val Arg Gln Ala Pro Gly Lys Gly Leu Glu Trp Val
        35                  40                  45

Ala Arg Ile Arg Ser Glu Ser Asn Asn Tyr Ala Thr Tyr Tyr Gly Asp
    50                  55                  60

Ser Val Lys Asp Arg Phe Thr Ile Ser Arg Asp Asp Ser Gln Asn Met
65                  70                  75                  80

Leu Tyr Leu Gln Met Asn Asn Leu Lys Thr Glu Asp Thr Ala Ile Tyr
                85                  90                  95

Tyr Cys Val Arg Glu Val Thr Thr Ser Phe Ala Tyr Trp Gly Gln Gly
            100                 105                 110

Thr Leu Val Thr Val Ser Ala
        115
```

<210> SEQ ID NO 35
<211> LENGTH: 112
<212> TYPE: PRT
<213> ORGANISM: Mus musculus

<400> SEQUENCE: 35

```
Asp Ile Val Met Thr Gln Ser Ala Pro Ser Val Pro Val Thr Pro Gly
1               5                   10                  15

Glu Ser Val Ser Ile Ser Cys Lys Ser Ser Lys Ser Leu Leu His Ser
            20                  25                  30

Asn Gly Asn Thr Tyr Leu Asn Trp Phe Leu Gln Arg Pro Gly Gln Ser
        35                  40                  45

Pro Gln Leu Leu Ile Tyr Trp Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Ile Glu Tyr Pro Phe Thr Phe Gly Thr Gly Thr Lys Leu Glu Ile Lys
            100                 105                 110
```

<210> SEQ ID NO 36
<211> LENGTH: 5
<212> TYPE: PRT
<213> ORGANISM: Mus musculus

<400> SEQUENCE: 36

```
Ala Ser Ala Met Asn
1               5
```

<210> SEQ ID NO 37
<211> LENGTH: 19
<212> TYPE: PRT
<213> ORGANISM: Mus musculus -continued

```
<400> SEQUENCE: 37

Arg Ile Arg Ser Lys Ser Asn Asn Tyr Ala Ile Tyr Tyr Ala Asp Ser
1               5                   10                  15

Val Lys Asp

<210> SEQ ID NO 38
<211> LENGTH: 12
<212> TYPE: PRT
<213> ORGANISM: Mus musculus

<400> SEQUENCE: 38

Asp Pro Gly Tyr Tyr Gly Asn Pro Trp Phe Ala Tyr
1               5                   10

<210> SEQ ID NO 39
<211> LENGTH: 16
<212> TYPE: PRT
<213> ORGANISM: Mus musculus

<400> SEQUENCE: 39

Arg Ser Ser Lys Ser Leu Leu His Ser Tyr Asp Ile Thr Tyr Leu Tyr
1               5                   10                  15

<210> SEQ ID NO 40
<211> LENGTH: 7
<212> TYPE: PRT
<213> ORGANISM: Mus musculus

<400> SEQUENCE: 40

Gln Met Ser Asn Leu Ala Ser
1               5

<210> SEQ ID NO 41
<211> LENGTH: 9
<212> TYPE: PRT
<213> ORGANISM: Mus musculus

<400> SEQUENCE: 41

Ala Gln Asn Leu Glu Leu Pro Pro Thr
1               5

<210> SEQ ID NO 42
<211> LENGTH: 123
<212> TYPE: PRT
<213> ORGANISM: Mus musculus

<400> SEQUENCE: 42

Glu Val Gln Leu Val Glu Thr Gly Gly Gly Leu Val Gln Pro Lys Gly
1               5                   10                  15

Ser Leu Lys Leu Ser Cys Ala Ala Ser Gly Phe Thr Phe Asn Ala Ser
                20                  25                  30

Ala Met Asn Trp Val Arg Gln Ala Pro Gly Lys Gly Leu Glu Trp Val
            35                  40                  45

Ala Arg Ile Arg Ser Lys Ser Asn Asn Tyr Ala Ile Tyr Tyr Ala Asp
        50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95
```

```
Tyr Cys Val Arg Asp Pro Gly Tyr Tyr Gly Asn Pro Trp Phe Ala Tyr
            100                 105                 110

Trp Gly Gln Gly Thr Leu Val Thr Val Ser Ala
        115                 120

<210> SEQ ID NO 43
<211> LENGTH: 112
<212> TYPE: PRT
<213> ORGANISM: Mus musculus

<400> SEQUENCE: 43

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Tyr Asp Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Pro Thr Phe Gly Gly Gly Thr Lys Leu Glu Ile Lys
            100                 105                 110

<210> SEQ ID NO 44
<211> LENGTH: 115
<212> TYPE: PRT
<213> ORGANISM: Artificial Sequence
<220> FEATURE:
<223> OTHER INFORMATION: modified antibody fragment

<400> SEQUENCE: 44

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Tyr Ser Tyr Thr Tyr Trp Gly Gln Gly Thr Leu Val Thr
            100                 105                 110

Val Ser Ser
        115

<210> SEQ ID NO 45
<211> LENGTH: 115
<212> TYPE: PRT
<213> ORGANISM: Artificial Sequence
<220> FEATURE:
<223> OTHER INFORMATION: modified antibody fragment
```

<400> SEQUENCE: 45

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 46
<211> LENGTH: 115
<212> TYPE: PRT
<213> ORGANISM: Artificial Sequence
<220> FEATURE:
<223> OTHER INFORMATION: modified antibody fragment

<400> SEQUENCE: 46

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 47
<211> LENGTH: 115
<212> TYPE: PRT
<213> ORGANISM: Artificial Sequence
<220> FEATURE:
<223> OTHER INFORMATION: modified antibody fragment

<400> SEQUENCE: 47

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
            50                  55                  60

Lys Gly Arg Val Thr Leu Thr Ala Asp Lys Ser Thr Ser Thr Ala Tyr
 65                  70                  75                  80

Met Glu Leu Ser Ser Leu Thr Ser Glu Asp Thr Ala Val Tyr Tyr Cys
                    85                  90                  95

Thr Arg Phe Tyr Ser Tyr Thr Tyr Trp Gly Gln Gly Thr Leu Val Thr
                100                 105                 110

Val Ser Ser
        115

<210> SEQ ID NO 48
<211> LENGTH: 115
<212> TYPE: PRT
<213> ORGANISM: Artificial Sequence
<220> FEATURE:
<223> OTHER INFORMATION: modified antibody fragment

<400> SEQUENCE: 48

Gln Val Gln Leu Val Gln Ser Gly Ala Glu Val Lys Lys Pro Gly Ala
 1               5                   10                  15

Ser Val Lys Val Ser Cys Lys Ala Ser Gly Tyr Thr Phe Thr Asp Tyr
                20                  25                  30

Glu Met His Trp Val Arg Gln Ala Pro Gly Gln Gly Leu Glu Trp Met
            35                  40                  45

Gly Ala Leu Asp Pro Lys Thr Gly Asp Thr Ala Tyr Ser Gln Lys Phe
        50                  55                  60

Lys Gly Arg Val Thr Leu Thr Ala Asp Glu Ser Thr Ser Thr Ala Tyr
 65                 70                  75                  80

Met Glu Leu Ser Ser Leu Arg Ser Glu Asp Thr Ala Val Tyr Tyr Cys
                85                  90                  95

Thr Arg Phe Tyr Ser Tyr Thr Tyr Trp Gly Gln Gly Thr Leu Val Thr
                100                 105                 110

Val Ser Ser
        115

<210> SEQ ID NO 49
<211> LENGTH: 115
<212> TYPE: PRT
<213> ORGANISM: Artificial Sequence
<220> FEATURE:
<223> OTHER INFORMATION: modified antibody fragment

<400> SEQUENCE: 49

Gln Val Gln Leu Val Gln Ser Gly Ala Glu Val Lys Lys Pro Gly Ala
 1               5                   10                  15

Ser Val Lys Val Ser Cys Lys Ala Ser Gly Tyr Thr Phe Thr Asp Tyr
                20                  25                  30

Glu Met His Trp Val Arg Gln Ala Pro Gly Gln Gly Leu Glu Trp Met
            35                  40                  45

Gly Ala Leu Asp Pro Lys Thr Gly Asp Thr Ala Tyr Ser Gln Lys Phe
        50                  55                  60

Lys Gly Arg Val Thr Leu Thr Ala Asp Lys Ser Thr Ser Thr Ala Tyr
 65                 70                  75                  80

Met Glu Leu Ser Ser Leu Arg Ser Glu Asp Thr Ala Val Tyr Tyr Cys
                85                  90                  95

```
Thr Arg Phe Tyr Ser Tyr Thr Tyr Trp Gly Gln Gly Thr Leu Val Thr
            100                 105                 110

Val Ser Ser
        115

<210> SEQ ID NO 50
<211> LENGTH: 115
<212> TYPE: PRT
<213> ORGANISM: Artificial Sequence
<220> FEATURE:
<223> OTHER INFORMATION: modified antibody fragment

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 51
<211> LENGTH: 112
<212> TYPE: PRT
<213> ORGANISM: Artificial Sequence
<220> FEATURE:
<223> OTHER INFORMATION: modified antibody fragment

<400> SEQUENCE: 51

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 52
<211> LENGTH: 112
<212> TYPE: PRT
<213> ORGANISM: Artificial Sequence
<220> FEATURE:
<223> OTHER INFORMATION: modified antibody fragment
```

<400> SEQUENCE: 52

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Ala Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 53
<211> LENGTH: 112
<212> TYPE: PRT
<213> ORGANISM: Artificial Sequence
<220> FEATURE:
<223> OTHER INFORMATION: modified antibody fragment

<400> SEQUENCE: 53

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Asp Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 54
<211> LENGTH: 112
<212> TYPE: PRT
<213> ORGANISM: Artificial Sequence
<220> FEATURE:
<223> OTHER INFORMATION: modified antibody fragment

<400> SEQUENCE: 54

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Glu Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

```
Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 55
<211> LENGTH: 112
<212> TYPE: PRT
<213> ORGANISM: Artificial Sequence
<220> FEATURE:
<223> OTHER INFORMATION: modified antibody fragment

<400> SEQUENCE: 55

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Phe Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 56
<211> LENGTH: 112
<212> TYPE: PRT
<213> ORGANISM: Artificial Sequence
<220> FEATURE:
<223> OTHER INFORMATION: modified antibody fragment

<400> SEQUENCE: 56

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn His Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 57
<211> LENGTH: 112
<212> TYPE: PRT
<213> ORGANISM: Artificial Sequence
<220> FEATURE:
<223> OTHER INFORMATION: modified antibody fragment
```

<400> SEQUENCE: 57

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Asn Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 58
<211> LENGTH: 112
<212> TYPE: PRT
<213> ORGANISM: Artificial Sequence
<220> FEATURE:
<223> OTHER INFORMATION: modified antibody fragment

<400> SEQUENCE: 58

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Thr Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 59
<211> LENGTH: 112
<212> TYPE: PRT
<213> ORGANISM: Artificial Sequence
<220> FEATURE:
<223> OTHER INFORMATION: modified antibody fragment

<400> SEQUENCE: 59

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gln Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

```
Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 60
<211> LENGTH: 112
<212> TYPE: PRT
<213> ORGANISM: Artificial Sequence
<220> FEATURE:
<223> OTHER INFORMATION: modified antibody fragment

<400> SEQUENCE: 60

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Ile Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 61
<211> LENGTH: 112
<212> TYPE: PRT
<213> ORGANISM: Artificial Sequence
<220> FEATURE:
<223> OTHER INFORMATION: modified antibody fragment

<400> SEQUENCE: 61

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Lys Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 62
<211> LENGTH: 112
<212> TYPE: PRT
<213> ORGANISM: Artificial Sequence
<220> FEATURE:
<223> OTHER INFORMATION: modified antibody fragment
```

```
<400> SEQUENCE: 62

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Leu Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
                100                 105                 110

<210> SEQ ID NO 63
<211> LENGTH: 112
<212> TYPE: PRT
<213> ORGANISM: Artificial Sequence
<220> FEATURE:
<223> OTHER INFORMATION: modified antibody fragment

<400> SEQUENCE: 63

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Ser Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
                100                 105                 110

<210> SEQ ID NO 64
<211> LENGTH: 112
<212> TYPE: PRT
<213> ORGANISM: Artificial Sequence
<220> FEATURE:
<223> OTHER INFORMATION: modified antibody fragment

<400> SEQUENCE: 64

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Trp Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80
```

```
Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 65
<211> LENGTH: 112
<212> TYPE: PRT
<213> ORGANISM: Artificial Sequence
<220> FEATURE:
<223> OTHER INFORMATION: modified antibody fragment

<400> SEQUENCE: 65

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Tyr Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 66
<211> LENGTH: 112
<212> TYPE: PRT
<213> ORGANISM: Artificial Sequence
<220> FEATURE:
<223> OTHER INFORMATION: modified antibody fragment

<400> SEQUENCE: 66

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 67
<211> LENGTH: 115
<212> TYPE: PRT
<213> ORGANISM: Artificial Sequence
<220> FEATURE:
<223> OTHER INFORMATION: modified antibody fragment
```

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Ile Arg Gln Pro Pro Gly Lys Gly Leu Glu Trp Ile
        35                  40                  45

Gly Ala Ile Asn Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Arg Gly Thr Leu Val Thr
            100                 105                 110

Val Ser Ser
        115

<210> SEQ ID NO 68
<211> LENGTH: 112
<212> TYPE: PRT
<213> ORGANISM: Artificial Sequence
<220> FEATURE:
<223> OTHER INFORMATION: modified antibody fragment

<400> SEQUENCE: 68

Asp Ile Val Met Thr Gln Ser Pro Leu Ser Leu Pro Val Thr Pro Gly
1               5                   10                  15

Gln Pro Ala Ser Ile Ser Cys Arg Ala Ser Arg Ser Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Arg Gly Thr Lys Leu Glu Ile Lys
            100                 105                 110

<210> SEQ ID NO 69
<211> LENGTH: 115
<212> TYPE: PRT
<213> ORGANISM: Artificial Sequence
<220> FEATURE:
<223> OTHER INFORMATION: modified antibody fragment

<400> SEQUENCE: 69

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Glu Met His Trp Ile Arg Gln Pro Pro Gly Glu Gly Leu Glu Trp Ile
        35                  40                  45

Gly Ala Ile Asp Pro Lys Thr Gly Asp Thr Ala Tyr Ser Gln Ser Phe
    50                  55                  60

```
Gln Asp Arg Val Thr Leu Thr Ala Asp Lys Ser Thr Ser Thr Ala Tyr
 65                  70                  75                  80

Met Glu Leu Ser Ser Leu Thr Ser Glu Asp Thr Ala Val Tyr Tyr Cys
                 85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 70
<211> LENGTH: 112
<212> TYPE: PRT
<213> ORGANISM: Artificial Sequence
<220> FEATURE:
<223> OTHER INFORMATION: modified antibody fragment

<400> SEQUENCE: 70

Asp Ile Val Met Thr Gln Ser Pro Leu Ser Leu Pro Val Thr Pro Gly
 1               5                  10                  15

Glu Pro Ala Ser Ile Ser Cys Arg Ala Ser Glu Ser Leu Val His Ser
                 20                  25                  30

Asn Arg Asn Thr Tyr Leu His Trp Tyr Gln Gln Lys Pro Gly Gln Ala
             35                  40                  45

Pro Arg Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Thr Ile
 65                  70                  75                  80

Ser Ser Leu Gln Ala Glu Asp Val Gly Val Tyr Tyr Cys Ser Gln Asn
                 85                  90                  95

Thr His Val Pro Pro Thr Phe Gly Gln Gly Thr Lys Leu Glu Ile Lys
            100                 105                 110

<210> SEQ ID NO 71
<211> LENGTH: 115
<212> TYPE: PRT
<213> ORGANISM: Artificial Sequence
<220> FEATURE:
<223> OTHER INFORMATION: modified antibody fragment

<400> SEQUENCE: 71

Gln Val Gln Leu Val Gln Ser Gly Ala Glu Val Lys Lys Pro Gly Ala
 1               5                  10                  15

Ser Val Thr Val Ser Cys Lys Ala Ser Gly Tyr Thr Phe Thr Asp Tyr
                 20                  25                  30

Glu Met His Trp Ile Arg Gln Pro Pro Gly Glu Gly Leu Glu Trp Ile
             35                  40                  45

Gly Ala Ile Asp Pro Lys Thr Gly Asp Thr Ala Tyr Ser Glu Ser Phe
     50                  55                  60

Gln Asp Arg Val Thr Leu Thr Ala Asp Lys Ser Thr Ser Thr Ala Tyr
 65                  70                  75                  80

Met Glu Leu Ser Ser Leu Thr Ser Glu Asp Thr Ala Val Tyr Tyr Cys
                 85                  90                  95

Thr Arg Phe Tyr Ser Tyr Thr Tyr Trp Gly Gln Gly Thr Leu Val Thr
            100                 105                 110

Val Ser Ser
        115
```

```
<210> SEQ ID NO 72
<211> LENGTH: 112
<212> TYPE: PRT
<213> ORGANISM: Artificial Sequence
<220> FEATURE:
<223> OTHER INFORMATION: modified antibody fragment

<400> SEQUENCE: 72
```

Asp Ile Val Met Thr Gln Ser Pro Leu Ser Leu Pro Val Thr Pro Gly
1               5                   10                  15

Glu Pro Ala Ser Ile Ser Cys Gln Ala Ser Gln Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

```
<210> SEQ ID NO 73
<211> LENGTH: 112
<212> TYPE: PRT
<213> ORGANISM: Artificial Sequence
<220> FEATURE:
<223> OTHER INFORMATION: modified antibody fragment

<400> SEQUENCE: 73
```

Asp Ile Val Met Thr Gln Ser Pro Leu Ser Leu Pro Val Thr Pro Gly
1               5                   10                  15

Glu Pro Ala Ser Ile Ser Cys Gln Ala Ser Gln Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Val Glu Ile Glu
            100                 105                 110

```
<210> SEQ ID NO 74
<211> LENGTH: 330
<212> TYPE: PRT
<213> ORGANISM: homo sapiens

<400> SEQUENCE: 74
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 75
<211> LENGTH: 326
<212> TYPE: PRT
<213> ORGANISM: homo sapiens

<400> SEQUENCE: 75

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

```
Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 76
<211> LENGTH: 377
<212> TYPE: PRT
<213> ORGANISM: homo sapiens

<400> SEQUENCE: 76

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140
```

```
Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
            165                 170                 175

Pro Lys Asp Thr Leu Met Ile Ser Arg Thr Pro Glu Val Thr Cys Val
        180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
        210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
            245                 250                 255

Ala Leu Pro Ala Pro Ile Glu Lys Thr Ile Ser Lys Thr Lys Gly Gln
        260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
            325                 330                 335

Tyr Ser Lys Leu Thr Val Asp Lys Ser Arg Trp Gln Gln Gly Asn Ile
        340                 345                 350

Phe Ser Cys Ser Val Met His Glu Ala Leu His Asn Arg Phe Thr Gln
        355                 360                 365

Lys Ser Leu Ser Leu Ser Pro Gly Lys
        370                 375

<210> SEQ ID NO 77
<211> LENGTH: 327
<212> TYPE: PRT
<213> ORGANISM: homo sapiens

<400> SEQUENCE: 77

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140
```

```
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 78
<211> LENGTH: 374
<212> TYPE: PRT
<213> ORGANISM: homo sapiens

<400> SEQUENCE: 78

Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
                20                  25                  30

Val Phe Gln Glu Glu Thr Val Thr Leu His Cys Glu Val Leu His Leu
            35                  40                  45

Pro Gly Ser Ser Ser Thr Gln Trp Phe Leu Asn Gly Thr Ala Thr Gln
        50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190
```

```
Val Leu Asn Ala Ser Val Thr Ser Pro Leu Leu Glu Gly Asn Leu Val
            195                 200                 205

Thr Leu Ser Cys Glu Thr Lys Leu Leu Gln Arg Pro Gly Leu Gln
210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
            245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
            275                 280                 285

Val Trp Phe His Val Leu Phe Tyr Leu Ala Val Gly Ile Met Phe Leu
            290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
            325                 330                 335

Val Ile Ser Ser Leu Gln Glu Asp Arg His Leu Glu Glu Leu Lys
            340                 345                 350

Cys Gln Glu Gln Lys Glu Glu Gln Leu Gln Glu Gly Val His Arg Lys
            355                 360                 365

Glu Pro Gln Gly Ala Thr
            370

<210> SEQ ID NO 79
<211> LENGTH: 316
<212> TYPE: PRT
<213> ORGANISM: homo sapiens

<400> SEQUENCE: 79

Met Thr Met Glu Thr Gln Met Ser Gln Asn Val Cys Pro Arg Asn Leu
1               5                   10                  15

Trp Leu Leu Gln Pro Leu Thr Val Leu Leu Leu Leu Ala Ser Ala Asp
            20                  25                  30

Ser Gln Ala Ala Pro Lys Ala Val Leu Lys Leu Glu Pro Pro Trp
            35                  40                  45

Ile Asn Val Leu Gln Glu Asp Ser Val Thr Leu Thr Cys Gln Gly Ala
            50                  55                  60

Arg Ser Pro Glu Ser Asp Ser Ile Gln Trp Phe His Asn Gly Asn Leu
65                  70                  75                  80

Ile Pro Thr His Thr Gln Pro Ser Tyr Arg Phe Lys Ala Asn Asn Asn
            85                  90                  95

Asp Ser Gly Glu Tyr Thr Cys Gln Thr Gly Gln Thr Ser Leu Ser Asp
            100                 105                 110

Pro Val His Leu Thr Val Leu Ser Glu Trp Leu Val Leu Gln Thr Pro
            115                 120                 125

His Leu Glu Phe Gln Glu Gly Glu Thr Ile Met Leu Arg Cys His Ser
            130                 135                 140

Trp Lys Asp Lys Pro Leu Val Lys Val Thr Phe Phe Gln Asn Gly Lys
145                 150                 155                 160

Ser Gln Lys Phe Ser His Leu Asp Pro Thr Phe Ser Ile Pro Gln Ala
            165                 170                 175

Asn His Ser His Ser Gly Asp Tyr His Cys Thr Gly Asn Ile Gly Tyr
            180                 185                 190
```

-continued

```
Thr Leu Phe Ser Ser Lys Pro Val Thr Ile Thr Val Gln Val Pro Ser
            195                 200                 205

Met Gly Ser Ser Ser Pro Met Gly Val Ile Val Ala Val Val Ile Ala
        210                 215                 220

Thr Ala Val Ala Ala Ile Val Ala Ala Val Val Ala Leu Ile Tyr Cys
225                 230                 235                 240

Arg Lys Lys Arg Ile Ser Ala Asn Ser Thr Asp Pro Val Lys Ala Ala
                245                 250                 255

Gln Phe Glu Pro Pro Gly Arg Gln Met Ile Ala Ile Arg Lys Arg Gln
            260                 265                 270

Leu Glu Glu Thr Asn Asn Asp Tyr Glu Thr Ala Asp Gly Gly Tyr Met
        275                 280                 285

Thr Leu Asn Pro Arg Ala Pro Thr Asp Asp Asp Lys Asn Ile Tyr Leu
    290                 295                 300

Thr Leu Pro Pro Asn Asp His Val Asn Ser Asn Asn
305                 310                 315

<210> SEQ ID NO 80
<211> LENGTH: 291
<212> TYPE: PRT
<213> ORGANISM: homo sapiens

<400> SEQUENCE: 80

Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
            20                  25                  30

Ala Val Leu Phe Leu Ala Pro Val Ala Gly Thr Pro Ala Ala Pro Pro
        35                  40                  45

Lys Ala Val Leu Lys Leu Glu Pro Gln Trp Ile Asn Val Leu Gln Glu
    50                  55                  60

Asp Ser Val Thr Leu Thr Cys Arg Gly Thr His Ser Pro Glu Ser Asp
65                  70                  75                  80

Ser Ile Gln Trp Phe His Asn Gly Asn Leu Ile Pro Thr His Thr Gln
                85                  90                  95

Pro Ser Tyr Arg Phe Lys Ala Asn Asn Asn Asp Ser Gly Glu Tyr Thr
            100                 105                 110

Cys Gln Thr Gly Gln Thr Ser Leu Ser Asp Pro Val His Leu Thr Val
        115                 120                 125

Leu Ser Glu Trp Leu Val Leu Gln Thr Pro His Leu Glu Phe Gln Glu
    130                 135                 140

Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Lys Phe Ser Arg
                165                 170                 175

Ser Asp Pro Asn Phe Ser Ile Pro Gln Ala Asn His Ser His Ser Gly
            180                 185                 190

Asp Tyr His Cys Thr Gly Asn Ile Gly Tyr Thr Leu Tyr Ser Ser Lys
        195                 200                 205

Pro Val Thr Ile Thr Val Gln Ala Pro Ser Ser Pro Met Gly Ile
    210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Asn Pro
                245                 250                 255
```

```
Thr Asn Pro Asp Glu Ala Asp Lys Val Gly Ala Glu Asn Thr Ile Thr
            260                 265                 270

Tyr Ser Leu Leu Met His Pro Asp Ala Leu Glu Glu Pro Asp Gln
        275                 280                 285

Asn Arg Ile
        290

<210> SEQ ID NO 81
<211> LENGTH: 254
<212> TYPE: PRT
<213> ORGANISM: homo sapiens

<400> SEQUENCE: 81

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ser Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 82
<211> LENGTH: 233
<212> TYPE: PRT
<213> ORGANISM: homo sapiens

<400> SEQUENCE: 82

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30
```

```
Gln Trp Tyr Ser Val Leu Glu Lys Asp Ser Val Thr Leu Lys Cys Gln
             35                  40                  45

Gly Ala Tyr Ser Pro Glu Asp Asn Ser Thr Gln Trp Phe His Asn Glu
 50                  55                  60

Ser Leu Ile Ser Ser Gln Ala Ser Ser Tyr Phe Ile Asp Ala Ala Thr
 65                  70                  75                  80

Val Asn Asp Ser Gly Glu Tyr Arg Cys Gln Thr Asn Leu Ser Thr Leu
                 85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
            195                 200                 205

Val Ser Phe Cys Leu Val Met Val Leu Leu Phe Ala Val Asp Thr Gly
            210                 215                 220

Leu Tyr Phe Ser Val Lys Thr Asn Ile
225                 230

<210> SEQ ID NO 83
<211> LENGTH: 140
<212> TYPE: PRT
<213> ORGANISM: Mus musculus

<400> SEQUENCE: 83

Met Glu Trp Ile Trp Ile Phe Leu Phe Ile Leu Ser Gly Thr Ala Gly
 1               5                  10                  15

Val Gln Ser Gln Val Gln Leu Gln Gln Ser Gly Ala Glu Leu Ala Arg
                 20                  25                  30

Pro Gly Ala Ser Val Lys Leu Ser Cys Arg Ala Ser Gly Tyr Thr Phe
             35                  40                  45

Thr Ser Tyr Gly Ile Ser Trp Met Met Gln Arg Thr Gly Gln Gly Leu
 50                  55                  60

Glu Trp Ile Gly Glu Ile Tyr Pro Arg Ser Gly Ile Thr Tyr Tyr Asn
 65                  70                  75                  80

Glu Lys Phe Lys Gly Lys Ala Thr Leu Thr Ala Asp Lys Ser Ser Ser
                 85                  90                  95

Thr Ala Tyr Met Gln Leu Ser Ser Leu Thr Ser Glu Asp Ser Ala Val
            100                 105                 110

Tyr Phe Cys Ala Arg Asp Val Ser Asp Gly Tyr Leu Phe Pro Tyr Trp
            115                 120                 125

Gly Gln Gly Thr Leu Val Thr Val Ser Ala Ala Lys
            130                 135                 140

<210> SEQ ID NO 84
<211> LENGTH: 129
<212> TYPE: PRT
<213> ORGANISM: Mus musculus
```

<400> SEQUENCE: 84

Met Ser Val Pro Thr Gln Val Leu Gly Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Thr Ser Glu Asn
        35                  40                  45

Ile Tyr Ser Tyr Leu Ala Trp Tyr Gln Lys Gln Gly Lys Ser Pro
    50                  55                  60

Gln Leu Leu Val Tyr Asn Ala Lys Thr Leu Pro Glu Gly Val Pro Ser
65                  70                  75                  80

Arg Phe Ser Gly Ser Gly Ser Gly Thr Gln Phe Ser Leu Lys Ile Asn
                85                  90                  95

Ser Leu Gln Pro Glu Asp Phe Gly Ser Tyr Tyr Cys Gln His His Tyr
            100                 105                 110

Gly Thr Pro Pro Thr Phe Gly Gly Gly Thr Lys Leu Glu Ile Lys Arg
        115                 120                 125

Ala

<210> SEQ ID NO 85
<211> LENGTH: 139
<212> TYPE: PRT
<213> ORGANISM: Mus musculus

<400> SEQUENCE: 85

Met Asn Phe Gly Leu Ser Leu Ile Phe Leu Ala Leu Ile Leu Lys Gly
1               5                   10                  15

Val Gln Cys Glu Val Gln Leu Val Glu Ser Gly Gly Asp Val Val Arg
            20                  25                  30

Pro Gly Gly Ser Leu Lys Leu Ser Cys Ala Ala Ser Gly Phe Thr Phe
        35                  40                  45

Ser Ser Tyr Gly Met Ser Trp Val Arg Gln Leu Pro Asp Lys Arg Leu
    50                  55                  60

Glu Trp Val Ala Ser Val Gly Asn Gly Gly Ser Tyr Arg Tyr Tyr Pro
65                  70                  75                  80

Glu Asn Leu Lys Gly Arg Phe Thr Ile Ser Arg Asp Asn Thr Lys Asn
                85                  90                  95

Thr Leu Tyr Leu Gln Ile Ser Gly Leu Lys Ser Glu Asp Thr Ala Ile
            100                 105                 110

Tyr Tyr Cys Ala Arg Arg Gly Ala Phe Pro Tyr Phe Asp Val Trp Gly
        115                 120                 125

Ala Gly Thr Thr Val Thr Val Ser Ser Ala Lys
    130                 135

<210> SEQ ID NO 86
<211> LENGTH: 129
<212> TYPE: PRT
<213> ORGANISM: Mus musculus

<400> SEQUENCE: 86

Met Ser Val Pro Thr Gln Val Leu Gly Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Thr Ser Glu Asn
        35                  40                  45

```
Ile Tyr Ser Tyr Leu Ala Trp Tyr Gln Gln Lys Gln Gly Lys Ser Pro
         50                  55                  60

Gln Leu Leu Val Tyr Asn Ala Lys Thr Leu Pro Glu Gly Val Pro Ser
 65                  70                  75                  80

Arg Phe Ser Gly Ser Gly Ser Gly Thr Gln Phe Ser Leu Lys Ile Asn
                 85                  90                  95

Ser Leu Gln Pro Glu Asp Phe Gly Ser Tyr Tyr Cys Gln His His Tyr
                100                 105                 110

Gly Thr Pro Pro Thr Phe Gly Gly Thr Lys Leu Glu Ile Lys Arg
                115                 120                 125

Ala

<210> SEQ ID NO 87
<211> LENGTH: 136
<212> TYPE: PRT
<213> ORGANISM: Mus musculus

<400> SEQUENCE: 87

Met Arg Val Leu Ile Leu Leu Trp Leu Phe Thr Ala Phe Pro Gly Ile
 1               5                  10                  15

Leu Ser Asp Val Gln Leu Gln Glu Ser Gly Pro Gly Leu Val Lys Pro
                 20                  25                  30

Ser Gln Ser Leu Ser Leu Thr Cys Thr Val Thr Gly Tyr Ser Ile Thr
             35                  40                  45

Ser Asp Ser Ala Trp Asn Trp Ile Arg Gln Phe Pro Gly Asn Lys Leu
         50                  55                  60

Glu Trp Met Ala Tyr Ile Met Tyr Ser Gly Ile Thr Ser Tyr Asn Pro
 65                  70                  75                  80

Ser Leu Lys Ser Arg Ile Ser Ile Thr Arg Asp Thr Ala Lys Asn Gln
                 85                  90                  95

Phe Phe Leu Gln Leu Asn Ser Val Thr Thr Glu Asp Ser Ala Thr Tyr
                100                 105                 110

Tyr Cys Ser Arg Gly Tyr Trp Tyr Phe Asp Val Trp Gly Ala Gly Thr
            115                 120                 125

Thr Val Thr Val Ser Ser Ala Lys
        130                 135

<210> SEQ ID NO 88
<211> LENGTH: 129
<212> TYPE: PRT
<213> ORGANISM: Mus musculus

<400> SEQUENCE: 88

Met Asp Phe Gln Val Gln Ile Phe Ser Phe Leu Leu Ile Ser Ala Ser
 1               5                  10                  15

Val Ile Met Ser Arg Gly Gln Ile Val Leu Thr Gln Ser Pro Ala Ile
                 20                  25                  30

Met Ser Ala Ser Leu Gly Glu Glu Ile Thr Leu Thr Cys Ser Ala Ser
             35                  40                  45

Ser Ser Val Ser Tyr Met His Trp Tyr Gln Gln Lys Ser Gly Thr Ser
         50                  55                  60

Pro Lys Leu Leu Ile Tyr Ser Thr Ser Ile Leu Ala Ser Gly Val Pro
 65                  70                  75                  80

Ser Arg Phe Ser Gly Ser Gly Ser Gly Thr Phe Tyr Ser Leu Thr Ile
                 85                  90                  95
```

```
Ser Ser Val Glu Ala Glu Asp Ala Ala Asp Tyr Tyr Cys Leu Gln Trp
            100                 105                 110

Ile Thr Tyr Arg Thr Phe Gly Gly Gly Thr Lys Leu Glu Ile Lys Arg
        115                 120                 125

Ala

<210> SEQ ID NO 89
<211> LENGTH: 138
<212> TYPE: PRT
<213> ORGANISM: Mus musculus

<400> SEQUENCE: 89

Met Cys Trp Ser Cys Ile Ile Leu Phe Leu Leu Ala Thr Ala Ala Arg
1               5                   10                  15

Val His Ser Gln Val Gln Leu Gln Gln Ser Gly Ala Glu Leu Val Gly
            20                  25                  30

Pro Gly Ala Ser Val Lys Ile Ser Cys Lys Ala Phe Gly Tyr Thr Phe
        35                  40                  45

Thr Asn His His Ile Asn Trp Val Lys Gln Arg Pro Gly Gln Gly Leu
    50                  55                  60

Asp Trp Ile Gly Tyr Ile Asn Pro Tyr Asn Asp Tyr Thr Asn Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Ser Ser Leu Thr Ser Glu Asp Ser Ala Val
            100                 105                 110

Tyr Tyr Cys Ala Arg Ser Asp Pro Ala Trp Phe Ala Tyr Trp Gly Gln
        115                 120                 125

Gly Thr Leu Val Thr Val Ser Ala Ala Lys
    130                 135

<210> SEQ ID NO 90
<211> LENGTH: 129
<212> TYPE: PRT
<213> ORGANISM: Mus musculus

<400> SEQUENCE: 90

Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Ser Ser Leu Ser
            20                  25                  30

Ala Ser Leu Gly Gly Lys Val Thr Ile Thr Cys Lys Ala Ser Gln Asp
        35                  40                  45

Ile Asn Lys Asn Ile Ala Trp Tyr Gln His Lys Pro Gly Lys Gly Pro
    50                  55                  60

Arg Leu Leu Ile Trp Tyr Thr Tyr Thr Leu Gln Pro Gly Ile Pro Ser
65                  70                  75                  80

Arg Phe Ser Gly Ser Gly Ser Gly Arg Asp Tyr Ser Phe Ser Ile Ser
                85                  90                  95

Asn Leu Glu Pro Glu Asp Ile Ala Thr Tyr Tyr Cys Leu Gln Tyr Asp
            100                 105                 110

Asn Leu Pro Phe Thr Phe Gly Thr Gly Thr Lys Leu Glu Ile Lys Arg
        115                 120                 125

Ala
```

GPC3-TARGETING DRUG WHICH IS ADMINISTERED TO PATIENT RESPONSIVE TO GPC3-TARGETING DRUG THERAPY

CROSS REFERENCE TO RELATED APPLICATIONS

This application is a National Stage of International Application No. PCT/JP2013/007529 filed Dec. 24, 2013, claiming priority based on Japanese Patent Application No. 2012-280304 filed Dec. 21, 2012, the contents of all of which are incorporated herein by reference in their entirety.

TECHNICAL FIELD

The present invention provides a method for determining the efficacy of GPC3-targeting drug therapy for cancer in a patient or determining the continuation of GPC3-targeting drug therapy for a patient. The present invention also provides a GPC3-targeting drug or a preparation which is to be further administered to a patient for the efficacy of the GPC3-targeting drug therapy has been determined or the continuation of the GPC3-targeting drug therapy has been determined.

BACKGROUND ART

Hepatocellular cancer is reportedly the fifth leading cause of cancer deaths worldwide, accounting for approximately 600,000 deaths each year (Non Patent Literature 1). Most patients with hepatocellular cancer die within 1 year after being diagnosed with the disease. Unfortunately, hepatocellular cancer cases are frequently diagnosed at a late stage which rarely responds to curative therapies. Still, medical treatments including chemotherapy, chemoembolization, ablation, and proton beam therapy are insufficiently effective for such patients. Many patients exhibit recurrence of the disease with vascular invasion and multiple intrahepatic metastases, which rapidly progresses to the advanced stage. Their 5-year survival rates are only 7% (Non Patent Literature 2). Patients with hepatocellular cancer amenable to the resection of local foci have relatively good prognosis, though their 5-year survival rates still remain at a level of 15% and 39% (Non Patent Literature 3). Thus, there has been a demand in the art for novel therapy for such a malignant disease hepatocellular cancer.

Hepatocellular cancer is reportedly responsible for more than 90% of primary liver cancer cases in Japan. Medical methods for treating such hepatocellular cancer include, for example, chemotherapy-based transcatheter arterial embolization (TAE) therapy, which involves inducing the selective necrosis of the hepatocellular cancer by the injection of a mixture of an oil-based contrast medium (Lipiodol), an anticancer agent, and an obstructing substance (Gelfoam) into the hepatic artery (which serves as a nutrient supply pathway to the tumor) resulting in the obstruction of the nutrient artery. In addition, invasive approaches are used, such as percutaneous ethanol injection, percutaneous microwave coagulation therapy, and radiofrequency ablation. Also, clinical trials have been conducted on systemic chemotherapy using chemotherapeutic agents such as fluorouracil (5-FU), uracil-tegafur (UFT), mitomycin C (MMC), mitoxantrone (DHAD), adriamycin (ADR), epirubicin (EPI), and cisplatin (CDDP) either alone or in combination with interferon (IFN) (Non Patent Literature 4).

Meanwhile, an orally active form of sorafenib (Nexavar, BAY43-9006) has been approved, which is more advantageously effective than the chemotherapeutic agents described above in such a way that this agent blocks the growth of cancer cells by inhibiting Raf kinase in the Raf/MEK/ERK signal transduction while the agent exerts antiangiogenic effects by targeting VEGFR-2, VEGFR-3, and PDGFR-$\beta$ tyrosine kinases. The efficacy of sorafenib has been studied in two phase-III multicenter placebo-controlled trials (Sorafenib HCC Assessment Randomized Protocol (SHARP) trial and Asia-Pacific trial) targeting advanced hepatocellular cancer. Sorafenib was confirmed to prolong survival durations, with HR of 0.68, in both of these trials. In the SHARP trial, sorafenib prolonged the survival duration to 10.7 months versus 7.9 months with the placebo. In the Asian trial, this agent prolonged the survival duration to 6.5 months versus 4.2 months with the placebo. The agent, however, had a low objective response rate and showed no prolongation of a time to symptomatic progression, though the agent prolonged a time to tumor progression (5.5 months versus 2.8 months in the European and American trial and 2.8 months versus 1.4 months in the Asian trial) on the images. The Asian cohorts exhibited a short duration of life prolongation, which is probably because their treatments were started at a slightly later stage during the disease process in the Asian region compared with Europe and the United States (Non Patent Literatures 5 and 6).

As liver cancer progresses, its specific symptoms associated with liver dysfunction are generally observed, such as anorexia, weight loss, general malaise, palpable right hypochondrial mass, right hypochondrial pain, sense of abdominal fullness, fever, and jaundice. The chemotherapeutic agents (e.g., sorafenib), however, have complications to be overcome, including their inherent adverse reactions such as diarrhea or constipation, anemia, suppression of the immune system to cause infection or sepsis (with lethal severity), hemorrhage, cardiac toxicity, hepatic toxicity, renal toxicity, anorexia, and weight loss.

Although particular early-stage symptoms are not initially observed in liver cancer, its specific symptoms associated with liver dysfunction, such as anorexia, weight loss, general malaise, palpable right hypochondrial mass, right hypochondrial pain, sense of abdominal fullness, fever, and jaundice, are generally observed with progression of the liver cancer. According to clinical observation, such symptoms are enhanced by use of the chemotherapeutic agents. For example, anorexia in a patient with detectable liver cancer cells and symptoms such as weight loss associated with or independent of the anorexia may be more enhanced by the administration of the chemotherapeutic agents to the patient than without the use of the chemotherapeutic agents. In some cases, the use of the chemotherapeutic agents must be discontinued for the patient having such symptoms. These enhanced symptoms are impediments to treatments with the chemotherapeutic agents. Thus, there has been a demand for the establishment of excellent therapy from the viewpoint of, for example, improving therapeutic effects or improving QOL of patients to be treated.

Glypican 3 (GPC3) is frequently expressed at a high level in liver cancer and as such, seems to be useful in the identification of its functions in liver cancer or as a therapeutic or diagnostic target of liver cancer.

Under the circumstances described above, drugs are under development with GPC3 as a therapeutic target of liver cancer. A liver cancer drug comprising an anti-GPC3 antibody as an active ingredient has been developed, the antibody having antibody-dependent cellular cytotoxicity (hereinafter, referred to as "ADCC") activity and/or complement-dependent cytotoxicity (hereinafter, referred to as "CDC")

activity against cells expressing GPC3 (Patent Literature 1). Also, a GPC3-targeting drug comprising a humanized anti-GPC3 antibody having ADCC activity and CDC activity as an active ingredient has been developed (Patent Literature 2). Further GPC3-targeting drugs have been developed, which comprise a humanized anti-GPC3 antibody with enhanced ADCC activity (Patent Literatures 3 and 4) or an anti-GPC3 antibody having ADCC activity and CDC activity as well as improved plasma dynamics (Patent Literature 5). These anti-GPC3 antibodies in combination therapy with the chemotherapeutic agents such as sorafenib have been found to attenuate the adverse reactions, for example, brought about by the sole therapy of the chemotherapeutic agents (e.g., sorafenib) and also found to exhibit synergistic effects based on these agents (Patent Literature 6). Accordingly, excellent methods for treating liver cancer are in the process of being established using GPC3-targeting drugs as the nucleus from the viewpoint of, for example, improving therapeutic effects or improving QOL of patients to be treated.

Meanwhile, GPC3-targeting methods for diagnosing liver cancer are also under development. GPC3 is known to be expressed on cell surface and processed, at the particular site, by convertase, phospholipase D, Notum or unspecified mechanism (Non Patent Literature 7 and 8) during or after expression on cell surface. By use of such a phenomenon, a diagnostic agent or a diagnostic method for liver cancer has been developed, which involves an antibody capable of binding to an epitope in a soluble form of GPC3 secreted into the plasma of a patient after processing (Patent Literature 7). Also, a diagnostic agent or a diagnostic method for liver cancer has been developed, which involves an antibody capable of binding to an epitope in an anchored form of GPC3 still existing on cell surface after processing in a tissue preparation or the like isolated from a patient (Patent Literature 8). These diagnostic agents or diagnostic methods, however, are means for detecting the presence of liver cancer in a patient to be tested. Neither a method for determining the efficacy of GPC3-targeting drug therapy for a patient treated with the GPC3-targeting drug therapy nor a method for determining the continuation of GPC3-targeting drug therapy for the patient has been known yet.

References cited herein are as listed below. The contents described in these literatures are incorporated herein by reference in their entirety. It should be noted that none of these literatures are admitted to be the prior art to the present invention.

CITATION LIST

Patent Literature

[Patent Literature 1] WO2003/000883
[Patent Literature 2] WO2006/006693
[Patent Literature 3] WO2006/046751
[Patent Literature 4] WO2007/047291
[Patent Literature 5] WO2009/041062
[Patent Literature 6] WO2009/122667
[Patent Literature 7] WO2004/038420
[Patent Literature 8] WO2009/116659

Non Patent Literature

[Non Patent Literature 1] Llovet J M, Burroughs A, Bruix J; Lancet (2003), 362, 1907-17
[Non Patent Literature 2] Bosch F X, Ribes J, Cleries R; Gastroenterology (2004), 127, S5-16
[Non Patent Literature 3] Takenaka K, Kawahara N, Yamamoto K, Kajiyama K, Maeda T, Itasaka H, Shirabe K, Nishizaki T, Yanaga K, Sugimachi K; Arch Surg (1996), 131, 71-6
[Non Patent Literature 4] Yeo W, Mok T S, Zee B, Leung T W, Lai P B, Lau W Y, Koh J, Mo F K, Yu S C, Chan A T, Hui P, Ma B, Lam K C, Ho W M, Wong H T, Tang A, Johnson P J; J Natl Cancer Inst (2005), 97, 1532-8
[Non Patent Literature 5] Llovet J, Ricci S, Mazzaferro V, Hilgard P, Gane E, et al. Sorafenib in advanced hepatocellular carcinoma. New Eng. J. Med. (2008) 359, 378-90
[Non Patent Literature 6] Cheng A L, Chen Z, Tsao C J, Qin S, Kim J S, et al. Efficacy and safety of sorefanib in patients in the Asia-Pacific region with advanced hepatocellular carcinoma: a phase III randomized, double-blind, placebo-controlled trial. Lancet Oncol. (2009) 10, 25-34
[Non Patent Literature 7] De Cat B, Muyldermans S-Y, Coomans C, Degeest G, Vanderschueren B, et al. Processing by proprotein convertases is required for glypican-3 modulation of cell survival, Wnt signaling, and gastrulation movements. J. Cell. Biol. (2003) 163, 625-635
[Non Patent Literature 8] Traister A, Shi W and Filmus J. Mammalian Notum induces the release of glypicans and other GPI-anchored proteins from the cell surface. Biochem. J. (2008) 410, 503-511

SUMMARY OF INVENTION

Technical Problem

The present invention has been made in light of the situations as described above, and an object of the present invention is to provide a method for determining the efficacy of GPC3-targeting drug therapy for a patient treated with the GPC3-targeting drug therapy or determining the continuation of GPC3-targeting drug therapy for the patient. Another object of the present invention is to provide a GPC3-targeting drug or a preparation which is to be further administered to a patient for which the efficacy of the GPC3-targeting drug therapy has been determined or the continuation of the GPC3-targeting drug therapy has been determined.

Solution to Problem

The present inventors have conducted diligent studies under the situations as described above and consequently created a method comprising monitoring a concentration of free GPC3 in a biological sample isolated from a patient treated with GPC3-targeting drug therapy, wherein when the concentration of free GPC3 is a predetermined value or when the concentration of free GPC3 has been increased as a result of receiving the GPC3-targeting drug therapy, the efficacy of the GPC3-targeting drug therapy is determined or the continuation of the GPC3-targeting drug therapy is determined. The present inventors have also created a GPC3-targeting drug or a preparation which is to be further administered to a patient for which the efficacy of the GPC3-targeting drug therapy has been determined or the continuation of the GPC3-targeting drug therapy has been determined. It has been expected from the previous findings that the concentration of free GPC3 detected in plasma is decreased over time with the continuation of the treatment, if the GPC3-targeting drug therapy has efficacy. Surprisingly, the present inventors have found that the concentration of free GPC3 is stabilized or increased, rather than decreased, in plasma isolated from a patient with stable disease that may respond to the GPC3-targeting drug therapy.

More specifically, the present invention provides the following aspects:

[1] a method for determining the efficacy of GPC3-targeting drug therapy for cancer in a patient or determining the continuation of GPC3-targeting drug therapy for a patient, comprising monitoring a concentration of free GPC3 in a biological sample isolated from the patient before the start of GPC3-targeting drug therapy and/or the patient treated with the GPC3-targeting drug therapy, wherein when the concentration of free GPC3 is a predetermined value, the efficacy of the GPC3-targeting drug therapy is determined or the continuation of the GPC3-targeting drug therapy is determined,

[2] the method according to [1], wherein the concentration of free GPC3 is a concentration in a whole blood sample, a plasma sample, or a serum sample isolated from the patient,

[3] the method according to [2], wherein the concentration of free GPC3 in the biological sample isolated from the patient is a concentration in the plasma sample or the serum sample,

[4] the method according to any of [1] to [3], wherein the predetermined value of free GPC3 ranges from 0.1 ng/mL to 100 ng/mL,

[5] the method according to any of [1] to [4], wherein the concentration of free GPC3 is measured using an immunological method,

[6] the method according to any of [1] to [5], wherein the concentration of free GPC3 is larger than that in a biological sample isolated before the start of the GPC3-targeting drug therapy from the patient,

[7] the method according to any of [1] to [6], wherein the patient shows high expression of GPC3 in an immunohistochemical staining score,

[8] the method according to any of [1] to [7], wherein the cancer is liver cancer,

[9] the method according to any of [1] to [8], wherein the GPC3-targeting drug is administered to achieve a blood trough level of 200 µg/ml or higher in the cancer patient,

[10] the method according to any of [1] to [9], wherein the GPC3-targeting drug comprises an anti-GPC3 antibody as an active ingredient,

[11] the method according to [10], wherein the anti-GPC3 antibody has antibody-dependent cellular cytotoxicity (ADCC) activity and/or complement-dependent cytotoxicity (CDC) activity,

[12] the method according to [10] or [11], wherein the anti-GPC3 antibody is an anti-GPC3 chimeric antibody or a humanized anti-GPC3 antibody comprising any of the following (1) to (5):

(1) heavy chain CDR1, heavy chain CDR2, and heavy chain CDR3 represented by SEQ ID NOs: 4, 5, and 6, respectively, and light chain CDR1, light chain CDR2, and light chain CDR3 represented by SEQ ID NOs: 7, 8, and 9, respectively;

(2) heavy chain CDR1, heavy chain CDR2, and heavy chain CDR3 represented by SEQ ID NOs: 12, 13, and 14, respectively, and light chain CDR1, light chain CDR2, and light chain CDR3 represented by SEQ ID NOs: 15, 16, and 17, respectively;

(3) heavy chain CDR1, heavy chain CDR2, and heavy chain CDR3 represented by SEQ ID NOs: 20, 21, and 22, respectively, and light chain CDR1, light chain CDR2, and light chain CDR3 represented by SEQ ID NOs: 23, 24, and 25, respectively;

(4) heavy chain CDR1, heavy chain CDR2, and heavy chain CDR3 represented by SEQ ID NOs: 28, 29, and 30, respectively, and light chain CDR1, light chain CDR2, and light chain CDR3 represented by SEQ ID NOs: 31, 32, and 33, respectively; and (5) heavy chain CDR1, heavy chain CDR2, and heavy chain CDR3 represented by SEQ ID NOs: 36, 37, and 38, respectively, and light chain CDR1, light chain CDR2, and light chain CDR3 represented by SEQ ID NOs: 39, 40, and 41, respectively,

[13] The method according to any of [10] to [12], wherein the anti-GPC3 antibody comprises any of the following (1) to (6):

(1) a heavy chain variable region selected from the group of heavy chain variable regions represented by SEQ ID NOs: 44, 45, 46, 47, 48, 49, and 50 and a light chain variable region represented by SEQ ID NO: 51;

(2) a heavy chain variable region selected from the group of heavy chain variable regions represented by SEQ ID NOs: 44, 45, 46, 47, 48, 49, and 50 and a light chain variable region selected from the group of light chain variable regions represented by SEQ ID NOs: 52, 53, 54, 55, 56, 57, 58, 59, 60, 61, 62, 63, 64, 65, and 66;

(3) a heavy chain variable region represented by SEQ ID NO: 67 and a light chain variable region represented by SEQ ID NO: 68;

(4) a heavy chain variable region represented by SEQ ID NO: 69 and a light chain variable region represented by SEQ ID NO: 70;

(5) a heavy chain variable region represented by SEQ ID NO: 71 and a light chain variable region represented by SEQ ID NO: 72; and (6) a heavy chain variable region represented by SEQ ID NO: 71 and a light chain variable region represented by SEQ ID NO: 73,

[14] the method according to [10], wherein the GPC3-targeting drug comprises an anti-GPC3 antibody conjugated with a cytotoxic substance,

[15] a GPC3-targeting drug which is to be administered to a cancer patient having a predetermined value of a concentration of free GPC3 in a biological sample isolated from the cancer patient before the start of GPC3-targeting drug therapy,

[16] a GPC3-targeting drug which is to be further administered to a cancer patient having a predetermined value of a concentration of free GPC3 in a biological sample isolated from the cancer patient after the start of GPC3-targeting drug therapy,

[17] the drug according to [15] or [16], wherein the concentration of free GPC3 is a concentration in a whole blood sample, a plasma sample, or a serum sample isolated from the cancer patient,

[18] the drug according to [17], wherein the concentration of free GPC3 in the biological sample isolated from the cancer patient is a concentration in the plasma sample or the serum sample,

[19] the drug according to any of [15] to [18], wherein the predetermined value of free GPC3 ranges from 0.1 ng/mL to 60 ng/mL,

[20] the drug according to any of [15] to [19], wherein the concentration of free GPC3 is measured using an immunological method,

[21] the drug according to any of [15] to [20], wherein the concentration of free GPC3 has been increased as a result of receiving the GPC3-targeting drug therapy,

[22] the drug according to any of [15] to [21], wherein the patient shows high expression of GPC3 in an immunohistochemical staining score,

[23] the drug according to any of [15] to [22], wherein the cancer patient is a liver cancer patient,

[24] the drug according to any of [15] to [23], wherein the GPC3-targeting drug is administered to achieve a blood trough level of 200 μg/ml or higher in the cancer patient,

[25] the drug according to any of [15] to [24], wherein the GPC3-targeting drug comprises an anti-GPC3 antibody as an active ingredient,

[26] the drug according to [25], wherein the anti-GPC3 antibody has antibody-dependent cellular cytotoxicity (ADCC) activity and/or complement-dependent cytotoxicity (CDC) activity,

[27] the drug according to [25] or [26], wherein the anti-GPC3 antibody is an anti-GPC3 chimeric antibody or a humanized anti-GPC3 antibody comprising any of the following (1) to (5):

(1) heavy chain CDR1, heavy chain CDR2, and heavy chain CDR3 represented by SEQ ID NOs: 4, 5, and 6, respectively, and light chain CDR1, light chain CDR2, and light chain CDR3 represented by SEQ ID NOs: 7, 8, and 9, respectively;

(2) heavy chain CDR1, heavy chain CDR2, and heavy chain CDR3 represented by SEQ ID NOs: 12, 13, and 14, respectively, and light chain CDR1, light chain CDR2, and light chain CDR3 represented by SEQ ID NOs: 15, 16, and 17, respectively;

(3) heavy chain CDR1, heavy chain CDR2, and heavy chain CDR3 represented by SEQ ID NOs: 20, 21, and 22, respectively, and light chain CDR1, light chain CDR2, and light chain CDR3 represented by SEQ ID NOs: 23, 24, and 25, respectively;

(4) heavy chain CDR1, heavy chain CDR2, and heavy chain CDR3 represented by SEQ ID NOs: 28, 29, and 30, respectively, and light chain CDR1, light chain CDR2, and light chain CDR3 represented by SEQ ID NOs: 31, 32, and 33, respectively; and (5) heavy chain CDR1, heavy chain CDR2, and heavy chain CDR3 represented by SEQ ID NOs: 36, 37, and 38, respectively, and light chain CDR1, light chain CDR2, and light chain CDR3 represented by SEQ ID NOs: 39, 40, and 41, respectively,

[28] the drug according to any of [25] to [27], wherein the anti-GPC3 antibody comprises any of the following (1) to (6):

(1) a heavy chain variable region selected from the group of heavy chain variable regions represented by SEQ ID NOs: 44, 45, 46, 47, 48, 49, and 50 and a light chain variable region represented by SEQ ID NO: 51;

(2) a heavy chain variable region selected from the group of heavy chain variable regions represented by SEQ ID NOs: 44, 45, 46, 47, 48, 49, and 50 and a light chain variable region selected from the group of light chain variable regions represented by SEQ ID NOs: 52, 53, 54, 55, 56, 57, 58, 59, 60, 61, 62, 63, 64, 65, and 66;

(3) a heavy chain variable region represented by SEQ ID NO: 67 and a light chain variable region represented by SEQ ID NO: 68;

(4) a heavy chain variable region represented by SEQ ID NO: 69 and a light chain variable region represented by SEQ ID NO: 70;

(5) a heavy chain variable region represented by SEQ ID NO: 71 and a light chain variable region represented by SEQ ID NO: 72; and (6) a heavy chain variable region represented by SEQ ID NO: 71 and a light chain variable region represented by SEQ ID NO: 73,

[29] the drug according to [25], wherein the GPC3-targeting drug comprises an anti-GPC3 antibody conjugated with a cytotoxic substance,

[30] a preparation for GPC3-targeting treatment, comprising an instruction stating that the preparation is to be further administered to a cancer patient having a predetermined value of a concentration of free GPC3 in a biological sample isolated from the cancer patient before the start of GPC3-targeting drug therapy,

[31] a preparation for GPC3-targeting treatment, comprising an instruction stating that the preparation is to be further administered to a cancer patient having a predetermined value of a concentration of free GPC3 in a biological sample isolated from the cancer patient after the start of GPC3-targeting drug therapy,

[32] the preparation according to [30] or [31], wherein the concentration of free GPC3 is a concentration in a whole blood sample, a plasma sample, or a serum sample isolated from the cancer patient,

[33] the preparation according to [32], wherein the concentration of free GPC3 in the biological sample isolated from the cancer patient is a concentration in the plasma sample or the serum sample,

[34] the preparation according to any of [30] to [33], wherein the predetermined value of free GPC3 ranges from 0.1 ng/mL to 100 ng/mL,

[35] the preparation according to any of [30] to [34], wherein the concentration of free GPC3 is measured using an immunological method,

[36] the preparation according to any of [30] to [35], wherein the concentration of free GPC3 has been increased as a result of receiving the GPC3-targeting drug therapy,

[37] the preparation according to any of [30] to [36], wherein the patient shows high expression of GPC3 in an immunohistochemical staining score,

[38] the preparation according to any of [30] to [37], wherein the cancer patient is a liver cancer patient,

[39] the preparation according to any of [30] to [38], wherein the GPC3-targeting drug is administered to achieve a blood trough level of 200 μg/ml or higher in the cancer patient,

[40] the preparation according to any of [30] to [39], wherein the GPC3-targeting drug comprises an anti-GPC3 antibody as an active ingredient,

[41] the preparation according to [40], wherein the anti-GPC3 antibody has antibody-dependent cellular cytotoxicity (ADCC) activity and/or complement-dependent cytotoxicity (CDC) activity,

[42] the preparation according to [40] or [41], wherein the anti-GPC3 antibody is an anti-GPC3 chimeric antibody or a humanized anti-GPC3 antibody comprising any of the following (1) to (5):

(1) heavy chain CDR1, heavy chain CDR2, and heavy chain CDR3 represented by SEQ ID NOs: 4, 5, and 6, respectively, and light chain CDR1, light chain CDR2, and light chain CDR3 represented by SEQ ID NOs: 7, 8, and 9, respectively;

(2) heavy chain CDR1, heavy chain CDR2, and heavy chain CDR3 represented by SEQ ID NOs: 12, 13, and 14, respectively, and light chain CDR1, light chain CDR2, and light chain CDR3 represented by SEQ ID NOs: 15, 16, and 17, respectively;

(3) heavy chain CDR1, heavy chain CDR2, and heavy chain CDR3 represented by SEQ ID NOs: 20, 21, and 22, respectively, and light chain CDR1, light chain CDR2, and light chain CDR3 represented by SEQ ID NOs: 23, 24, and 25, respectively;

(4) heavy chain CDR1, heavy chain CDR2, and heavy chain CDR3 represented by SEQ ID NOs: 28, 29, and 30, respectively, and light chain CDR1, light chain CDR2, and light chain CDR3 represented by SEQ ID NOs: 31, 32, and 33, respectively; and (5) heavy chain CDR1, heavy chain CDR2, and heavy chain CDR3 represented by SEQ ID NOs: 36, 37, and 38, respectively, and light chain CDR1, light chain CDR2, and light chain CDR3 represented by SEQ ID NOs: 39, 40, and 41, respectively,

[43] the preparation according to any of [40] to [42], wherein the anti-GPC3 antibody comprises any of the following (1) to (6):

(1) a heavy chain variable region selected from the group of heavy chain variable regions represented by SEQ ID NOs: 44, 45, 46, 47, 48, 49, and 50 and a light chain variable region represented by SEQ ID NO: 51;

(2) a heavy chain variable region selected from the group of heavy chain variable regions represented by SEQ ID NOs: 44, 45, 46, 47, 48, 49, and 50 and a light chain variable region selected from the group of light chain variable regions represented by SEQ ID NOs: 52, 53, 54, 55, 56, 57, 58, 59, 60, 61, 62, 63, 64, 65, and 66;

(3) a heavy chain variable region represented by SEQ ID NO: 67 and a light chain variable region represented by SEQ ID NO: 68;

(4) a heavy chain variable region represented by SEQ ID NO: 69 and a light chain variable region represented by SEQ ID NO: 70;

(5) a heavy chain variable region represented by SEQ ID NO: 71 and a light chain variable region represented by SEQ ID NO: 72; and (6) a heavy chain variable region represented by SEQ ID NO: 71 and a light chain variable region represented by SEQ ID NO: 73,

[44] the preparation according to [40], wherein the GPC3-targeting drug comprises an anti-GPC3 antibody conjugated with a cytotoxic substance,

[45] a method for treating cancer, comprising administering a GPC3-targeting drug to a patient determined by a method according to any of [1] to [14].

Effect of Invention

According to the present invention, whether GPC3-targeting drug therapy has efficacy or whether GPC3-targeting drug therapy should be continued can be determined conveniently and accurately. This can improve the effects of the GPC3-targeting drug therapy and improve QOL of a patient to be treated. As a result, the better treatment of cancer is achieved.

BRIEF DESCRIPTION OF DRAWINGS

The patent or application file contains at least one drawing executed in color. Copies of this patent or patent application publication with color drawings will be provided by the Office upon request and payment of the necessary fee.

Figure 1A:
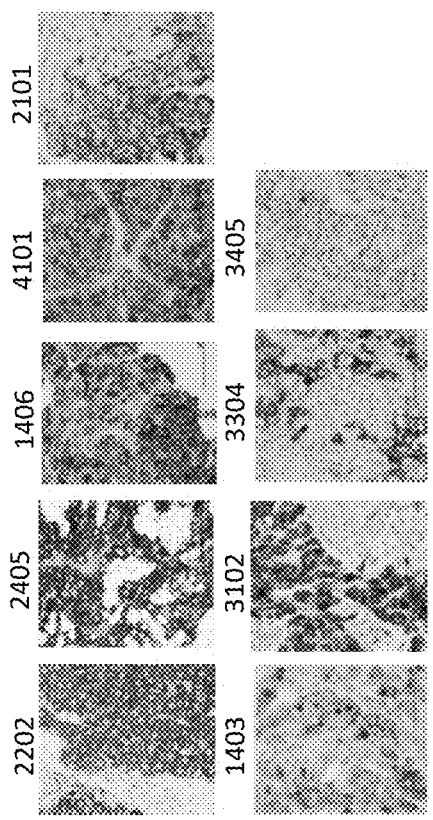
FIG. 1A is a diagram showing the histochemical staining images of tissues evaluated as having high expression in a staining score of GPC3-IHC (staining method 1). The numeral shown in the upper part of each staining image represents a patient number.

The present specification encompasses the contents described in the specification of Japanese Patent Application No. 2012-280304 on which the priority of the present application is based.

DESCRIPTION OF EMBODIMENTS

Definition

Chemical terms and technical terms used in relation to the present invention have meanings generally understood by those skilled in the art, unless otherwise defined herein.

Indefinite Article

In the present invention, the indefinite articles "a" and "an" refer to one or two or more (i.e., at least one) object(s) grammatically represented by the indefinite articles. For example, "a factor" means one factor or two or more factors.

Amino Acid

Each amino acid is indicated herein by single-letter code or three-letter code, or both, as represented by, for example, Ala/A, Leu/L, Arg/R, Lys/K, Asn/N, Met/M, Asp/D, Phe/F, Cys/C, Pro/P, Gln/Q, Ser/S, Glu/E, Thr/T, Gly/G, Trp/W, His/H, Tyr/Y, Ile/I, and Val/V.

Amino Acid Modification

An amino acid in the amino acid sequence of an antigen-binding molecule can be modified by an appropriately adopted method known in the art such as site-directed mutagenesis (Kunkel et al., Proc. Natl. Acad. Sci. USA (1985) 82, 488-492) or overlap extension PCR. Also, a plurality of methods known in the art can be adopted as methods for modifying an amino acid to substitute the amino acid by an amino acid other than natural one (Annu. Rev. Biophys. Biomol. Struct. (2006) 35, 225-249; and Proc. Natl. Acad. Sci. U.S.A. (2003) 100 (11), 6353-6357). For example, a tRNA-containing cell-free translation system (Clover Direct (Protein Express, an R & D oriented company)) comprising a non-natural amino acid bound with an amber suppressor tRNA complementary to UAG codon (amber codon), which is a stop codon, is also preferably used.

The term "and/or" used herein to represent amino acid modification sites is meant to include every combination appropriately represented by "and" and "or". Specifically, for example, the phrase "amino acids 43, 52, and/or 105 are substituted" includes the following variations of amino acid modification:
(a) position 43, (b) position 52, (c) position 105, (d) positions 43 and 52, (e) positions 43 and 105, (f) positions 52 and 105, and (g) positions 43, 52, and 105.

EU Numbering and Kabat Numbering

According to a method used in the present invention, amino acid positions assigned to antibody CDRs and FRs are defined by the Kabat method (Sequences of Proteins of Immunological Interest, National Institute of Health, Bethesda, Md., 1987 and 1991). When the antigen-binding molecule described herein is an antibody or an antigen-binding fragment, amino acids in variable and constant regions are indicated according to the Kabat numbering and the EU numbering conforming to the Kabat amino acid positions, respectively.

Biological Sample

In the present invention, the term "biological sample" refers to a sample of a tissue or a fluid isolated from a subject. In a non-limiting aspect, examples of such samples include plasma, serum, spinal fluid, lymph, external sections of skin, respiratory tract, intestinal tract, and genitourinary tract, tear, saliva, sputum, milk, whole blood or any blood fraction, blood derivatives, blood cells, tumor, nervous tissues, organs or any type of tissue, any sample obtained by lavage (e.g., samples derived from the bronchi), and samples of components constituting cell cultures in vitro.

The concentration of free GPC3 can be measured in a biological sample isolated from a patient. The concentration of free GPC3 may be measured in, for example, a whole blood sample or a blood fraction (e.g., serum or plasma) sample (also referred to as a whole blood sample, a serum sample, or a plasma sample, respectively, herein). In a non-limiting aspect, the concentration of free GPC3 in a whole blood sample, a serum sample, or a plasma sample from a patient can be measured using, for example, commercially available Human Glypican-3 ELISA kit (BioMosaics Inc.) or Enzyme-linked Immunosorbent Assay Kit For Glypican 3 (GPC3) (USCN Life Science Inc.) and the whole blood sample, the serum sample, or the plasma sample treated with EDTA.

The term "isolated" refers to causing "artificial" change from a natural state, i.e., shifting and/or removing a naturally occurring substance from its original environment. In the present invention, the term "isolated" means that, for example, a polynucleotide or a polypeptide present in an organism is unisolated, whereas the same polynucleotide or polypeptide thereas is isolated when separated from a material present with the polynucleotide or the polypeptide in a natural state. A polynucleotide or a polypeptide introduced into an organism by transformation, genetic manipulation, or any other recombination method is in an isolated state even when present in the organism (regardless of being alive or dead).

Free GPC3

In the present invention, the term "free GPC3" refers to GPC3 unanchored to GPC3-expressing cells and includes fragments of secretory GPC3 that can be easily dissociated from GPC3 anchored to GPC3-expressing cells under particular conditions in vivo or in vitro. In a non-limiting aspect, examples of the "free GPC3" can include a polypeptide from the amino terminus to position 358 in GPC3 consisting of the polypeptide defined by SEQ ID NO: 1, a polypeptide from the amino terminus to position 374 in GPC3 consisting of the polypeptide defined by SEQ ID NO: 1, a GPC3 polypeptide liberated by the degradation of a GPI anchor present at the carboxy terminus, and their fragments (Patent Literature 7). Those skilled in the art can appropriately select an approach known in the art for determining the structure of free GPC3. In a non-limiting aspect, a method therefor that may be appropriately used involves, for example, directly detecting free GPC3 present in the serum or the plasma of a patient or a model animal by the method described in Patent Literature 7 and analyzing its structure or involves, for example, allowing an enzyme dissociating free GPC3, such as convertase, phospholipase D, or Notum, to act on GPC3 expressed in cells cultured in vitro, detecting the resulting free GPC3, and analyzing its structure (e.g., J. Cell. Biol. (2003) 163 (3), 625-635).

Method for Measuring Concentration of Free GPC3

The concentration of free GPC3 can be measured by one or more methods selected from the group consisting of the following: spectroscopic methods such as nuclear magnetic resonance (NMR) and mass spectrometry (MS); and SELDI (-TOF), MALDI(-TOF), 1D gel-based analysis, 2D gel-based analysis, liquid chromatography (e.g., high-pressure liquid chromatography (HPLC) or low-pressure liquid chromatography (LPLC)), thin-layer chromatography, and LC-MS-based techniques. Examples of appropriate LCMS techniques can include ICAT® (Applied Biosystems, Inc.) and iTRAQ® (Applied Biosystems, Inc.). Also, a method which involves detecting a further fragment of free GPC3 further digested with an appropriate enzyme may be appropriately adopted.

The assay of free GPC3 can be carried out by a direct or indirect detection method. Free GPC3 can be detected directly or indirectly via the interaction of a ligand or a ligand group with, for example, an enzyme, a bond, a receptor or a transport protein, an antibody, a peptide, an aptamer or an oligonucleotide, or an arbitrary synthetic chemical receptor or compound capable of specifically binding to free GPC3. The ligand may be modified with a detectable label such as a luminescent label, a fluorescent label, or a radioactive label, and/or an affinity tag.

Immunological Method

Examples of preferred methods for assaying free GPC3 can include immunological methods using an antibody capable of binding to an epitope present in GPC3. Examples of the immunological methods include enzyme immunoassay (ELISA or EIA), fluorescence immunoassay (FIA), radioimmunoassay (RIA), luminescence immunoassay (LIA), immunoenzymatic technique, fluorescent antibody technique, immunochromatography, immunoturbidimetry, latex turbidimetry, and latex agglutination assay. In the immunological method of the present invention, free GPC3 may be assayed by procedures of manual operation or using an apparatus such as an analyzer.

The immunological method of the present invention can be performed according to, for example, a method known in the art such as sandwich technique. For example, a primary antibody immobilized on a carrier, a biological sample, and a secondary antibody modified with a labeling material are reacted simultaneously or in order. This reaction forms a complex of the primary antibody immobilized on a carrier, free GPC3, and the secondary antibody modified with a labeling material. The labeling material conjugated with the secondary antibody contained in this complex can be quantified to thereby measure the amount (concentration) of the free GPC3 contained in the biological sample.

In the case of, for example, the enzyme immunoassay, a primary antibody-immobilized microplate, serially diluted biological samples, a secondary antibody modified with an enzyme such as HRP, a washing buffer, and a solution containing a substrate reactive with the enzyme such as HRP are preferably used. In a non-limiting aspect of assay, the enzyme modifying the secondary antibody is reacted under the optimum conditions thereof with the substrate. The amount of the resulting enzymatic reaction product can be measured by an optical method or the like. In the case of the fluorescence immunoassay, a primary antibody-immobilized optical waveguide, serially diluted biological samples, a secondary antibody modified with a fluorescent material, and a washing buffer may be preferably used. In a non-limiting aspect of assay, the fluorescent material modifying the secondary antibody can be irradiated with excitation light to thereby emit fluorescence, the intensity of which is then measured.

The radioimmunoassay involves measuring the amount of radiation from a radioactive substance. The luminescence immunoassay involves measuring luminescence intensity derived from a luminescent reaction system. For example, the immunoturbidimetry, the latex turbidimetry, or the latex agglutination assay involves measuring transmitted light or scattering light by an endpoint or rate method. The immunochromatography, for example, which is based on visual observation, involves visually measuring the color of the labeling material appearing on a test line. Alternatively, an instrument such as an analyzer may be appropriately used instead of this visual measurement.

In the immunological method of the present invention, the primary antibody for immobilization on a carrier can be adsorbed or bound to the carrier by a method such as physical adsorption, chemical binding, or a combination thereof. A method known in the art may be appropriately used for immobilizing the antibody by physical adsorption. Examples of the method include a method which involves contacting the antibody with the carrier by mixing in a solution such as a buffer solution, and a method which involves contacting the antibody dissolved in a buffer or the like with the carrier. Alternatively, the antibody may be immobilized onto the carrier by chemical binding. Examples of the method include a method which involves contacting the antibody and the carrier by mixing with a divalent cross-linking reagent such as glutaraldehyde, carbodiimide, imide ester, or maleimide to react the reagent with amino groups, carboxyl groups, thiol groups, aldehyde groups, or hydroxy groups in both the antibody and the carrier. Such immobilization may require treatment for suppressing nonspecific reaction or the natural aggregation or the like of the antibody-immobilized carrier. In such a case, the aftertreatment of the immobilization can be performed by a method known in the art. Examples of the method include a method which involves coating the surface or inner wall of the antibody-immobilized carrier by contacting with, for example, a protein (e.g., bovine serum albumin (BSA), casein, gelatin, egg albumin, or a salt thereof), a surfactant, or a skimmed milk.

In the immunological method of the present invention, the secondary antibody for modification with a labeling material can be adsorbed or bound to the labeling material by a method such as physical adsorption, chemical binding, or a combination thereof. A method known in the art may be appropriately used for binding the antibody to the labeling material by physical adsorption. Examples of the method include a method which involves contacting the antibody with the labeling material by mixing in a solution such as a buffer solution, and a method which involves contacting the antibody dissolved in a buffer or the like with the labeling material. When the labeling material is, for example, gold colloid or latex, the physical adsorption method is effective. The antibody can be mixed and contacted with the gold colloid in a buffer to obtain a gold colloid-labeled antibody. Alternatively, the antibody may be modified with the labeling material by chemical binding. Examples of the method include a method which involves contacting the antibody and the labeling material by mixing with a divalent cross-linking reagent such as glutaraldehyde, carbodiimide, imide ester, or maleimide to react the reagent with amino groups, carboxyl groups, thiol groups, aldehyde groups, or hydroxy groups in both the antibody and the labeling material. When the labeling material is, for example, a fluorescent material, an enzyme, or a chemiluminescent material, the chemical binding method is effective. Such modification may require treatment for suppressing nonspecific reaction or the natural aggregation or the like of the antibody modified with the labeling material. In such a case, the aftertreatment of the labeling can be performed by a method known in the art. Examples of the method include a method which involves coating the labeling material-bound antibody by contacting with, for example, a protein (e.g., bovine serum albumin (BSA), casein, gelatin, egg albumin, or a salt thereof), a surfactant, or a skimmed milk.

For example, peroxidase (POD), alkaline phosphatase (ALP), β-galactosidase, urease, catalase, glucose oxidase, lactate dehydrogenase, or amylase can be used as the labeling material for enzyme immunoassay. For example, fluorescein isothiocyanate, tetramethylrhodamine isothiocyanate, substituted rhodamine isothiocyanate, dichlorotriazine isothiocyanate, cyanine, or merocyanine can be used for fluorescence immunoassay. For example, tritium, iodine 125, or iodine 131 can be used for radioimmunoassay. For example, a luminol system, a luciferase system, an acridinium ester system, or a dioxetane compound system can be used for luminescence immunoassay. Alternatively, fine particles made of a material such as polystyrene, a styrene-styrene sulfonate copolymer, an acrylonitrile-butadiene-styrene copolymer, a vinyl chloride-acrylic acid ester copolymer, a vinyl acetate-acrylic acid copolymer, polyacrolein, a styrene-methacrylic acid copolymer, a styrene-glycidyl (meth)acrylate copolymer, a styrene-butadiene copolymer, a methacrylic acid polymer, an acrylic acid polymer, latex, gelatin, liposome, a microcapsule, silica, alumina, carbon black, a metal compound, a metal, a metal colloid, a ceramic, or a magnetic substance can be used for immunochromatography, immunoturbidimetry, latex turbidimetry, or latex agglutination assay.

A solid-phase carrier in the form of, for example, beads, a microplate, a test tube, a stick, a membrane, or a test pieces made of a material such as polystyrene, polycarbonate, polyvinyltoluene, polypropylene, polyethylene, polyvinyl chloride, nylon, polymethacrylate, polyacrylamide, latex, liposome, gelatin, agarose, cellulose, Sepharose, glass, a metal, a ceramic, or a magnetic substance can be appropriately used as the carrier in the immunological method of the present invention.

The present invention also provides an assay kit comprising components for use in the immunological method of the present invention. The assay kit comprises at least one type of antibody capable of binding to an epitope present in GPC3. The antibody may be provided in a state immobilized on the carrier mentioned above or may be provided independently of the carrier. The kit may additionally comprise standard solutions of serially diluted free GPC3. The assay kit may further comprise at least one type of antibody capable of binding to an epitope different from that present in GPC3. Assay principles, etc., for use in the immunoassay kit of the present invention are the same as in the immunological method mentioned above. In the immunoassay kit of the present invention, various aqueous solvents may be used. Examples of the aqueous solvents include purified water, saline, and various buffers such as tris buffers, phosphate buffers, and phosphate-buffered saline. The pH of this buffer can be appropriately selected from among suitable pHs. The pH value used is not limited and is generally selected within the range of pH 3 to 12.

The immunoassay kit of the present invention may further appropriately contain, in addition to the components mentioned above, one or two or more components selected from proteins (e.g., bovine serum albumin (BSA), human serum albumin (HSA), casein, and salts thereof), various salts, various sugars, skimmed milk, various animal sera (e.g., normal rabbit serum), various antiseptics (e.g., sodium azide and antibiotics), activating substances, reaction-promoting substances, sensitivity-increasing substances (e.g., polyethylene glycol), nonspecific reaction-inhibiting substances, and various surfactants such as nonionic surfactants, amphoteric surfactants, and anionic surfactants. The concentrations of these components contained in the assay reagent are not limited and are preferably 0.001 to 10% (W/V). Particularly preferred concentrations are appropriately selected within the range of 0.01 to 5% (W/V).

The immunoassay kit of the present invention may be further combined with other reagents, in addition to the components mentioned above. Examples of these other reagents include buffers, diluting solutions for biological samples, reagent diluting solutions, reagents containing labeling materials, reagents containing substances that generate signals such as color, reagents containing substances involved in the generation of signals such as color, reagents containing substances for calibration, and reagents containing substances for accuracy control.

The immunoassay kit of the present invention can have any form without limitations and may be provided as an integral-type diagnostic kit comprising all of the components constituting the immunoassay kit of the present invention in order to carry out assay conveniently in a short time. Examples of the integral-type diagnostic kit include ELISA kits, fluorescence immunoassay kits, and immunochromatography kits. The ELISA kit form comprises, for example, a primary antibody-immobilized microplate, standard solutions of serially diluted free GPC3, a secondary antibody modified with an enzyme such as HRP, a washing buffer, and a substrate solution for the enzymatic reaction. The fluorescence immunoassay kit comprises, for example, a primary antibody-immobilized optical waveguide, standard solutions of serially diluted free GPC3, a secondary antibody modified with a fluorescent material, and a washing buffer. The immunochromatography kit comprises a membrane housed in a reaction cassette. In one exemplary aspect, the primary antibody is immobilized at one end (downstream) of the membrane; a developing solution is placed at the other end (upstream) of the membrane; a pad supplemented with a substrate for the labeling agent is disposed in proximity (downstream) to the developing solution; and a pad supplemented with the secondary antibody labeled as described above is disposed in the central part of the membrane.

In the present invention, preferred examples of biological samples used for detecting the expression level of GPC3 in tissues include test subject-derived preparations. The test subject-derived preparation is preferably a tissue obtained from the test subject, more preferably a liver cancer or hepatocellular cancer tissue of the test subject. The liver cancer or hepatocellular cancer tissue is collected preferably using a biopsy method known in the art. The liver biopsy refers to a method of directly inserting a thin long needle into the liver from skin surface and collecting liver tissues. The needling site is typically the intercostal space of the right lower chest. The safety of the needling site is confirmed before operation using an ultrasonic examination apparatus. Then, the needling site is disinfected. A region from the skin to the surface of the liver is subjected to anesthesia. After small incision of the skin at the needling site, a puncture needle is inserted thereto.

For microscopic observation by transmitted beams, the tissue preparation is sliced to a degree that allows beams of light for use in the microscope to sufficiently penetrate the tissue slice. At a stage prior to the slicing, the tissue preparation is fixed. Specifically, proteins in tissues or cells are coagulated by dehydration or denaturation to thereby rapidly kill the cells constituting the tissues. The resulting structure is stabilized and insolubilized. First, the tissue preparation to be fixed is cut into a fragment with a size and a shape suitable for the preparation of paraffin-embedded sections by use of a knife such as a surgical knife. Subsequently, the fragment is dipped in a fixative, which is a reagent used for carrying out fixation. Formalin, more preferably neutral buffered formalin, is preferably used as the fixative. The concentration of the neutral buffered formalin is appropriately selected according to the characteristics or physical properties of the tissue preparation. The concentration used may be appropriately changed between 1 and 50%, preferably 5 and 25%, more preferably 10 and 15%. The fixative with the tissue preparation dipped therein is appropriately degassed using a vacuum pump. For fixation, the tissue preparation is left for several hours in the fixative under conditions of ordinary pressure and room temperature. The time required for the fixation can be appropriately selected within the range of 1 hour to 7 days, preferably 2 hours to 3 days, more preferably 3 hours to 24 hours, further preferably 4 hours to 16 hours. The tissue preparation thus fixed is appropriately dipped in a phosphate buffer solution or the like for additional several hours (which can be appropriately selected within the range of 2 hours to 48 hours, preferably 3 hours to 24 hours, more preferably 4 hours to 16 hours).

Next, sections can be preferably prepared by freeze sectioning or paraffin sectioning from the tissue preparation thus fixed. Preferred examples of the freeze sectioning include a method which involves adding tissues into O.C.T. Compound (Miles Inc.), freezing the mixture, and slicing the frozen mixture using a cryostat (frozen section preparation apparatus). In the paraffin sectioning, the fixed tissue preparation is dipped in an embedding agent, which is then solidified to thereby impart thereto uniform and appropriate hardness. Paraffin can be preferably used as the embedding agent. The fixed tissue preparation is dehydrated using ethanol. Specifically, the tissue preparation is dipped in 70% ethanol, 80% ethanol, and 100% ethanol in this order and thereby dehydrated. The time required for the dipping and the number of runs can be appropriately selected within the ranges of 1 hour to several days and 1 to 3 times, respectively. The tissue preparation may be dipped therein at room temperature or 4° C. In the case of dipping at 4° C., a longer dipping time (e.g., overnight) is more preferred. After replacement of the liquid phase with xylene, the tissue preparation is embedded in paraffin. The time required for the replacement of the liquid phase with xylene can be appropriately selected within the range of 1 hour to several hours. This replacement may be performed at room temperature or 4° C. In the case of replacement at 4° C., a longer replacement time (e.g., overnight) is more preferred. The time required for the embedding in paraffin and the number of runs can be appropriately selected within the ranges of 1 hour to several hours and 1 to 4 times, respectively. This embedding may be performed at room temperature or 4° C. In the case of embedding at 4° C., a longer embedding time (e.g., overnight) is more preferred. Alternatively, the tissue preparation may be preferably embedded in paraffin using paraffin embedding apparatus (EG1160, Leica, etc.) that automatically performs paraffin embedding reaction.

The tissue preparation thus paraffin-embedded is bonded to a block base to prepare a "block". This block is sliced into the desired thickness selected from thicknesses of 1 to 20 μm by use of a microtome. The sliced tissue section is left standing on a glass slide as a permeable support and thereby fixed thereon. In this case, the glass slide coated with 0.01% poly-L-lysine (Sigma-Aldrich Corp.) and then dried may be preferably used in order to prevent the tissue section from coming off. The fixed tissue section is dried in air for an appropriate time selected from between several minutes and 1 hour.

Epitope Retrieval

In a preferred aspect, an epitope in an antigen whose reactivity with an antibody has been attenuated due to formalin fixation is retrieved. In the present invention, protease-induced epitope retrieval (PIER) or heat-induced epitope retrieval (HIER) may be applied to the retrieval. In a non-limiting aspect, PIER may be applied to one of "two identifiable tissue preparations" prepared as shown below, while HIER may be applied to the other preparation. In this case, a difference in the degree of staining between these preparations reacted with antibodies can be digitized.

In a non-limiting aspect, a set of two tissue preparations is prepared, which are prepared as shown in the paragraph "Biological sample" and attached onto permeable supports. The tissue preparations are desirably two histologically identifiable tissue preparations. The term "identifiable" means that two tissue preparations to be mutually compared are composed of substantially the same cells or tissues in test subject-derived preparations serving as origins of the tissue preparations. For example, two tissue preparations prepared as adjacent sections correspond to two identifiable tissue preparations. In the present invention as well, the "two identifiable tissue preparations" refer to two tissue preparations prepared as adjacent sections, unless otherwise specified. In addition, two tissue preparations composed of cells or tissues structurally identifiable between the preparations correspond to "two identifiable tissue preparations", even if the tissue preparations are not prepared as adjacent sections. Preferred examples of such two tissue preparations composed of cells or tissues structurally identifiable therebetween include (1) tissue sections containing cells derived from the same cells at the same positions on plane coordinates in the sections, and (2) tissue sections in which at least 50% or more, preferably 60% or more, more preferably 70% or more, further preferably 80% or more, still further preferably 90% or more, particularly preferably 95% or more of the cells are present at the same positions on the plane coordinates.

The heat-induced epitope retrieval appropriately employs, for example, a heating method using microwave, a heating method using an autoclave, or a heating method using boiling treatment. In the case of boiling treatment at an output of 780 W so as to keep a liquid temperature at approximately 98° C., the time required for the retrieval including the treatment is appropriately selected from between 5 minutes and 60 minutes and is, for example, 10 minutes. The epitope retrieval treatment can be performed in a 10 mM sodium citrate buffer solution as well as commercially available Target Retrieval Solution (DakoCytomation), for example. Target Retrieval Solution is used in Examples described below. Any buffer solution or aqueous solution is preferably used as long as an epitope in the antigen that is recognized by an anti-GPC3 antibody acquires the ability to bind to the antibody as a result of the retrieval treatment so that an antigen-antibody complex mentioned later can be detected.

The protease for use in the protease-induced epitope retrieval is not limited by its type or origin. Generally available protease can be appropriately selected for use. Preferred examples of the protease used include pepsin with 0.05% concentration in 0.01 N hydrochloric acid, trypsin with 0.1% concentration further containing $CaCl_2$ with 0.01% concentration in a tris buffer solution (pH 7.6), and protease K with a concentration of 1 to 50 μg/ml in a 10 mM tris-HCl buffer solution (pH 7.8) containing 10 mM EDTA and 0.5% SDS. In the case of using protease K, the pH of the reaction solution is appropriately selected from between 6.5 and 9.5, and an SH reagent, a trypsin inhibitor, or a chymotrypsin inhibitor may be appropriately used. Specific examples of such preferred protease also include protease attached to Histofine HER2 kit (MONO) (Nichirei Biosciences Inc.). The protease-induced epitope retrieval is usually performed at 37° C. The reaction temperature may be appropriately changed within the range of 25° C. to 50° C. The reaction time of the protease-induced epitope retrieval performed at 37° C. is appropriately selected from between, for example, 1 minute and 5 hours and is, for example, 15 minutes, 30 minutes, 45 minutes, 1 hour, 2 hours, 3 hours, or 4 hours. After the completion of the retrieval treatment, the tissue preparation thus treated is washed with a washing buffer solution. Phosphate-buffered saline (PBS) is preferably used as the washing buffer solution. Alternatively, a tris-HCl buffer solution may be preferably used. The washing conditions adopted in this method usually involve three runs of washing at room temperature for 5 minutes. The washing time and temperature may be appropriately changed.

Reaction Between Tissue Preparation and Anti-GPC3 Antibody

The tissue preparation thus treated by the heat-induced epitope retrieval and/or the tissue preparation thus treated by the protease-induced epitope retrieval are reacted with an anti-GPC3 antibody mentioned later as a primary antibody. The reaction is carried out under conditions appropriate for the recognition of an epitope in the antigen by the anti-GPC3 antibody and the subsequent formation of an antigen-antibody complex. The reaction is usually carried out overnight at 4° C. or at 37° C. for 1 hour. The reaction conditions may be appropriately changed within a range appropriate for the recognition of an epitope in the antigen by the antibody and the subsequent formation of an antigen-antibody complex. For example, the reaction temperature may be changed within the range of 4° C. to 50° C., while the reaction time may be changed between 1 minute and 7 days. A longer reaction time is more preferred for the reaction carried out at a low temperature. After the completion of the primary antibody reaction, each tissue preparation is washed with a washing buffer solution. Phosphate-buffered saline (PBS) is preferably used as the washing buffer solution. Alternatively, a tris-HCl buffer solution may be preferably used. The washing conditions adopted in this method usually involve three runs of washing at room temperature for 5 minutes. The washing time and temperature may be appropriately changed.

Subsequently, each tissue preparation thus reacted with the primary antibody is reacted with a secondary antibody that recognizes the primary antibody. A secondary antibody labeled in advance with a labeling material for visualizing the secondary antibody is usually used. Preferred examples of the labeling material include: fluorescent dyes such as fluorescein isothiocyanate (FITC), Cy2 (Amersham Biosciences Corp.), and Alexa 488 (Molecular Probes Inc.); enzymes such as peroxidase and alkaline phosphatase; and gold colloid.

The reaction with the secondary antibody is carried out under conditions appropriate for the formation of an antigen-antibody complex between the anti-GPC3 antibody and the secondary antibody that recognizes the anti-GPC3 antibody. The reaction is usually carried out at room temperature or 37° C. for 30 minutes to 1 hour. The reaction conditions may be appropriately changed within a range appropriate for the formation of an antigen-antibody complex between the anti-GPC3 antibody and the secondary antibody. For example, the reaction temperature may be changed within the range of 4° C. to 50° C., while the reaction time may be changed between 1 minute and 7 days. A longer reaction time is more preferred for the reaction carried out at a low temperature. After the completion of the secondary antibody reaction, each tissue preparation is washed with a washing buffer solution. Phosphate-buffered saline (PBS) is preferably used as the washing buffer solution. Alternatively, a tris-HCl buffer solution may be preferably used. The washing conditions adopted in this method usually involve three runs of washing at room temperature for 5 minutes. The washing time and temperature may be appropriately changed.

Next, each tissue preparation thus reacted with the secondary antibody is reacted with a substance capable of visualizing the labeling material. When peroxidase is used as the labeling material in the secondary antibody, a 0.02% aqueous hydrogen peroxide solution and a diaminobenzidine (DAB) solution concentration-adjusted to 0.1% with a 0.1 M tris-HCl buffer solution (pH 7.2) are mixed in equal amounts immediately before incubation and the tissue preparation is incubated in the resulting reaction solution. A chromogenic substrate such as DAB-Ni or AEC+ (both from Dako Japan Inc.) may be appropriately selected instead of DAB. During the course of incubation, the visualization reaction can be stopped by the dipping of the tissue preparation in PBS at the stage where appropriate color development is confirmed by the occasional microscopic observation of the degree of color development.

When alkaline phosphatase is used as the labeling material in the secondary antibody, each tissue preparation is incubated in a 5-bromo-4-chloro-3-indolyl phosphoric acid (BCIP)/nitro blue tetrazolium (NBT) (Zymed Laboratories, Inc.) substrate solution (solution of NBT and BCIP dissolved at concentrations of 0.4 mM and 0.38 mM, respectively, in a 50 mM sodium carbonate buffer solution (pH 9.8) containing 10 mM $MgCl_2$ and 28 mM NaCl). Alternatively, for example, Permanent Red, Fast Red, or Fuchsin+ (all from Dako Japan Inc.) may be appropriately used instead of BCIP and NBT. Prior to the incubation, the tissue preparation may be preincubated at room temperature for 1 minute to several hours with a 0.1 M tris-HCl buffer solution (pH 9.5) containing levamisole chloride (Nacalai Tesque, Inc.), an inhibitor of endogenous alkaline phosphatase, with a concentration of 1 mM, 0.1 M sodium chloride, and 50 mM magnesium chloride. During the course of incubation, the tissue preparation is washed with water or with TBST (TBS containing 0.1% Tween 20) after stop of the reaction by the addition of TBS containing 2% polyvinyl alcohol, at the stage where the deposition of a final reaction product purple formazan is confirmed by occasional microscopic observation. When gold colloid is used as the label in the secondary antibody, metallic silver is attached to gold particles by silver intensification to thereby visualize the gold colloid. The silver intensification method is generally known to those skilled in the art.

When a fluorescent dye such as fluorescein isothiocyanate (FITC), Cy2 (Amersham Biosciences Corp.), or Alexa 488 (Molecular Probes Inc.) is used as the labeling material in the secondary antibody, the reaction step of the visualizing substance is unnecessary. Each tissue preparation is irradiated with light at an excitation wavelength for the fluorescent material. Emitted light can be appropriately detected using a fluorescence microscope.

Immunohistochemical Staining Score

In a non-limiting aspect, the present invention also provides a method for determining the efficacy of GPC3-targeting drug therapy or determining the continuation of GPC3-targeting drug therapy from the concentration of free GPC3 as well as the expression level of GPC3 detected in tissues by the method described above. In a non-limiting aspect, the expression of GPC3 detected in tissues by the method described above is digitized by, for example, a non-limiting method exemplified below. In the present invention, such a digitized expression level of GPC3 in tissues is referred to as an "immunohistochemical staining score of GPC3".

The respective scores of positive cell rate (PR), staining intensity of cytoplasm (SI-cp) or staining intensity of cell membrane (SI-cm), and staining pattern of cell membrane (Sp-cm) are calculated according to the criteria shown in Table 1 by a method described in WO2009116659 and added on the basis of calculation expressions 1 and 2. The resulting score is exemplified as the non-limiting immunohistochemical staining score of GPC3 (referred to as "composite score 1" for the sake of convenience) of the present invention.

TABLE 1-1

| Criterion | Evaluation | Score |
|---|---|---|
| Positive cell rate (PR) | 0 | 0 |
| | 1% or more and less than 20% | 1 |
| | 20% or more and less than 50% | 2 |
| | 50% or more | 3 |
| Staining intensity (SI) Cytoplasm (SI-cp) | Slightly positive | 0 |
| | Weakly positive | 1 |
| Cell membrane (SI-cm) | Moderately positive and/or weakly positive with strong positivity | 2 |
| | Moderately positive | 3 |
| | Strongly positive | 4 |
| Staining pattern of cell membrane (SP-cm) | Negative | 0 |
| | When only a portion of the cell membranes of cells was stained | 1 |
| | When a portion of the cell membranes of most of these cells was stained and the cell membranes of some of the cells were circumferentially stained | 2 |
| | When the cell membranes of most of these cells were circumferentially stained | 3 |

(Sp-cm scores were calculated by the evaluation of cell staining in the visual field under microscope using an objective lens with a magnification of 4 or 10.)

$$IHC\ total = PR + SI\text{-}Cp + SI\text{-}Cm + Sp\text{-}Cm \quad \text{[Expression 1]}$$

$$IHC\ cm = PR + SI\text{-}Cm + Sp\text{-}Cm \quad \text{[Expression 2]}$$

TABLE 1-2

| Composite score 1 | IHC total score |
|---|---|
| High expression | 7 or higher |
| Low or moderate expression | Lower than 7 |

In addition, the H-score is known (literature: KS. McCarty Jr. et al., Use of a monoclonal anti-Estrogen receptor antibody in the immunohistochemical evaluation of human tumors. Cancer Res. Suppl. (1986) 46, 4244s-4248s), which is calculated on the basis of the proportion of cells that exhibit each staining intensity (staining intensity of cell membrane or cytoplasm) classified into 0 to 3.

Another example of the immunohistochemical staining score includes the following scoring algorithm for classification of 0 to 3+ on the basis of the staining intensity of membrane, the staining intensity of cytoplasm, and the degree of staining, and an evaluation score based on the algorithm (composite score 2).

TABLE 2

| Score | Evaluation |
|---|---|
| 0 | When cell membranes were not stained When less than 10% of tumor cells exhibited intracytoplasmic staining |
| 1+ | When less than 10% of tumor cells exhibited cell membrane staining and/or When 10% or more of tumor cells exhibited intracytoplasmic staining (note that strong intracytoplasmic staining, if any, remains at less than 50% of the tumor cells) |
| 2+ | When 10% or more of tumor cells exhibited weak or moderate cell membrane staining (note that strong cell membrane staining, if any, remains at less than 10% of the tumor cells) regardless of the presence or absence of intracytoplasmic staining in 10% or more of the tumor cells (note that intracytoplasmic staining, if any, remains at less than 50% of the tumor cells) |

TABLE 2-continued

| Score | Evaluation |
|---|---|
| 3+ | When 10% or more of tumor cells exhibited strong cell membrane staining regardless of the presence or absence of intracytoplasmic staining or When 50% or more of tumor cells exhibited strong intracytoplasmic staining |

In the present invention, for example, the composite score 1, the H-score, and the composite score 2 may be used alone or in combination as the "immunohistochemical staining score of GPC3". In a non-limiting aspect, the composite score 1 may be used as the "immunohistochemical staining score of GPC3". In another non-limiting aspect, the composite score 2 may be used as the "immunohistochemical staining score of GPC3".

GPC3-Targeting Drug

In the present invention, the term "GPC3-targeting drug" refers to every molecule that blocks, suppresses, inhibits, or reduces the biological activity of GPC3 including a signal pathway mediated by GPC3 or is cytotoxic to cells expressing GPC3. The term "targeting treatment" does not suggest a certain mechanism having biological effects and conceptually includes every possible effect of the pharmacological, physiological, and biochemical interactions of GPC3. Examples of the GPC3-targeting drug include: (1) antagonistic or non-antagonistic inhibitors of the binding of GPC3 to a GPC3-binding ligand, i.e., active substances that interfere with the binding of GPC3 to its ligand; (2) active substances that do not interfere with the binding of GPC3 to its ligand but instead inhibit or decrease activity brought about by the binding of GPC3 to its ligand; (3) active substances that decrease GPC3 expression; and (4) active substances capable of eliciting cytotoxic activity against cells expressing GPC3. In a non-limiting aspect, examples of the ligand can include wnt (Cancer Res. (2005) 65, 6245-6254), IGF-II (Carcinogenesis (2008) 29 (7), 1319-1326), and fibroblast growth factor 2 (Int. J. Cancer (2003) 103 (4), 455-465). In a non-limiting aspect, such active substances can include, for example, antibodies (including their antigen-binding domains), nucleic acid molecules (antisense or RNAi molecules, etc.), peptides, non-peptidic low-molecular-weight organic materials.

In a non-limiting aspect, examples of the non-peptidic low-molecular-weight organic material that may be used as the GPC3-targeting drug of the present invention include non-peptidic low-molecular-weight quinoline derivatives (WO2008/046085) which act on methylation suppressor genes. Further examples thereof can include HLA-A2-restricted GPC3 peptide 144-152 (SEQ ID NO: 2) and HLA-A24-restricted GPC3 peptide 298-306 (SEQ ID NO: 3) (Clin. Cancer Res. (2006) 12 (9), 2689-2697) which elicit the cytotoxic activity of cytotoxic T cells.

Anti-GPC3 Antibody

In a non-limiting aspect, examples of the anti-GPC3 antibody that may be used as the GPC3-targeting drug of the present invention can include an antibody-drug conjugate (ADC) (WO2007/137170) comprising a 1G12 antibody (WO2003/100429) (sold under catalog No. B0134R by BioMosaics Inc.) conjugated with a cytotoxic substance. In an alternative non-limiting aspect, examples of the anti-GPC3 antibody include a humanized anti-GPC3 antibody described in WO2006/006693 or WO2009/041062.

Specifically, a humanized anti-GPC3 antibody comprising heavy chain CDR1, heavy chain CDR2, and heavy chain CDR3 represented by SEQ ID NOs: 4, 5, and 6, respectively, and light chain CDR1, light chain CDR2, and light chain CDR3 represented by SEQ ID NOs: 7, 8, and 9, respectively, can be used as the GPC3-targeting drug of the present invention. The humanized anti-GPC3 antibody can be prepared using, as templates for humanization, appropriately selected human framework sequences having high sequence identity to a heavy chain framework sequence represented by SEQ ID NO: 10 or a light chain framework sequence represented by SEQ ID NO: 11.

In a further alternative non-limiting aspect, an anti-GPC3 chimeric antibody or a humanized anti-GPC3 antibody comprising heavy chain CDR1, heavy chain CDR2, and heavy chain CDR3 represented by SEQ ID NOs: 12, 13, and 14, respectively, and light chain CDR1, light chain CDR2, and light chain CDR3 represented by SEQ ID NOs: 15, 16, and 17, respectively, can be used as the GPC3-targeting drug of the present invention. The humanized anti-GPC3 antibody can be prepared using, as templates for humanization, appropriately selected human framework sequences having high sequence identity to a heavy chain framework sequence represented by SEQ ID NO: 18 or a light chain framework sequence represented by SEQ ID NO: 19.

In an alternative non-limiting aspect, an anti-GPC3 chimeric antibody or a humanized anti-GPC3 antibody comprising heavy chain CDR1, heavy chain CDR2, and heavy chain CDR3 represented by SEQ ID NOs: 20, 21, and 22, respectively, and light chain CDR1, light chain CDR2, and light chain CDR3 represented by SEQ ID NOs: 23, 24, and 25, respectively, can be used as the GPC3-targeting drug of the present invention. The humanized anti-GPC3 antibody can be prepared using, as templates for humanization, appropriately selected human framework sequences having high sequence identity to a heavy chain framework sequence represented by SEQ ID NO: 26 or a light chain framework sequence represented by SEQ ID NO: 27.

In a further alternative non-limiting aspect, an anti-GPC3 chimeric antibody or a humanized anti-GPC3 antibody comprising heavy chain CDR1, heavy chain CDR2, and heavy chain CDR3 represented by SEQ ID NOs: 28, 29, and 30, respectively, and light chain CDR1, light chain CDR2, and light chain CDR3 represented by SEQ ID NOs: 31, 32, and 33, respectively, can be used as the GPC3-targeting drug of the present invention. The humanized anti-GPC3 antibody can be prepared using, as templates for humanization, appropriately selected human framework sequences having high sequence identity to a heavy chain framework sequence represented by SEQ ID NO: 34 or a light chain framework sequence represented by SEQ ID NO: 35.

In an alternative non-limiting aspect, an anti-GPC3 chimeric antibody or a humanized anti-GPC3 antibody comprising heavy chain CDR1, heavy chain CDR2, and heavy chain CDR3 represented by SEQ ID NOs: 36, 37, and 38, respectively, and light chain CDR1, light chain CDR2, and light chain CDR3 represented by SEQ ID NOs: 39, 40, and 41, respectively, can be used as the GPC3-targeting drug of the present invention. The humanized anti-GPC3 antibody can be prepared using, as templates for humanization, appropriately selected human framework sequences having high sequence identity to a heavy chain framework sequence represented by SEQ ID NO: 42 or a light chain framework sequence represented by SEQ ID NO: 43.

In a further alternative non-limiting aspect, a humanized anti-GPC3 antibody comprising a heavy chain variable region selected from the group of heavy chain variable regions represented by SEQ ID NOs: 44, 45, 46, 47, 48, 49, and 50 and a light chain variable region represented by SEQ ID NO: 51 can be used as the GPC3-targeting drug of the present invention. In a further alternative non-limiting aspect, a humanized anti-GPC3 antibody comprising a heavy chain variable region selected from the group of heavy chain variable regions represented by SEQ ID NOs: 44, 45, 46, 47, 48, 49, and 50 and a light chain variable region selected from the group of light chain variable regions represented by SEQ ID NOs: 52, 53, 54, 55, 56, 57, 58, 59, 60, 61, 62, 63, 64, 65, and 66 can be used as the GPC3-targeting drug of the present invention.

In a further alternative non-limiting aspect, a humanized anti-GPC3 antibody comprising a heavy chain variable region represented by SEQ ID NO: 67 and a light chain variable region represented by SEQ ID NO: 68, a humanized anti-GPC3 antibody comprising a heavy chain variable region represented by SEQ ID NO: 69 and a light chain variable region represented by SEQ ID NO: 70, a humanized anti-GPC3 antibody comprising a heavy chain variable region represented by SEQ ID NO: 71 and a light chain variable region represented by SEQ ID NO: 72, or a humanized anti-GPC3 antibody comprising a heavy chain variable region represented by SEQ ID NO: 71 and a light chain variable region represented by SEQ ID NO: 73 can also be used as the GPC3-targeting drug of the present invention.

Cytotoxic Activity

Alternative examples of the anti-GPC3 antibody of the present invention include an anti-GPC3 antibody having cytotoxic activity. In the present invention, non-limiting examples of the cytotoxic activity include antibody-dependent cell-mediated cytotoxicity or antibody-dependent cellular cytotoxicity (ADCC) activity, complement-dependent cytotoxicity (CDC) activity, and cytotoxic activity based on T cells. In the present invention, the CDC activity means cytotoxic activity brought about by the complement system. On the other hand, the ADCC activity means the activity of damaging target cells by, for example, immunocytes, through the binding of the immunocytes via Fcγ receptors expressed on the immunocytes to the Fc regions of antigen-binding molecules comprising antigen-binding domains capable of binding to membrane molecules expressed on the cell membranes of the target cells. Whether or not the antigen-binding molecule of interest has ADCC activity or has CDC activity can be determined by a method known in the art (e.g., Current protocols in Immunology, Chapter 7. Immunologic studies in humans, Coligan et al., ed. (1993)).

Specifically, effector cells, a complement solution, and target cells are first prepared.

(1) Preparation of Effector Cells

The spleens are excised from CBA/N mice or the like, and spleen cells are separated therefrom in an RPMI1640 medium (Invitrogen Corp.). The spleen cells can be washed with this medium containing 10% fetal bovine serum (FBS, HyClone Laboratories, Inc.) and then concentration-adjusted to $5 \times 10^6$ cells/mL to prepare the effector cells.

(2) Preparation of Complement Solution

Baby Rabbit Complement (CEDARLANE Laboratories Ltd.) can be diluted 10-fold with a medium (Invitrogen Corp.) containing 10% FBS to prepare the complement solution.

(3) Preparation of Target Cells

Antigen-expressing cells can be cultured at 37° C. for 1 hour, together with 0.2 mCi $^{51}$Cr-sodium chromate (GE Healthcare Bio-Sciences Corp.), in a DMEM medium containing 10% FBS to thereby radiolabel the target cells. The cells thus radiolabeled can be washed three times with an RPMI1640 medium containing 10% FBS and then concentration-adjusted to $2 \times 10^5$ cells/mL to prepare the target cells.

The ADCC or CDC activity can be assayed by a method described below. For the ADCC activity assay, the target cells and the antigen-binding molecule (each 50 μl/well) are added to a U-bottom 96-well plate (Becton, Dickinson and Company) and reacted for 15 minutes on ice. Then, 100 μl of the effector cells is added to each well, and the plate is left standing for 4 hours in a $CO_2$ incubator. The final concentration of the antibody (antigen-binding molecule) can be set to, for example, 0 or 10 μg/ml. The radioactivity of 100 μl of the supernatant recovered from each well of the plate thus left standing is measured using a gamma counter (COBRA II AUTO-GAMMA, MODEL D5005, Packard Instrument Company). The cytotoxic activity (%) can be calculated on the basis of the calculation expression $(A-C)/(B-C) \times 100$ using the measurement value, wherein A represents radioactivity (cpm) from each sample; B represents radioactivity (cpm) from a sample supplemented with 1% NP-40 (Nacalai Tesque, Inc.); and C represents radioactivity (cpm) from a sample containing only the target cells.

For the CDC activity assay, the target cells and the antigen-binding molecule (each 50 μl/well) are added to a flat-bottomed 96-well plate (Becton, Dickinson and Company) and reacted for 15 minutes on ice. Then, 100 μl of the complement solution is added to each well, and the plate is left standing for 4 hours in a $CO_2$ incubator. The final concentration of the antibody (antigen-binding molecule) can be set to, for example, 0 or 3 μg/ml. The radioactivity of 100 μl of the supernatant recovered from each well of the plate thus left standing is measured using a gamma counter. The cytotoxic activity based on the CDC activity can be calculated in the same way as in the ADCC activity assay.

Cytotoxic Substance

In a non-limiting aspect, alternative examples of the anti-GPC3 antibody of the present invention include an anti-GPC3 antibody conjugated with a cytotoxic substance. Such an anti-GPC3 antibody-drug conjugate (ADC) is specifically disclosed in, for example, WO2007/137170, though the conjugate of the present invention is not limited to those described therein. Specifically, the cytotoxic substance may be any of chemotherapeutic agents listed below or may be a compound disclosed in Alley et al. (Curr. Opin. Chem. Biol. (2010) 14, 529-537) or WO2009/140242. Antigen-binding molecules are conjugated with these compounds via appropriate linkers or the like.

Examples of chemotherapeutic agents that may be conjugated to the anti-GPC3 antibody of the present invention can include the following: azaribine, anastrozole, azacytidine, bleomycin, bortezomib, bryostatin-1, busulfan, camptothecin, 10-hydroxycamptothecin, carmustine, Celebrex, chlorambucil, cisplatin, irinotecan, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin, ethinyl estradiol, estramustine, etoposide, etoposide glucuronide, floxuridine, fludarabine, flutamide, fluorouracil, fluoxymesterone, gemcitabine, hydroxyprogesterone caproate, hydroxyurea, idarubicin, ifosfamide, leucovorin, lomustine, maytansinoid, mechlorethamine, medroxyprogesterone acetate, megestrol acetate, melphalan, mercaptopurine, methotrexate, mitoxantrone, mithramycin, mitomycin, mitotane, phenylbutyrate, prednisone, procarbazine, paclitaxel, pentostatin, semustine, streptozocin, tamoxifen, taxanes, Taxol, testosterone propionate, thalidomide, thioguanine, thiotepa, teniposide, topotecan, uracil mustard, vinblastine, vinorelbine, and vincristine.

In the present invention, a preferred chemotherapeutic agent is a low-molecular-weight chemotherapeutic agent. The low-molecular-weight chemotherapeutic agent is unlikely to interfere with the functions of the anti-GPC3 antibody even after forming the anti-GPC3 antibody-drug conjugate of the present invention. In the present invention, the low-molecular-weight chemotherapeutic agent has a molecular weight of usually 100 to 2000, preferably 200 to 1000. All of the chemotherapeutic agents listed herein are low-molecular-weight chemotherapeutic agents. These chemotherapeutic agents according to the present invention include prodrugs that are converted to active chemotherapeutic agents in vivo. The prodrugs may be activated through enzymatic conversion or nonenzymatic conversion.

Alternative examples of the conjugated cytotoxic substance in the anti-GPC3 antibody-drug conjugate of the present invention can include toxic peptides (toxins) such as *Pseudomonas* exotoxin A, saporin-s6, diphtheria toxin, and cnidarian toxin, radioiodine, and photosensitizers. Examples of the toxic peptides preferably include the following:

diphtheria toxin A chain (Langone et al., Methods in Enzymology (1983) 93, 307-308);

*Pseudomonas* exotoxin (Nature Medicine (1996) 2, 350-353); ricin A chain (Fulton et al., J. Biol. Chem. (1986) 261, 5314-5319; Sivam et al., Cancer Res. (1987) 47, 3169-3173; Cumber et al., J. Immunol. Methods (1990) 135, 15-24; Wawrzynczak et al., Cancer Res. (1990) 50, 7519-7562; and Gheeite et al., J. Immunol. Methods (1991) 142, 223-230);

deglycosylated ricin A chain (Thorpe et al., Cancer Res. (1987) 47, 5924-5931);

abrin A chain (Wawrzynczak et al., Br. J. Cancer (1992) 66, 361-366; Wawrzynczak et al., Cancer Res. (1990) 50, 7519-7562; Sivam et al., Cancer Res. (1987) 47, 3169-3173; and Thorpe et al., Cancer Res. (1987) 47, 5924-5931);

gelonin (Sivam et al., Cancer Res. (1987) 47, 3169-3173; Cumber et al., J. Immunol. Methods (1990) 135, 15-24; Wawrzynczak et al., Cancer Res., (1990) 50, 7519-7562; and Bolognesi et al., Clin. exp. Immunol. (1992) 89, 341-346);

pokeweed anti-viral protein from seeds (PAP-s) (Bolognesi et al., Clin. exp. Immunol. (1992) 89, 341-346); bryodin (Bolognesi et al., Clin. exp. Immunol. (1992) 89, 341-346);

saporin (Bolognesi et al., Clin. exp. Immunol. (1992) 89, 341-346);

momordin (Cumber et al., J. Immunol. Methods (1990) 135, 15-24; Wawrzynczak et al., Cancer Res. (1990) 50, 7519-7562; and Bolognesi et al., Clin. exp. Immunol. (1992) 89, 341-346);

momorcochin (Bolognesi et al., Clin. exp. Immunol. (1992) 89, 341-346);

dianthin 32 (Bolognesi et al., Clin. exp. Immunol. (1992) 89, 341-346);

dianthin 30 (Stirpe F., Barbieri L., FEBS letter (1986) 195, 1-8);

modeccin (Stirpe F., Barbieri L., FEBS letter (1986) 195, 1-8);

viscumin (Stirpe F., Barbieri L., FEBS letter (1986) 195, 1-8);

volkensin (Stirpe F., Barbieri L., FEBS letter (1986) 195, 1-8);

dodecandrin (Stirpe F., Barbieri L., FEBS letter (1986) 195, 1-8);

tritin (Stirpe F., Barbieri L., FEBS letter (1986) 195, 1-8);

luffin (Stirpe F., Barbieri L., FEBS letter (1986) 195, 1-8); and trichokirin (Casellas et al., Eur. J. Biochem. (1988) 176, 581-588; and Bolognesi et al., Clin. exp. Immunol., (1992) 89, 341-346).

In the case of assaying the cytotoxic activity of the anti-GPC3 antibody-drug conjugate of the present invention, the target cells and the anti-GPC3 antibody-drug conjugate (each 50 µl/well) are added to a flat-bottomed 96-well plate (Becton, Dickinson and Company) and reacted for 15 minutes on ice. The plate is incubated for 1 to 4 hours in a $CO_2$ incubator. The anti-GPC3 antibody-drug conjugate can be appropriately used at a final concentration ranging from 0 to 3 µg/ml. After the culture, 100 µl of the supernatant is recovered from each well, and the radioactivity of the supernatant is measured using a gamma counter. The cytotoxic activity can be calculated in the same way as in the ADCC activity assay.

Fc Region

An Fc region contained in a constant region contained in the anti-GPC3 antibody of the present invention may be obtained from human IgG, though the Fc region of the present invention is not limited by a particular subclass of IgG. The Fc region refers to an antibody heavy chain constant region comprising a hinge region and CH2 and CH3 domains from the hinge region N terminus which is a papain cleavage site (about amino acid 216 based on the EU numbering). Preferred examples of the Fc region include Fc regions having binding activity against Fcγ receptors as mentioned later. In a non-limiting aspect, examples of such Fc regions include Fc regions contained in constant regions represented by SEQ ID NO: 74 for human IgG1, SEQ ID NO: 75 for IgG2, SEQ ID NO: 76 for IgG3, and SEQ ID NO: 77 for IgG4.

Fcγ Receptor (FcγR)

The Fcγ receptor (also referred to as FcγR) refers to a receptor capable of binding to the Fc region of an IgG1, IgG2, IgG3, or IgG4 monoclonal antibody and substantially means even any member of protein family encoded by Fcγ receptor genes. In humans, this family includes, but not limited to: FcγRI (CD64) including isoforms FcγRIa, FcγRIb, and FcγRIc; FcγRII (CD32) including isoforms FcγRIIa (including allotypes H131 and R131; i.e., FcγRIIa (H) and FcγRIIa (R)), FcγRIIb (including FcγRIIb-1 and FcγRIIb-2), and FcγRIIc; FcγRIII (CD16) including isoforms FcγRIIIa (including allotypes V158 and F158; i.e., FcγRIIIa (V) and FcγRIIIa (F)) and FcγRIIIb (including allotypes FcγRIIIb-NA1 and FcγRIIIb-NA2); and even any unfound human FcγR or FcγR isoform or allotype. FcγR includes human, mouse, rat, rabbit, and monkey Fcγ receptors. The FcγR of the present invention is not limited to these receptors and may be derived from any organism. The mouse FcγR includes, but not limited to, FcγRI (CD64), FcγRII (CD32), FcγRIII (CD16), and FcγRIII-2 (FcγRIV, CD16-2), and even any unfound mouse FcγR or FcγR isoform or allotype. Preferred examples of such Fcγ receptors include human FcγRI (CD64), FcγRIIa (CD32), FcγRIIb (CD32), FcγRIIIa (CD16), and/or FcγRIIIb (CD16). The polypeptide sequence of human FcγRI is described in SEQ ID NO: 78 (NP_000557.1); the polypeptide sequence of human FcγRIIa (allotype H131) is described in SEQ ID NO: 79 (AAH20823.1) (allotype R131 has a sequence with substitution by Arg at amino acid 166 in SEQ ID NO: 79); the polypeptide sequence of FcγRIIb is described in SEQ ID NO: 80 (AAI46679.1); the polypeptide sequence of FcγRIIIa is described in SEQ ID NO: 81 (AAH33678.1); and the polypeptide sequence of FcγRIIIb is described in SEQ ID NO: 82 (AAI28563.1) (registration numbers of a database such as RefSeq are shown within the parentheses). Whether or not the Fcγ receptor has binding activity against the Fc region of an IgG1, IgG2, IgG3, or IgG4 monoclonal antibody can be confirmed by a method known in the art such as FACS or ELISA formats as well as BIACORE method using amplified luminescent proximity homogeneous assay (ALPHA) screening or surface plasmon resonance (SPR) phenomena (Proc. Natl. Acad. Sci. U.S.A. (2006) 103 (11), 4005-4010).

In FcγRI (CD64) including isoforms FcγRIa, FcγRIb, and FcγRIc and FcγRIII (CD16) including isoforms FcγRIIIa (including allotypes V158 and F158) and FcγRIIIb (including allotypes FcγRIIIb-NA1 and FcγRIIIb-NA2), an α chain capable of binding to the IgG Fc region associates with a common γ chain having ITAM that transduces activating signals into cells. On the other hand, FcγRII (CD32) including isoforms FcγRIIa (including allotypes H131 and R131) and FcγRIIc contains ITAM in its cytoplasmic domain. These receptors are expressed in many immunocytes, such as macrophages, mast cells, and antigen-displaying cells. These receptors bind to IgG Fc regions and thereby transduce activating signals, which in turn promote the phagocytic capacity of macrophages, the production of inflammatory cytokines, the degranulation of mast cells, and the increased function of antigen-displaying cells. The Fcγ receptors that are able to transduce activating signals as described above are referred to as active Fcγ receptors herein.

On the other hand, FcγRIIb (including FcγRIIb-1 and FcγRIIb-2) contains ITIM that transduces inhibitory signals, in its intracytoplasmic domain. In B cells, activating signals from B cell receptors (BCRs) are inhibited by the cross-linking of BCR with FcγRIIb, resulting in the suppressed antibody production of BCR. The phagocytic capacity of macrophages or their ability to produce inflammatory cytokines is suppressed by the cross-linking of FcγRIII and FcγRIIb. The Fcγ receptors that are able to transduce inhibitory signals as described above are referred to as inhibitory Fcγ receptors herein.

Binding Activity of Fc Region Against FcγR

As mentioned above, examples of the Fc region contained in the anti-GPC3 antibody of the present invention include Fc regions having binding activity against Fcγ receptors. In a non-limiting aspect, examples of such Fc regions include Fc regions contained in constant regions represented by SEQ ID NO: 74 for human IgG1, SEQ ID NO: 75 for IgG2, SEQ ID NO: 76 for IgG3, and SEQ ID NO: 77 for IgG4. Whether or not the Fcγ receptor has binding activity against the Fc region of an IgG1, IgG2, IgG3, or IgG4 monoclonal antibody can be confirmed by a method known in the art such as FACS or ELISA formats as well as BIACORE method using amplified luminescent proximity homogeneous assay (ALPHA) screening or surface plasmon resonance (SPR) phenomena (Proc. Natl. Acad. Sci. U.S.A. (2006) 103 (11), 4005-4010).

The ALPHA screening is carried out on the basis of the following principles according to ALPHA technology using two beads, a donor and an acceptor. Luminescence signals are detected only when these two beads are located in proximity through the biological interaction between a molecule bound with the donor bead and a molecule bound with the acceptor bead. A laser-excited photosensitizer in the donor bead converts ambient oxygen to singlet oxygen in an excited state. The singlet oxygen diffuses around the donor bead and reaches the acceptor bead located in proximity thereto to thereby cause chemiluminescent reaction in the bead, which finally emits light. In the absence of the interaction between the molecule bound with the donor bead and the molecule bound with the acceptor bead, singlet oxygen produced by the donor bead does not reach the acceptor bead. Thus, no chemiluminescent reaction occurs.

For example, a biotin-labeled anti-GPC3 antibody comprising the Fc region is bound to the donor bead, while a glutathione S transferase (GST)-tagged Fcγ receptor is bound to the acceptor bead. In the absence of a competing anti-GPC3 antibody comprising a modified Fc region, the anti-GPC3 antibody having the native Fc region interacts with the Fcγ receptor to generate signals of 520 to 620 nm. An anti-GPC3 antibody comprising an untagged modified Fc region competes with the anti-GPC3 antibody having the native Fc region for the interaction with the Fcγ receptor. Decrease in fluorescence caused as a result of the competition can be quantified to thereby determine relative binding affinity. The antibody biotinylation using sulfo-NHS-biotin or the like is known in the art. The Fcγ receptor can be tagged with GST by an appropriately adopted method which involves, for example: fusing a polynucleotide encoding the Fcγ receptor in flame with a polynucleotide encoding GST; operably ligating the resulting fusion gene with a vector; and allowing cells or the like carrying the vector to express the GST-tagged Fcγ receptor, which is then purified using a glutathione column. The obtained signals are preferably analyzed using, for example, software GRAPHPAD PRISM (GraphPad Software, Inc., San Diego) adapted to a one-site competition model based on nonlinear regression analysis.

One (ligand) of the substances between which the interaction is to be observed is immobilized on a thin gold film of a sensor chip. The sensor chip is irradiated with light from the back such that total reflection occurs at the interface between the thin gold film and glass. As a result, a site having a drop in reflection intensity (SPR signal) is formed in a portion of reflected light. The other (analyte) of the substances between which the interaction is to be observed is flowed on the surface of the sensor chip and bound to the ligand so that the mass of the immobilized ligand molecule is increased to change the refractive index of the solvent on the sensor chip surface. This change in the refractive index shifts the position of the SPR signal (on the contrary, the dissociation of the bound molecules gets the signal back to the original position). The Biacore system plots on the ordinate the amount of the shift, i.e., change in mass on the sensor chip surface, and displays time-dependent change in mass as assay data (sensorgram). Kinetics: an association rate constant (ka) and a dissociation rate constant (kd) can be determined from the curve of the sensorgram, and affinity (KD) can be determined from the ratio between these constants. Inhibition assay is also preferably used in the BIACORE method. Examples of the inhibition assay are described in Lazor et al. (Proc. Natl. Acad. Sci. U.S.A. (2006) 103 (11), 4005-4010).

Fcγ Receptor (FcγR)-Binding Modified Fc Region

In addition to the Fc regions contained in constant regions represented by SEQ ID NO: 74 for human IgG1, SEQ ID NO: 75 for IgG2, SEQ ID NO: 76 for IgG3, and SEQ ID NO: 77 for IgG4, an FcγR-binding modified Fc region having higher binding activity against Fcγ receptors than that of the Fc region of native human IgG against Fcγ receptors may be appropriately used as the Fc region contained in the anti-GPC3 antibody of the present invention. The "Fc region of native human IgG" described herein means an Fc region having a fucose-containing sugar chain as a sugar chain bound to position 297 (EU numbering) of the Fc region contained in the human IgG1, IgG2, IgG3, or IgG4 constant region represented by SEQ ID NO: 74, 75, 76, or 77. Such an FcγR-binding modified Fc region can be prepared by the amino acid modification of the native human IgG Fc region. Whether or not the FcγR-binding modified Fc region has higher binding activity against FcγR than that of the native human IgG Fc region against FcγR can be appropriately confirmed by a method known in the art such as FACS or ELISA formats as well as BIACORE method using amplified luminescent proximity homogeneous assay (ALPHA) screening or surface plasmon resonance (SPR) phenomena as described above.

In the present invention, the "modification of amino acid(s)" or "amino acid modification" of the Fc region includes modification to an amino acid sequence different from the amino acid sequence of the starting Fc region. Any Fc region can be used as the starting Fc region as long as the modified form of the starting Fc region can bind to the human Fcγ receptor in a neutral region of pH. Alternatively, an Fc region further modified from an already modified Fc region as the starting Fc region may be preferably used as the Fc region of the present invention. The starting Fc region may mean the polypeptide itself, a composition containing the starting Fc region, or an amino acid sequence encoding the starting Fc region. The starting Fc region can include Fc regions known in the art produced by recombination reviewed in the paragraph about the antibody. The starting Fc region is not limited by its origin and can be obtained from an arbitrary nonhuman animal organism or a human. Preferred examples of the arbitrary organism include an organism selected from mice, rats, guinea pigs, hamsters, gerbils, cats, rabbits, dog, goats, sheep, cattle, horses, camels, and nonhuman primates. In another aspect, the starting Fc region may be obtained from a cynomolgus monkey, a marmoset, a rhesus monkey, a chimpanzee, or a human. Preferably, the starting Fc region can be obtained from human IgG1, though the starting Fc region of the present invention is not limited by a particular class of IgG. This means that the Fc region of human IgG1, IgG2, IgG3, or IgG4 can be appropriately used as the starting Fc region. Likewise, this means herein that the Fc region of arbitrary IgG class or subclass from the arbitrary organism can be preferably used as the starting Fc region. Examples of variants of naturally occurring IgG or manipulated forms thereof are described in literatures known in the art (Curr. Opin. Biotechnol. (2009) 20 (6), 685-91; Curr. Opin. Immunol. (2008) 20 (4), 460-470; Protein Eng. Des. Sel. (2010) 23 (4), 195-202; and International Publication Nos. WO2009/086320, WO2008/092117, WO2007/041635, and WO2006/105338), though the variants or the manipulated forms of the present invention are not limited to those described therein.

Examples of the modification include one or more variations, for example, a variation that substitutes amino acid(s) in the starting Fc region by amino acid residue(s) different therefrom, the insertion of one or more amino acid residues into the amino acid sequence of the starting Fc region, and/or the deletion of one or more amino acids from the amino acid sequence of the starting Fc region. Preferably, the amino acid sequence of the Fc region thus modified comprises an amino acid sequence containing at least a nonnatural portion of the Fc region. Such a variant inevitably has less than 100% sequence identity or similarity to the starting Fc region. In a preferred embodiment, the variant has an amino acid sequence with approximately 75% to less than 100% sequence identity or similarity, more preferably approximately 80% to less than 100%, further preferably approximately 85% to less than 100%, still further preferably approximately 90% to less than 100%, most preferably approximately 95% to less than 100% sequence identity or similarity to the amino acid sequence of the starting Fc region. In a non-limiting aspect of the present invention, the starting Fc region and the FcγR-binding modified Fc region of the present invention differ by at least one amino acid. The difference in amino acid between the starting Fc region and the FcγR-binding modified Fc region of the present invention may be preferably determined by a difference in amino acid with the identified position of its amino acid residue defined particularly by the EU numbering.

The amino acid(s) in the Fc region can be modified by an appropriately adopted method known in the art such as site-directed mutagenesis (Kunkel et al., Proc. Natl. Acad. Sci. USA (1985) 82, 488-492) or overlap extension PCR. Also, a plurality of methods known in the art can be adopted as methods for modifying an amino acid to substitute the amino acid by an amino acid other than natural one (Annu. Rev. Biophys. Biomol. Struct. (2006) 35, 225-249; and Proc. Natl. Acad. Sci. U.S.A. (2003) 100 (11), 6353-6357). For example, a tRNA-containing cell-free translation system (Clover Direct (Protein Express, an R & D oriented company)) comprising a non-natural amino acid bound with an amber suppressor tRNA complementary to UAG codon (amber codon), which is a stop codon, is also preferably used.

The FcγR-binding modified Fc region (contained in the antigen-binding molecule of the present invention) having higher binding activity against Fcγ receptors than that of the native human IgG Fc region against Fcγ receptors can be obtained by any method. Specifically, the FcγR-binding modified Fc region can be obtained by the amino acid modification of a human IgG immunoglobulin Fc region used as the starting Fc region. Examples of the IgG immunoglobulin Fc region preferred for the modification include Fc regions contained in human IgG (IgG1, IgG2, IgG3, and IgG4, and modified forms thereof) constant regions represented by SEQ ID NOs: 74, 75, 76, and 77.

The modification to other amino acids can include amino acid modification at any position as long as the resulting Fc region has higher binding activity against Fcγ receptors than that of the native human IgG Fc region against Fcγ receptors. When the antigen-binding molecule contains a human IgG1 Fc region as a human Fc region, the modification preferably allows the Fc region to contain a fucose-containing sugar chain as a sugar chain bound to position 297 (EU numbering) and is effective for producing higher binding activity against Fcγ receptors than that of the native human IgG Fc region against Fcγ receptors. Such amino acid modification has been reported in, for example, International Publication Nos. WO2007/024249, WO2007/021841, WO2006/031370, WO2000/042072, WO2004/029207, WO2004/099249, WO2006/105338, WO2007/041635, WO2008/092117, WO2005/070963, WO2006/020114, WO2006/116260, and WO2006/023403.

Examples of amino acids that may undergo such modification include at least one or more amino acids selected from the group consisting of
position 221, position 222, position 223, position 224, position 225, position 227, position 228, position 230, position 231, position 232, position 233, position 234, position 235, position 236, position 237, position 238, position 239, position 240, position 241, position 243, position 244, position 245, position 246, position 247, position 249, position 250, position 251, position 254, position 255, position 256, position 258, position 260, position 262, position 263, position 264, position 265, position 266, position 267, position 268, position 269, position 270, position 271, position 272, position 273, position 274, position 275, position 276, position 278, position 279, position 280, position 281, position 282, position 283, position 284, position 285, position 286, position 288, position 290, position 291, position 292, position 293, position 294, position 295, position 296, position 297, position 298, position 299, position 300, position 301, position 302, position 303, position 304, position 305, position 311, position 313, position 315, position 317, position 318, position 320, position 322, position 323, position 324, position 325, position 326, position 327, position 328, position 329, position 330, position 331, position 332, position 333, position 334, position 335, position 336, position 337, position 339, position 376, position 377, position 378, position 379, position 380, position 382, position 385, position 392, position 396, position 421, position 427, position 428, position 429, position 434, position 436 and position 440 based on the EU numbering. The modification of these amino acids can yield the Fc region (FcγR-binding modified Fc region) having higher binding activity against Fcγ receptors than that of the native human IgG Fc region against Fcγ receptors.

Examples of particularly preferred modification for use in the present invention include at least one or more amino acid modifications selected from the group consisting of modifications of
amino acid 221 to Lys or Tyr,
amino acid 222 to Phe, Trp, Glu, or Tyr,
amino acid 223 to Phe, Trp, Glu, or Lys,
amino acid 224 to Phe, Trp, Glu, or Tyr,
amino acid 225 to Glu, Lys, or Trp,
amino acid 227 to Glu, Gly, Lys, or Tyr,
amino acid 228 to Glu, Gly, Lys, or Tyr,
amino acid 230 to Ala, Glu, Gly, or Tyr,
amino acid 231 to Glu, Gly, Lys, Pro, or Tyr,
amino acid 232 to Glu, Gly, Lys, or Tyr,
amino acid 233 to Ala, Asp, Phe, Gly, His, Ile, Lys, Leu, Met, Asn, Gln, Arg, Ser, Thr, Val, Trp, or Tyr,
amino acid 234 to Ala, Asp, Glu, Phe, Gly, His, Ile, Lys, Met, Asn, Pro, Gln, Arg, Ser, Thr, Val, Trp, or Tyr,
amino acid 235 to Ala, Asp, Glu, Phe, Gly, His, Ile, Lys, Met, Asn, Pro, Gln, Arg, Ser, Thr, Val, Trp, or Tyr,
amino acid 236 to Ala, Asp, Glu, Phe, His, Ile, Lys, Leu, Met, Asn, Pro, Gln, Arg, Ser, Thr, Val, Trp, or Tyr,
amino acid 237 to Asp, Glu, Phe, His, Ile, Lys, Leu, Met, Asn, Pro, Gln, Arg, Ser, Thr, Val, Trp, or Tyr,
amino acid 238 to Asp, Glu, Phe, Gly, His, Ile, Lys, Leu, Met, Asn, Gln, Arg, Ser, Thr, Val, Trp, or Tyr,
amino acid 239 to Asp, Glu, Phe, Gly, His, Ile, Lys, Leu, Met, Asn, Pro, Gln, Arg, Thr, Val, Trp, or Tyr,
amino acid 240 to Ala, Ile, Met, or Thr,
amino acid 241 to Asp, Glu, Leu, Arg, Trp, or Tyr,
amino acid 243 to Leu, Glu, Leu, Gln, Arg, Trp, or Tyr,
amino acid 244 to His,
amino acid 245 to Ala,
amino acid 246 to Asp, Glu, His, or Tyr,
amino acid 247 to Ala, Phe, Gly, His, Ile, Leu, Met, Thr, Val, or Tyr,
amino acid 249 to Glu, His, Gln, or Tyr,
amino acid 250 to Glu, or Gln,
amino acid 251 to Phe,
amino acid 254 to Phe, Met, or Tyr,
amino acid 255 to Glu, Leu, or Tyr, amino acid 256 to Ala, Met, or Pro,
amino acid 258 to Asp, Glu, His, Ser, or Tyr,
amino acid 260 to Asp, Glu, His, or Tyr,
amino acid 262 to Ala, Glu, Phe, Ile, or Thr,
amino acid 263 to Ala, Ile, Met, or Thr,
amino acid 264 to Asp, Glu, Phe, Gly, His, Ile, Lys, Leu, Met, Asn, Pro, Gln, Arg, Ser, Thr, Trp, or Tyr,
amino acid 265 to Ala, Leu, Phe, Gly, His, Ile, Lys, Leu, Met, Asn, Pro, Gln, Arg, Ser, Thr, Val, Trp, or Tyr,
amino acid 266 to Ala, Ile, Met, or Thr,
amino acid 267 to Asp, Glu, Phe, His, Ile, Lys, Leu, Met, Asn, Pro, Gln, Arg, Thr, Val, Trp, or Tyr,
amino acid 268 to Asp, Glu, Phe, Gly, Ile, Lys, Leu, Met, Pro, Gln, Arg, Thr, Val, or Trp,
amino acid 269 to Phe, Gly, His, Ile, Lys, Leu, Met, Asn, Pro, Arg, Ser, Thr, Val, Trp, or Tyr,
amino acid 270 to Glu, Phe, Gly, His, Ile, Leu, Met, Pro, Gln, Arg, Ser, Thr, Trp, or Tyr,
amino acid 271 to Ala, Asp, Glu, Phe, Gly, His, Ile, Lys, Leu, Met, Asn, Gln, Arg, Ser, Thr, Val, Trp, or Tyr,
amino acid 272 to Asp, Phe, Gly, His, Ile, Lys, Leu, Met, Pro, Arg, Ser, Thr, Val, Trp, or Tyr,
amino acid 273 to Phe, or Ile,
amino acid 274 to Asp, Glu, Phe, Gly, His, Ile, Leu, Met, Asn, Pro, Arg, Ser, Thr, Val, Trp, or Tyr,
amino acid 275 to Leu, or Trp,
amino acid 276 to Asp, Glu, Phe, Gly, His, Ile, Leu, Met, Pro, Arg, Ser, Thr, Val, Trp, or Tyr,
amino acid 278 to Asp, Glu, Gly, His, Ile, Lys, Leu, Met, Asn, Pro, Gln, Arg, Ser, Thr, Val, or Trp,
amino acid 279 to Ala,
amino acid 280 to Ala, Gly, His, Lys, Leu, Pro, Gln, Trp, or Tyr,
amino acid 281 to Asp, Lys, Pro, or Tyr,
amino acid 282 to Glu, Gly, Lys, Pro, or Tyr,
amino acid 283 to Ala, Gly, His, Ile, Lys, Leu, Met, Pro, Arg, or Tyr,
amino acid 284 to Asp, Glu, Leu, Asn, Thr, or Tyr,
amino acid 285 to Asp, Glu, Lys, Gln, Trp, or Tyr,
amino acid 286 to Glu, Gly, Pro, or Tyr,
amino acid 288 to Asn, Asp, Glu, or Tyr,
amino acid 290 to Asp, Gly, His, Leu, Asn, Ser, Thr, Trp, or Tyr,
amino acid 291 to Asp, Glu, Gly, His, Ile, Gln, or Thr,
amino acid 292 to Ala, Asp, Glu, Pro, Thr, or Tyr,
amino acid 293 to Phe, Gly, His, Ile, Leu, Met, Asn, Pro, Arg, Ser, Thr, Val, Trp, or Tyr,
amino acid 294 to Phe, Gly, His, Ile, Lys, Leu, Met, Asn, Pro, Arg, Ser, Thr, Val, Trp, or Tyr,
amino acid 295 to Asp, Glu, Phe, Gly, His, Ile, Lys, Met, Asn, Pro, Arg, Ser, Thr, Val, Trp, or Tyr,
amino acid 296 to Ala, Asp, Glu, Gly, His, Ile, Lys, Leu, Met, Asn, Gln, Arg, Ser, Thr, or Val,
amino acid 297 to Asp, Glu, Phe, Gly, His, Ile, Lys, Leu, Met, Pro, Gln, Arg, Ser, Thr, Val, Trp, or Tyr,
amino acid 298 to Ala, Asp, Glu, Phe, His, Ile, Lys, Met, Asn, Gln, Arg, Thr, Val, Trp, or Tyr,
amino acid 299 to Ala, Asp, Glu, Phe, Gly, His, Ile, Lys, Leu, Met, Asn, Pro, Gln, Arg, Ser, Val, Trp, or Tyr,
amino acid 300 to Ala, Asp, Glu, Gly, His, Ile, Lys, Leu, Met, Asn, Pro, Gln, Arg, Ser, Thr, Val, or Trp,
amino acid 301 to Asp, Glu, His, or Tyr,
amino acid 302 to Ile,
amino acid 303 to Asp, Gly, or Tyr,
amino acid 304 to Asp, His, Leu, Asn, or Thr,
amino acid 305 to Glu, Ile, Thr, or Tyr,
amino acid 311 to Ala, Asp, Asn, Thr, Val, or Tyr,
amino acid 313 to Phe,
amino acid 315 to Leu,
amino acid 317 to Glu or Gln,
amino acid 318 to His, Leu, Asn, Pro, Gln, Arg, Thr, Val, or Tyr,
amino acid 320 to Asp, Phe, Gly, His, Ile, Leu, Asn, Pro, Ser, Thr, Val, Trp, or Tyr,
amino acid 322 to Ala, Asp, Phe, Gly, His, Ile, Pro, Ser, Thr, Val, Trp, or Tyr,
amino acid 323 to Ile,
amino acid 324 to Asp, Phe, Gly, His, Ile, Leu, Met, Pro, Arg, Thr, Val, Trp, or Tyr,
amino acid 325 to Ala, Asp, Glu, Phe, Gly, His, Ile, Lys, Leu, Met, Pro, Gln, Arg, Ser, Thr, Val, Trp, or Tyr,
amino acid 326 to Ala, Asp, Glu, Gly, Ile, Leu, Met, Asn, Pro, Gln, Ser, Thr, Val, Trp, or Tyr,
amino acid 327 to Ala, Asp, Glu, Phe, Gly, His, Ile, Lys, Leu, Met, Asn, Pro, Arg, Thr, Val, Trp, or Tyr,
amino acid 328 to Ala, Asp, Glu, Phe, Gly, His, Ile, Lys, Met, Asn, Pro, Gln, Arg, Ser, Thr, Val, Trp, or Tyr,
amino acid 329 to Asp, Glu, Phe, Gly, His, Ile, Lys, Leu, Met, Asn, Gln, Arg, Ser, Thr, Val, Trp, or Tyr,
amino acid 330 to Cys, Glu, Phe, Gly, His, Ile, Lys, Leu, Met, Asn, Pro, Arg, Ser, Thr, Val, Trp, or Tyr,
amino acid 331 to Asp, Phe, His, Ile, Leu, Met, Gln, Arg, Thr, Val, Trp, or Tyr,
amino acid 332 to Ala, Asp, Glu, Phe, Gly, His, Lys, Leu, Met, Asn, Pro, Gln, Arg, Ser, Thr, Val, Trp, or Tyr,
amino acid 333 to Ala, Asp, Glu, Phe, Gly, His, Ile, Leu, Met, Pro, Ser, Thr, Val, or Tyr,
amino acid 334 to Ala, Glu, Phe, Ile, Leu, Pro, or Thr,
amino acid 335 to Asp, Phe, Gly, His, Ile, Leu, Met, Asn, Pro, Arg, Ser, Val, Trp, or Tyr,
amino acid 336 to Glu, Lys, or Tyr,
amino acid 337 to Glu, His, or Asn,
amino acid 339 to Asp, Phe, Gly, Ile, Lys, Met, Asn, Gln, Arg, Ser, or Thr,
amino acid 376 to Ala, or Val,
amino acid 377 to Gly, or Lys,
amino acid 378 to Asp,
amino acid 379 to Asn,
amino acid 380 to Ala, Asn, or Ser,
amino acid 382 to Ala, or Ile,
amino acid 385 to Glu,
amino acid 392 to Thr,
amino acid 396 to Leu,
amino acid 421 to Lys,
amino acid 427 to Asn,
amino acid 428 to Phe, or Leu,
amino acid 429 to Met,
amino acid 434 to Trp,
amino acid 436 to Ile, or
amino acid 440 to Gly, His, Ile, Leu, or Tyr based on the EU numbering in the Fc region. The number of amino acids to be modified is not limited. Only one amino acid may be modified, or two or more amino acids may be modified. Examples of combinations of amino acid modifications at two or more positions include combinations as described in Table 3 (Tables 3-1 to 3-3). Also, WO2007/047291 discloses specific examples of the anti-GPC3 antibody comprising the FcγR-binding modified Fc region having higher binding activity against Fcγ receptors than that of the native human IgG Fc region against Fcγ receptors.

TABLE 3-1

| Combination of amino acids | Combination of amino acids |
|---|---|
| K370E/P396L/D270E | S239Q/I332Q |
| Q419H/P396L/D270E | S267D/I332E |
| V240A/P396L/D270E | S267E/I332E |
| R255L/P396L/D270E | S267L/A327S |
| R255L/P396L/D270E | S267Q/A327S |
| R255L/P396L/D270E/R292G | S298A/I332E |
| R255L/P396L/D270E | S304T/I332E |
| R255L/P396L/D270E/Y300L | S324G/I332D |
| F243L/D270E/K392N/P396L | S324G/I332E |
| F243L/R255L/D270E/P396L | S324I/I332D |
| F243L/R292P/Y300L/V305I/P396L | S324I/I332E |
| F243L/R292P/Y300L/P396L | T260H/I332E |
| F243L/R292P/Y300L | T335D/I332E |
| F243L/R292P/P396L | V240I/V266I |
| F243L/R292P/V305I | V264I/I332E |
| F243L/R292P | D265F/N297E/I332E |
| S298A/E333A/K334A | D265Y/N297D/I332E |
| E380A/T307A | F243L/V262I/V264W |
| K326M/E333S | N297D/A330Y/I332E |
| K326A/E333A | N297D/T299E/I332E |
| S317A/K353A | N297D/T299F/I332E |
| A327D/I322E | N297D/T299H/I332E |
| A330L/I332E | N297D/T299I/I332E |
| A330Y/I332E | N297D/T299L/I332E |
| E258H/I332E | N297D/T299V/I332E |
| E272H/I332E | P230A/E233D/I332E |
| E272I/N276D | P244H/P245A/P247V |
| E272R/I332E | S239D/A330L/I332E |
| E283H/I332E | S239D/A330Y/I332E |
| E293R/I332E | S239D/H268E/A330Y |
| F241L/V262I | S239D/I322E/A327A |
| F241W/F243W | S239D/I332E/A330I |

TABLE 3-2

| F243L/V264I | S239D/N297D/I332E |
|---|---|
| H268D/A330Y | S239D/S298A/I332E |
| H268E/A330Y | S239D/V264I/I332E |
| K246H/I332E | S239E/N297D/I332E |
| L234D/I332E | S239E/V264I/I332E |
| L234E/I332E | S239N/A330L/I332E |
| L234G/I332E | S239N/A330Y/I332E |
| L234I/I332E | S239N/S298A/I332E |
| L234I/L235D | S239Q/V264I/I332E |
| L234Y/I332E | V264E/N297D/I332E |
| L235D/I332E | V264I/A330L/I332E |
| L235E/I332E | V264I/A330Y/I332E |
| L235I/I332E | V264I/S298A/I332E |
| L235S/I332E | Y296D/N297D/I332E |
| L328A/I332D | Y296E/N297D/I332E |
| L328D/I332D | Y296H/N297D/I332E |
| L328D/I332E | Y296N/N297D/I332E |
| L328E/I332D | Y296Q/N297D/I332E |
| L328E/I332E | Y296T/N297D/I332E |
| L328F/I332D | D265Y/N297D/T299L/I332E |
| L328F/I332E | F241E/F243Q/V262T/V264E |
| L328H/I332E | F241E/F243R/V262E/V264R |
| L328I/I332D | F241E/F243Y/V262T/V264R |
| L328I/I332E | F241L/F243L/V262I/V264I |
| L328M/I332D | F241R/F243Q/V262T/V264R |
| L328M/I332E | F241S/F243H/V262T/V264T |
| L328N/I332D | F241W/F243W/V262A/V264A |
| L328N/I332E | F241Y/F243Y/V262T/V264T |
| L328Q/I332D | I322E/A330Y/H268E/A327A |
| L328Q/I332E | N297D/I332E/S239D/A330L |
| L328T/I332D | N297D/S298A/A330Y/I332E |
| L328T/I332E | S239D/A330Y/I332E/K326E |
| L328V/I332D | S239D/A330Y/I332E/K326T |
| L328V/I332E | S239D/A330Y/I332E/L234I |
| L328Y/I332D | S239D/A330Y/I332E/L235D |

TABLE 3-3

| L328Y/I332E | S239D/A330Y/I332E/V240I |
|---|---|
| N297D/I332E | S239D/A330Y/I332E/V264T |
| N297E/I332E | S239D/A330Y/I332E/V266I |
| N297S/I332E | S239D/D265F/N297D/I332E |
| P227G/I332E | S239D/D265H/N297D/I332E |
| P230A/E233D | S239D/D265I/N297D/I332E |
| Q295E/I332E | S239D/D265L/N297D/I332E |
| R255Y/I332E | S239D/D265T/N297D/I332E |
| S239D/I332D | S239D/D265V/N297D/I332E |
| S239D/I332E | S239D/D265Y/N297D/I332E |
| S239D/I332N | S239D/I322E/A330Y/A327A |
| S239D/I332Q | S239D/I332E/H268E/A327A |
| S239E/D265G | S239D/I332E/H268E/A330Y |
| S239E/D265N | S239D/N297D/I332E/A330Y |
| S239E/D265Q | S239D/N297D/I332E/K326E |
| S239E/I332D | S239D/N297D/I332E/L235D |
| S239E/I332E | S239D/V264I/A330L/I332E |
| S239E/I332N | S239D/V264I/S298A/I332E |
| S239E/I332Q | S239E/V264I/A330Y/I332E |
| S239N/I332D | F241E/F243Q/V262T/V264E/I332E |
| S239N/I332E | F241E/F243R/V262E/V264R/I332E |
| S239N/I332N | F241E/F243Y/V262T/V264R/I332E |
| S239N/I332Q | F241R/F243Q/V262T/V264R/I332E |
| S239Q/I332D | S239D/I332E/H268E/A330Y/A327A |
| S239Q/I332E | S239E/V264I/S298A/A330Y/I332E |
| S239Q/I332N | F241Y/F243Y/V262T/V264T/N297D/I332E |
| S267E/L328F | G236D/S267E |
| S239D/S267E | |

The Fcγ receptor-binding domain contained in the anti-GPC3 antibody of the present invention can be assayed for its binding activity against the Fcγ receptor appropriately using pH conditions selected from acidic to neutral regions of pH. The acidic to neutral regions of pH as the conditions under which the Fcγ receptor-binding domain contained in the antigen-binding molecule of the present invention is assayed for its binding activity against the Fcγ receptor usually mean pH 5.8 to pH 8.0. The pH range is preferably indicated by arbitrary pH values from pH 6.0 to pH 7.4 and is preferably selected from pH 6.0, 6.1, 6.2, 6.3, 6.4, 6.5, 6.6, 6.7, 6.8, 6.9, 7.0, 7.1, 7.2, 7.3, and 7.4. Particularly, a pH range of 6.15 to 7.4, which is close to the pH of cancer tissues, is preferred (Vaupel et al., Cancer Res. (1989) 49, 6449-6665). The binding affinity of the Fc region for the human Fcγ receptor can be evaluated under assay conditions involving an arbitrary temperature of 10° C. to 50° C. Preferably, a temperature of 15° C. to 40° C. is used for determining the binding affinity of the Fc region for the human Fcγ receptor. More preferably, an arbitrary temperature of 20° C. to 35° C., for example, any one temperature of 20, 21, 22, 23, 24, 25, 26, 27, 28, 29, 30, 31, 32, 33, 34, and 35° C., is also used for determining the binding affinity of the Fc region for the Fcγ receptor. The temperature 25° C. is one non-limiting example in an aspect of the present invention.

The phrase "FcγR-binding modified Fc region having higher binding activity against Fcγ receptors than that of the native Fc region against Fcγ receptors" described herein means that the FcγR-binding modified Fc region has higher binding activity against any of the human Fcγreceptors FcγRI, FcγRIIa, FcγRIIb, FcγRIIIa, and/or FcγRIIIb than that of the native Fc region against the human Fcγ receptor. The phrase means that, for example, on the basis of the analysis method described above, the anti-GPC3 antibody comprising the FcγR-binding modified Fc region exhibits 105% or more, preferably 110% or more, 115% or more, 120% or more, or 125% or more, particularly preferably 130% or more, 135% or more, 140% or more, 145% or more, 150% or more, 155% or more, 160% or more, 165% or more, 170% or more, 175% or more, 180% or more, 185% or more, 190% or more, 195% or more, 2 times or more, 2.5 times or more, 3 times or more, 3.5 times or more, 4 times or more, 4.5 times or more, 5 times or more, 7.5 times or more, 10 times or more, 20 times or more, 30 times or more, 40 times or more, 50 times or more, 60 times or more, 70 times or more, 80 times or more, 90 times or more, 100 times or more binding activity compared with the binding activity of an anti-GPC3 antibody comprising the native Fc region of human IgG serving as a control. The native Fc region used may be the starting Fc region or may be the native Fc region of an antibody of the same subclass as the anti-GPC antibody concerned.

In the present invention, a native human IgG Fc region having a fucose-containing sugar chain as a sugar chain bound to amino acid 297 (EU numbering) is preferably used as the native Fc region of human IgG serving as a control. Whether or not the sugar chain bound to amino acid 297 (EU numbering) is a fucose-containing sugar chain can be confirmed using an approach known in the art. Whether or not the sugar chain bound to the native human IgG Fc region is a fucose-containing sugar chain can be determined by, for example, a method as shown below. The native human IgG to be tested liberates a sugar chain through reaction with N-Glycosidase F (Roche Diagnostics K.K.) (Weitzhandler et al., J. Pharma. Sciences (1994) 83, 12, 1670-1675). Next, proteins are removed through reaction with ethanol, and the resulting reaction solution (Schenk et al., J. Clin. Investigation (2001) 108 (11) 1687-1695) is evaporated to dryness and then fluorescently labeled with 2-aminobenzamide (Bigge et al., Anal. Biochem. (1995) 230 (2) 229-238). After removal of the reagent by solid-phase extraction using a cellulose cartridge, the 2-AB-fluorescently labeled sugar chain is analyzed by normal-phase chromatography. The detected peak in the chromatogram can be observed to thereby determine whether or not the sugar chain bound to the native Fc region of human IgG is a fucose-containing sugar chain.

An anti-GPC3 antibody having an IgG monoclonal antibody Fc region can be appropriately used as the anti-GPC3 antibody comprising the native Fc region of an antibody of the same subclass serving as a control. Structural examples of the Fc region include Fc regions contained in constant regions represented by SEQ ID NOs: 74 (having A added to the N terminus of the sequence of database registration No. AAC82527.1), 75 (having A added to the N terminus of the sequence of database registration No. AAB59393.1), 76 (database registration No. CAA27268.1), and 77 (having A added to the N terminus of the sequence of database registration No. AAB59394.1). In the case of using a certain isotype of anti-GPC3 antibody as a test substance, the anti-GPC3 antibody comprising the Fc region to be tested is studied for its effect of binding activity against Fcγ receptors by use of an anti-GPC3 antibody of the certain isotype as a control. The anti-GPC3 antibody comprising the Fc region thus confirmed to have higher binding activity against Fcγ receptors is appropriately selected.

Fc region having higher binding activity against active Fcγ receptor than its binding activity against inhibitory Fcγ receptor As described above, preferred examples of the active Fcγ receptors include FcγRI (CD64) including FcγRIa, FcγRIb, and FcγRIc, FcγRIIa, and FcγRIII (CD16) including isoforms FcγRIIIa (including allotypes V158 and F158) and FcγRIIIb (including allotypes FcγRIIIb-NA1 and FcγRIIIb-NA2). Preferred examples of the inhibitory Fcγ receptors include FcγRIIb (including FcγRIIb-1 and FcγRIIb-2).

In a non-limiting aspect, alternative examples of the anti-GPC3 antibody of the present invention include an anti-GPC3 antibody comprising an Fc region having higher binding activity against active Fcγ receptors than its binding activity against inhibitory Fcγ receptors. In this case, the phrase "having higher binding activity against active Fcγ receptors than its binding activity against inhibitory Fcγ receptors" means that the Fc region has higher binding activity against any of the human Fcγ receptors FcγRIa, FcγRIIa, FcγRIIIa, and/or FcγRIIIb than its binding activity against FcγRIIb. The phrase means that, for example, on the basis of the analysis method described above, the antigen-binding molecule comprising the Fc region exhibits 105% or more, preferably 110% or more, 120% or more, 130% or more, or 140% or more, particularly preferably 150% or more, 160% or more, 170% or more, 180% or more, 190% or more, 200% or more, 250% or more, 300% or more, 350% or more, 400% or more, 450% or more, 500% or more, 750% or more, 10 times or more, 20 times or more, 30 times or more, 40 times or more, 50 times, 60 times, 70 times, 80 times, 90 times, or 100 times or more binding activity against any of the human Fcγ receptors FcγRIa, FcγRIIa, FcγRIIIa, and/or FcγRIIIb compared with its binding activity against FcγRIIb. The IgG antibody comprising such an Fc region is known to have enhancement in the ADCC activity. Thus, the anti-GPC3 antibody comprising the Fc region is useful as the GPC3-targeting drug of the present invention.

In a non-limiting aspect of the present invention, examples of the Fc region having higher binding activity against active Fcγ receptors than its binding activity against inhibitory Fcγ receptors (having selective binding activity against active Fcγ receptors) preferably include Fc regions in which at least one or more amino acids selected from the group consisting of position 221, position 222, position 223, position 224, position 225, position 227, position 228, position 230, position 231, position 232, position 233, position 234, position 235, position 236, position 237, position 238, position 239, position 240, position 241, position 243, position 244, position 245, position 246, position 247, position 249, position 250, position 251, position 254, position 255, position 256, position 258, position 260, position 262, position 263, position 264, position 265, position 266, position 267, position 268, position 269, position 270, position 271, position 272, position 273, position 274, position 275, position 276, position 278, position 279, position 280, position 281, position 282, position 283, position 284, position 285, position 286, position 288, position 290, position 291, position 292, position 293, position 294, position 295, position 296, position 297, position 298, position 299, position 300, position 301, position 302, position 303, position 304, position 305, position 311, position 313, position 315, position 317, position 318, position 320, position 322, position 323, position 324, position 325, position 326, position 327, position 328, position 329, position 330, position 331, position 332, position 333, position 334, position 335, position 336, position 337, position 339, position 376, position 377, position 378, position 379, position 380, position 382, position 385, position 392, position 396, position 421, position 427, position 428, position 429, position 434, position 436 and position 440

(EU Numbering)

are modified to amino acids different from those in the native Fc region.

In a non-limiting aspect of the present invention, further examples of the Fc region having higher binding activity against active Fcγ receptors than its binding activity against inhibitory Fcγ receptors (having selective binding activity against active Fcγ receptors) preferably include Fc regions in which a plurality of amino acids described in Tables 3-1 to 3-3 are modified to amino acids different from those in the native Fc region.

Fc Region Having Modified Sugar Chain

The Fc region contained in the anti-GPC3 antibody provided by the present invention can also include an Fc region modified such that a higher proportion of fucose-deficient sugar chains is bound to the Fc region or a higher proportion of bisecting N-acetylglucosamine is added to the Fc region in the composition of sugar chains bound to the Fc region. The removal of a fucose residue from N-acetylglucosamine at the reducing end of a N-glycoside-linked complex sugar chain bound to an antibody Fc region is known to enhance its affinity for FcγRIIIa (Sato et al., Expert Opin. Biol. Ther. (2006) 6 (11), 1161-1173). An IgG1 antibody comprising such an Fc region is known to have enhancement in the ADCC activity. Thus, the antigen-binding molecule comprising the Fc region is also useful as the antigen-binding molecule contained in the pharmaceutical composition of the present invention. Examples of an antibody that lacks a fucose residue in N-acetylglucosamine at the reducing end of a N-glycoside-linked complex sugar chain bound to the antibody Fc region include the following antibodies: glycosylated antibodies (e.g., International Publication No. WO1999/054342); and antibodies deficient in fucose added to the sugar chain (e.g., International Publication Nos. WO2000/061739, WO2002/031140, and WO2006/067913). Also, WO2006/046751 and WO2009/041062 disclose specific examples of the anti-GPC3 antibody comprising the Fc region modified such that a higher proportion of fucose-deficient sugar chains is bound to the Fc region or a higher proportion of bisecting N-acetylglucosamine is added to the Fc region in the composition of sugar chains bound to the Fc region.

More specifically, in an alternative non-limiting aspect of the antibody that lacks a fucose residue in N-acetylglucosamine at the reducing end of a N-glycoside-linked complex sugar chain bound to the antibody Fc region, the antibody deficient in fucose added to the sugar chain (e.g., International Publication Nos. WO2000/061739, WO2002/031140, and WO2006/067913) may be prepared. For this purpose, host cells less able to add fucose to sugar chains are prepared as a result of altering the activity of forming the sugar chain structures of polypeptides that undergo sugar chain modification. The host cells are allowed to express the desired antibody gene, and the antibody deficient in fucose in its sugar chain can be recovered from the culture solution of the host cells. Non-limiting preferred examples of the activity of forming the sugar chain structures of polypeptides can include the activity of an enzyme or a transporter selected from the group consisting of fucosyltransferase (EC 2.4.1.152), fucose transporter (SLC35C1), GDP-mannose 4,6-dehydratase (GMD) (EC 4.2.1.47), GDP-keto-6-deoxy-mannose 3,5-epimerase/4-reductase (Fx) (EC 1.1.1.271), and GDP-β-L-fucose pyrophosphorylase (GFPP) (EC 2.7.7.30). These enzymes or transporters are not necessarily limited by their structures as long as the enzymes or the transporters can exert their activity. These proteins capable of exerting such activity are referred to as functional proteins herein. In a non-limiting aspect, examples of methods for altering the activity include the deletion of the activity. Host cells that lack the activity can be prepared by an appropriately adopted method known in the art such as a method which involves disrupting the genes of these functional proteins to render the genes unfunctional (e.g., International Publication Nos. WO2000/061739, WO2002/031140, and WO2006/067913). Such host cells that lack the activity may be prepared by, for example, a method which involves disrupting the endogenous genes of these functional proteins in cells such as CHO cells, BHK cells, NS0 cells, SP2/0 cells, YO myeloma cells, P3X63 mouse myeloma cells, PER cells, PER.C6 cells, HEK293 cells, or hybridoma cells to render the genes unfunctional.

Antibodies containing sugar chains having bisecting GlcNAc (e.g., International Publication No. WO2002/079255) are known in the art. In a non-limiting aspect, host cells expressing genes encoding functional proteins having β-1, 4-mannosyl-glycoprotein 4-β-N-acetylglucosaminyltransferase (GnTIII) (EC 2.4.1.144) activity or β-1,4-galactosyltransferase (GalT) (EC 2.4.1.38) activity are prepared in order to prepare such an antibody containing sugar chains having bisecting GlcNAc. In another non-limiting preferred aspect, host cells coexpressing a gene encoding a functional protein having human mannosidase II (ManII) (3.2.1.114) activity, a gene encoding a functional protein having β-1,2-acetylglucosaminyltransferase I (GnTI) (EC 2.4.1.94) activity, a gene encoding a functional protein having β-1,2-acetylglucosaminyltransferase II (GnTII) (EC 2.4.1.143) activity, a gene encoding a functional protein having mannosidase I (ManI) (EC 3.2.1.113) activity, and an α-1,6-fucosyltransferase (EC 2.4.1.68) gene, in addition to the functional proteins described above, are prepared (International Publication Nos. WO2004/065540).

The host cells less able to add fucose to sugar chains and the host cells having the activity of forming sugar chains having bisecting GlcNAc structures as described above can be transformed with antibody gene-containing expression vectors to respectively prepare the antibody that lacks a fucose residue in N-acetylglucosamine at the reducing end of a N-glycoside-linked complex sugar chain bound to the antibody Fc region and the antibody containing sugar chains having bisecting GlcNAc. The methods for producing these antibodies are also applicable to a method for producing the antigen-binding molecule comprising the Fc region modified such that a higher proportion of fucose-deficient sugar chains is bound to the Fc region or a higher proportion of bisecting N-acetylglucosamine is added to the Fc region in the composition of sugar chains bound to the Fc region of the present invention. The composition of sugar chains bound to the Fc region contained in the antigen-binding molecule of the present invention prepared by such a production method can be confirmed by the method described in the paragraph "Fcγ receptor (FcγR)-binding modified Fc region".

Anti-GPC3 Antibody Having Altered Isoelectric Point

In a non-limiting aspect, further examples of the anti-GPC3 antibody that may be used in the present invention include an anti-GPC3 antibody having an amino acid residue modified to alter its isoelectric point (pI). Preferred examples of the "alteration of the electric charge of an amino acid residue" in the anti-GPC3 antibody provided by the present invention are as follows: alteration to increase the pI value can be performed by, for example, at least one substitution selected from the substitution of Q by K at position 43, the substitution of D by N at position 52, and the substitution of Q by R at position 105 based on the Kabat numbering in the anti-GPC3 antibody heavy chain variable region represented by SEQ ID NO: 50, which is consequently modified to, for example, the amino acid sequence represented by SEQ ID NO: 67. Also, this alteration can be performed by, for example, at least one substitution selected from the substitution of E by Q at position 17, the substitution of Q by R at position 27, and the substitution of Q by R at position 105 based on the Kabat numbering in the anti-GPC3 antibody light chain variable region represented by SEQ ID NO: 51 or 66, which is consequently modified to, for example, the amino acid sequence represented by SEQ ID NO: 68. On the other hand, alteration to decrease the pI value can be performed by at least one substitution selected from the substitution of K by T at position 19, the substitution of Q by E at position 43, the substitution of G by E at position 61, the substitution of K by S at position 62, the substitution of K by Q at position 64, and the substitution of G by D at position 65 based on the Kabat numbering in the anti-GPC3 antibody heavy chain variable region represented by SEQ ID NO: 50, which is consequently modified to, for example, the amino acid sequence represented by SEQ ID NO: 69 or 71. Also, this alteration can be performed by, for example, at least one substitution selected from the substitution of R by Q at position 24, the substitution of Q by E at position 27, the substitution of K by T at position 74, the substitution of R by S at position 77, and the substitution of K by E at position 107 based on the Kabat numbering in the anti-GPC3 antibody light chain variable region represented by SEQ ID NO: 51 or 66, which is consequently modified to, for example, the amino acid sequence represented by SEQ ID NO: 70, 72, or 73. Further examples of the alteration to decrease the pI value include the substitution of at least one amino acid selected from amino acids 268, 274, 355, 356, 358, and 419 based on the EU numbering in the heavy chain constant region represented by SEQ ID NO: 74. Preferred examples of these substitutions can include at least one substitution selected from the substitution of H by Q at position 268, the substitution of K by Q at position 274, the substitution of R by Q at position 355, the substitution of D by E at position 356, the substitution of L by M at position 358, and the substitution of Q by E at position 419 based on the EU numbering in the heavy chain constant region represented by SEQ ID NO: 31. As a result of these substitutions, a chimera having human antibody IgG1 and IgG4 constant regions is constructed. Specifically, these substitutions can yield an antibody having the desired pI without influencing the immunogenicity of the modified antibody.

Modification to Reduce Heterogeneity

An IgG constant region deficient in Gly at position 446 and Lys at position 447 based on the EU numbering in the IgG constant region represented by SEQ ID NO: 74, 75, 76, or 77 may also be used as the constant region contained in the anti-GPC3 antibody of the present invention. Deficiency in both of these amino acids can reduce heterogeneity derived from the end of the heavy chain constant region of the antibody.

Antibody Modification

The posttranslational modification of a polypeptide refers to chemical modification given to the polypeptide translated during polypeptide biosynthesis. Since the primary structure of an antibody is composed of a polypeptide, the anti-GPC3 antibody of the present invention also includes a modified form that has received the posttranslational modification of the polypeptide constituting the primary structure of the anti-GPC3 antibody. The posttranslational modification of a polypeptide can be broadly classified into the addition of a functional group, the addition of a polypeptide or a peptide (ISGylation, SUMOylation, or ubiquitination), the conversion of the chemical properties of an amino acid (silylation, deamination, or deamidation), and structural conversion (disulfidation or protease degradation). In a non-limiting aspect, examples of the posttranslational modification according to the present invention include the addition of a peptide or a functional group to an amino acid residue as a unit constituting the polypeptide. Examples of such modification can specifically include phosphorylation (serine, threonine, tyrosine, aspartic acid, etc.), glucosylation (serine, threonine, aspartic acid, etc.), acylation (lysine), acetylation (lysine), hydroxylation (lysine and proline), prenylation (cysteine), palmitoylation (cysteine), alkylation (lysine and arginine), polyglutamylation (glutamic acid), carboxylation (glutamic acid), polyglycylation (glutamic acid), citrullination (arginine), and succinimide formation (aspartic acid). For example, an anti-GPC3 antibody that has received the modification of N-terminal glutamine to pyroglutamic acid by pyroglutamylation is also included in the anti-GPC3 antibody of the present invention, as a matter of course. Also, for example, a posttranslationally modified anti-GPC3 antibody comprising heavy and light chains or heavy chains linked via a "disulfide bond", which means a covalent bond formed between two sulfur atoms is included in the anti-GPC3 antibody of the present invention. A thiol group contained in an amino acid cysteine can form a disulfide bond or crosslink with a second thiol group. In general IgG molecules, CH1 and CL regions are linked via a disulfide bond, and two polypeptides constituting heavy chains are linked via a disulfide bond between cysteine residues at positions 226 and 229 based on the EU numbering. A posttranslationally modified anti-GPC3 antibody having such a linkage via a disulfide bond is also included in the anti-GPC3 antibody of the present invention.

GPC3-Targeting Drug Therapy

The term "GPC3-targeting drug therapy" refers to the administration of a GPC3-targeting drug to a patient.

The phrase "efficacy of GPC3-targeting drug therapy for cancer" or "GPC3-targeting drug therapy has efficacy for cancer" means that the GPC3-targeting drug therapy produces desired or beneficial effects on a patient diagnosed with cancer. The desired or beneficial effects can include: (1) the inhibition of the further growth or diffusion of cancer cells; (2) the killing of cancer cells; (3) the inhibition of cancer recurrence; (4) the alleviation, reduction, mitigation, or inhibition of cancer-related symptoms (pain, etc.) or reduction in the frequency of the symptoms; and (5) improvement in the survival rate of the patient. The inhibition of cancer recurrence includes the inhibition of the growth of cancer already treated by radiation, chemotherapy, surgical operation, or other techniques, at the primary site of the cancer and its neighboring tissues, and the absence of the growth of cancer at a new distal site. The desired or beneficial effects may be subjectively perceived by the patient or may be objectively found. In the case of, for example, a human patient, the human is able to recognize improvement in energy or vitality or reduction in pain as improvement or a therapy-responsive sign perceived by the patient. Alternatively, a clinician is able to notice decrease in tumor size or the amount of tumor tissues on the basis of findings gained by physical examination, experimental parameters, tumor markers, or X-ray photography. Some experimental signs that can be observed by the clinician in response to treatment include normalized test results of, for example, leukocyte counts, erythrocyte counts, platelet counts, erythrocyte sedimentation rates, and levels of various enzymes. The clinician is further able to observe decrease in detectable tumor marker level. Alternatively, other tests, such as sonography, nuclear magnetic resonance test, and positron emission test, may be used for evaluating objective improvement.

Any cancer having high expression of targeted GPC3 corresponds to the cancer to be treated by the GPC3-targeting drug therapy of the present invention. One example of such cancer include cancer selected from breast cancer, uterine cervix cancer, colon cancer, uterine body cancer, head and neck cancer, liver cancer, lung cancer, malignant carcinoid, malignant glioma, malignant lymphoma, malignant melanoma, ovary cancer, pancreatic cancer, prostatic cancer, renal cancer, skin cancer, gastric cancer, testicle cancer, thyroid cancer, urothelial cancer, and the like.

Method for Determining Efficacy of GPC3-Targeting Drug Therapy or Method for Determining Continuation of GPC3-Targeting Drug Therapy In a non-limiting aspect, the present invention provides a method comprising monitoring a concentration of free GPC3 in a biological sample isolated from a patient before the start of GPC3-targeting drug therapy and/or a patient treated with GPC3-targeting drug therapy, wherein when the concentration of free GPC3 is a predetermined value, the efficacy of the GPC3-targeting drug therapy is determined or the continuation of the therapy is determined. The "patient before the start of GPC3-targeting drug therapy" refers to a patient diagnosed with cancer, having no history of administration of the GPC3-targeting drug. The patient may be a patient for which the efficacy of the GPC3-targeting drug therapy has been determined from the expression level of GPC3 in the tissues. Further, the "patient treated with GPC3-targeting drug therapy" refers to a patient having a history of administration of the GPC3-targeting drug. The administration route of the GPC3-targeting drug can be appropriately selected from administration routes suitable for the properties, etc., of the GPC3-targeting drug to be administered. Examples of the administration route include parenteral administration. Further examples of the parenteral administration include injection, transnasal administration, transpulmonary administration, and percutaneous administration. Further examples of the injection include systemic or local administration based on intravenous injection, intramuscular injection, intraperitoneal injection, and subcutaneous injection.

Known results gained by conventional techniques before the completion of the present invention show that free GPC3 secreted into plasma by processing at a particular site in the polypeptide sequence of GPC3 by an enzyme such as convertase, phospholipase D, or Notum is detected in plasma isolated from liver cancer patients, whereas free GPC3 is not detected in plasma isolated from healthy individuals (Patent Literature 7, etc.). It has been expected from such results that the concentration of free GPC3 detected in serum or plasma is decreased over time with the continuation of the treatment, if the GPC3-targeting drug therapy has efficacy. As a result of conducting diligent studies under such circumstances, surprisingly, the present inventors have found that the concentration of free GPC3 is stabilized or increased, rather than decreased, in serum or plasma isolated from a patient with stable disease that may respond to the GPC3-targeting drug therapy. The present inventors have also found that when the concentration of free GPC3 detected in serum or plasma before administration of GPC3-targeting drug therapy is equal to or higher than the predetermined concentration, the efficacy of the GPC3-targeting drug therapy is determined.

In a non-limiting aspect, the method of the present invention comprises monitoring a concentration of free GPC3 in a biological sample isolated from the patient, wherein when the concentration is a predetermined value, the efficacy of the GPC3-targeting drug therapy for cancer in the patient is predicted, expected, or determined or the continuation of the therapy is determined. The predetermined value may be determined from particular values such as 0.1 ng/mL, 0.2 ng/mL, 0.3 ng/mL, 0.4 ng/mL, 0.5 ng/mL, 0.6 ng/mL, 0.7 ng/mL, 0.8 ng/mL, 0.9 ng/mL, 1.0 ng/mL, 2.0 ng/mL, 3.0 ng/mL, 4.0 ng/mL, 5.0 ng/mL, 6.0 ng/mL, 7.0 ng/mL, 8.0 ng/mL, 9.0 ng/mL, 10.0 ng/mL, 15.0 ng/mL, 20.0 ng/mL, 25.0 ng/mL, 30.0 ng/mL, 35.0 ng/mL, 40.0 ng/mL, 45.0 ng/mL, 50.0 ng/mL, 55.0 ng/mL, 60.0 ng/mL, 65.0 ng/mL, 70.0 ng/mL, 75.0 ng/mL, 80.0 ng/mL, 85.0 ng/mL, 90.0 ng/mL, 100.0 ng/mL or may be determined as a numerical range containing particular values arbitrarily selected as the upper and lower limits from the above group of particular values. As an example, such a numerical range can be appropriately selected from numerical ranges of 0.1 ng/mL to 100 ng/mL. Examples of the numeric range include 0.1 to 100 ng/mL, 0.5 to 80 ng/mL, 1.0 to 60 ng/mL, 2.0 to 55 ng/mL, 3.0 to 50 ng/mL, 4.0 to 45 ng/mL, 5.0 to 40 ng/mL, 6.0 to 35 ng/mL, 7.0 to 30 ng/mL, 8.0 to 25 ng/mL, 9.0 to 20 ng/mL, and 10 to 20 ng/mL. The numerical range is, for example, preferably 0.1 to 0.35 ng/mL, more preferably 0.15 to 0.3 ng/mL, though the numerical range of the present invention is not limited to these ranges. The predetermined value of the concentration of free GPC3 can slightly vary depending on many factors, for example, the assay method used, the type of a sample for free GPC3 assay, storage conditions (e.g., temperature and duration) of the sample, and the ethnic identity of the patient. In the method for predicting, expecting, or determining the efficacy or determining the continuation of the therapy, a concentration in a blood, plasma, or serum sample isolated from the patient is measured as the concentration of free GPC3.

The concentration of free GPC3 can be measured in a sample isolated before and/or after the start of the GPC3-targeting drug therapy and may be measured in a plurality of samples collected at predetermined time intervals. When the concentration of free GPC3 in any one of the plurality of samples collected at predetermined time intervals is the predetermined concentration, the efficacy of the GPC3-targeting drug therapy for cancer in the patient is predicted, expected, or determined or the continuation of the therapy is determined. The predetermined time intervals are appropriately set. In a non-limiting aspect of the intervals, the samples can be collected at intervals of 1 day, 2 days, 3 days, 4 days, 5 days, 6 days, 7 days (i.e., 1 week), 8 days, 9 days, 10 days, 11 days, 12 days, 13 days, 14 days (i.e., 2 weeks), 15 days, 16 days, 17 days, 18 days, 19 days, 20 days, 21 days (i.e., 3 weeks), 22 days, 23 days, 24 days, 25 days, 26 days, 27 days, 28 days (i.e., 4 weeks), 29 days, 30 days, 1 month, 5 weeks, 6 weeks, 7 weeks, 8 weeks, 9 weeks, 10 weeks, 2 months, 3 months, 4 months, 5 months, or 6 months after the initial administration of the GPC3-targeting drug, or at arbitrary points in time between the start and completion of the therapy, for example, after 1, 2, 3, 4 or more treatment cycles. The dosing intervals, i.e., the treatment cycles, can be appropriately set. One non-limiting example thereof includes 1 day, 2 days, 3 days, 4 days, 5 days, 6 days, 7 days (i.e., 1 week), 8 days, 9 days, 10 days, 11 days, 12 days, 13 days, 14 days (i.e., 2 weeks), 15 days, 16 days, 17 days, 18 days, 19 days, 20 days, 21 days (i.e., 3 weeks), 22 days, 23 days, 24 days, 25 days, 26 days, 27 days, 28 days (i.e., 4 weeks), 29 days, 30 days, 1 month, 5 weeks, 6 weeks, 7 weeks, 8 weeks, 9 weeks, 10 weeks, 2 months, 3 months, 4 months, 5 months, or 6 months.

In a non-limiting aspect, the method of the present invention comprises monitoring a concentration of free GPC3 in blood, plasma, or serum isolated 30 days or 1 month after the start of GPC3-targeting drug therapy from the patient treated with the therapy, wherein when the concentration of free GPC3 ranges from 0.1 ng/mL to 100 ng/mL, the efficacy of the GPC3-targeting drug therapy is determined. In another non-limiting aspect, the method of the present invention comprises monitoring a concentration of free GPC3 in blood, plasma, or serum isolated 2 months, 3 months, 4 months, 5 months, or 6 months after the start of GPC3-targeting drug therapy from the patient treated with the therapy, wherein when the concentration of free GPC3 ranges from 0.1 ng/mL to 100 ng/mL, the efficacy of the GPC3-targeting drug therapy is determined.

In a non-limiting aspect, the method of the present invention comprises monitoring a concentration of free GPC3 in blood, plasma, or serum isolated 30 days or 1 month after the start of GPC3-targeting drug therapy from the patient treated with the therapy, wherein when the concentration of free GPC3 ranges from 0.1 ng/mL to 100 ng/mL, the continuation of the GPC3-targeting drug therapy is determined. In another non-limiting aspect, the method of the present invention comprises monitoring a concentration of free GPC3 in blood, plasma, or serum isolated 2 months, 3 months, 4 months, 5 months, or 6 months after the start of GPC3-targeting drug therapy from the patient treated with the therapy, wherein when the concentration of free GPC3 ranges from 0.1 ng/mL to 100 ng/mL, the continuation of the GPC3-targeting drug therapy is determined.

In another non-limiting aspect of the present invention, the concentration of free GPC3 can be compared with a concentration of free GPC3 ("baseline concentration") measured in a blood, plasma, or serum sample isolated before the start of the GPC3-targeting drug therapy from the patient. In this aspect, the "predetermined value" of the concentration of free GPC3 means that the concentration of free GPC3 in the biological sample isolated from the patient treated with the GPC3-targeting drug therapy is equal to or higher than the baseline concentration. Specifically, when the concentration of free GPC3 after the start of the GPC3-targeting drug therapy is equal to or larger than that before the start of the therapy in one patient, the efficacy of the GPC3-targeting drug therapy for cancer in the patient is predicted, expected, or determined or the continuation of the therapy is determined. The rate at which the concentration of free GPC3 after the start of the GPC3-targeting drug therapy is equal to or larger than that before the start of the therapy can be appropriately selected by those skilled in the art and is not limited to a particular value. Such a rate can be appropriately selected from a numerical range of 1 time to $10^6$ times. When the rate is, for example, 1 time or more, 1.05 times or more, 1.1 times or more, 1.2 times or more, 1.3 times or more, 1.4 times or more, 1.5 times or more, 1.6 times or more, 1.7 times or more, 1.8 times or more, 1.9 times or more, 2 times or more, 2.1 times or more, 2.2 times or more, 2.3 times or more, 2.4 times or more, 2.5 times or more, 2.6 times or more, 2.7 times or more, 2.8 times or more, 2.9 times or more, 3 times or more, 3.1 times or more, 3.2 times or more, 3.3 times or more, 3.4 times or more, 3.5 times or more, 3.6 times or more, 3.7 times or more, 3.8 times or more, 3.9 times or more, 4 times or more, 4.1 times or more, 4.2 times or more, 4.3 times or more, 4.4 times or more, 4.5 times or more, 4.6 times or more, 4.7 times or more, 4.8 times or more, 4.9 times or more, 5 times or more, 5.1 times or more, 5.2 times or more, 5.3 times or more, 5.4 times or more, 5.5 times or more, 5.6 times or more, 5.7 times or more, 5.8 times or more, 5.9 times or more, 6 times or more, 6.1 times or more, 6.2 times or more, 6.3 times or more, 6.4 times or more, 6.5 times or more, 6.6 times or more, 6.7 times or more, 6.8 times or more, 6.9 times or more, 7 times or more, 7.1 times or more, 7.2 times or more, 7.3 times or more, 7.4 times or more, 7.5 times or more, 7.6 times or more, 7.7 times or more, 7.8 times or more, 7.9 times or more, 8 times or more, 8.1 times or more, 8.2 times or more, 8.3 times or more, 8.4 times or more, 8.5 times or more, 8.6 times or more, 8.7 times or more, 8.8 times or more, 8.9 times or more, 9 times or more, 9.1 times or more, 9.2 times or more, 9.3 times or more, 9.4 times or more, 9.5 times or more, 9.6 times or more, 9.7 times or more, 9.8 times or more, 9.9 times or more, 10 times or more, 11 times or more, 12 times or more, 13 times or more, 14 times or more, 15 times or more, 16 times or more, 17 times or more, 18 times or more, 19 times or more, 20 times or more, 21 times or more, 22 times or more, 23 times or more, 24 times or more, 25 times or more, 26 times or more, 27 times or more, 28 times or more, 29 times or more, 30 times or more, 31 times or more, 32 times or more, 33 times or more, 34 times or more, 35 times or more, 36 times or more, 37 times or more, 38 times or more, 39 times or more, 40 times or more, 41 times or more, 42 times or more, 43 times or more, 44 times or more, 45 times or more, 46 times or more, 47 times or more, 48 times or more, 49 times or more, 50 times or more, 55 times or more, 60 times or more, 65 times or more, 70 times or more, 75 times or more, 80 times or more, 85 times or more, 90 times or more, 95 times or more, 100 times or more, 105 times or more, 110 times or more, 120 times or more, 130 times or more, 140 times or more, 150 times or more, 160 times or more, 170 times or more, 180 times or more, 190 times or more, 200 times or more, 220 times or more, 240 times or more, 260 times or more, 280 times or more, 300 times or more, 320 times or more, 340 times or more, 360 times or more, 380 times or more, 400 times or more, 420 times or more, 440 times or more, 460 times or more, 480 times or more, 500 times or more, 550 times or more, 600 times or more, 650 times or more, 700 times or more, 750 times or more, 800 times or more, 850 times or more, 900 times or more, 950 times or more, 1000 times or more, 2000 times or more, 3000 times or more, 4000 times or more, 5000 times or more, 6000 times or more, 7000 times or more, 8000 times or more, 9000 times or more, $10^4$ times or more, $2\times10^4$ times or more, $4\times10^4$ times or more, $6\times10^4$ times or more, $8\times10^4$ times or more, $10^5$ times or more, $2\times10^5$ times or more, $4\times10^5$ times or more, $6\times10^5$ times or more, $8\times10^5$ times or more, or $10^6$ times or more, the efficacy of the GPC3-targeting drug therapy for cancer in the patient is predicted, expected, or determined or the continuation of the therapy is determined.

In a non-limiting aspect, the method of the present invention comprises monitoring a concentration of free GPC3 in blood, plasma, or serum isolated 30 days or 1 month after the start of GPC3-targeting drug therapy from the patient treated with the therapy, wherein when the concentration of free GPC3 is equal to or larger than the baseline concentration, the efficacy of the GPC3-targeting drug therapy is determined. In another non-limiting aspect, the method of the present invention comprises monitoring a concentration of free GPC3 in blood, plasma, or serum isolated 2 months, 3 months, 4 months, 5 months, or 6 months after the start of GPC3-targeting drug therapy from the patient treated with the therapy, wherein when the concentration of free GPC3 is 1 time or more to $10^6$ times or more the baseline concentration, the efficacy of the GPC3-targeting drug therapy is determined.

As described above, when the concentration of free GPC3 is equal to or larger than the baseline concentration, the efficacy of the GPC3-targeting drug therapy is determined. In this procedure, the expression level of GPC3 in a tissue, particularly, a cancer tissue (including a liver cancer tissue), isolated from the patient may be taken into consideration. Specifically, when the concentration of free GPC3 in the patient is equal to or larger than the baseline concentration and the expression level of GPC3 in a tissue, particularly, a cancer tissue (including a liver cancer tissue), isolated from the patient is equal to or larger than a particular evaluation score, the efficacy of the GPC3-targeting drug therapy is determined. In another non-limiting aspect, the method of the present invention comprises monitoring a concentration of free GPC3 in blood, plasma, or serum isolated 2 months, 3 months, 4 months, 5 months, or 6 months after the start of GPC3-targeting drug therapy from the patient treated with the therapy, wherein when the concentration of free GPC3 is 1 time or more to $10^6$ times or more the baseline concentration and the expression level of GPC3 in a tissue, particularly, a cancer tissue (including a liver cancer tissue), isolated from the patient is equal to or larger than a predetermined immunohistochemical staining score, the efficacy of the GPC3-targeting drug therapy is determined.

In a non-limiting aspect, examples of the case where the expression level of GPC3 in a tissue, particularly, a cancer tissue (including a liver cancer tissue), isolated from the patient is equal to or larger than a predetermined immunohistochemical staining score can include high expression and low or moderate expression (IHC total score: 7 or higher and lower than 7, respectively) in a composite score calculated as a result of staining according to the staining method 1. In a non-limiting aspect, alternative examples of the case where the expression level of GPC3 is equal to or larger than a predetermined immunohistochemical staining score can include GPC3-IHC scores of 1+, 2+, and 3+ calculated as a result of staining according to the staining method 2.

In a non-limiting aspect, the method of the present invention comprises monitoring a concentration of free GPC3 in blood, plasma, or serum isolated 30 days or 1 month after the start of GPC3-targeting drug therapy from the patient treated with the therapy, wherein when the concentration of free GPC3 is equal to or larger than the baseline concentration, the continuation of the GPC3-targeting drug therapy is determined. In another non-limiting aspect, the method of the present invention comprises monitoring a concentration of free GPC3 in blood, plasma, or serum isolated 2 months, 3 months, 4 months, 5 months, or 6 months after the start of GPC3-targeting drug therapy from the patient treated with the therapy, wherein when the concentration of free GPC3 is 1 time or more to $10^6$ times or more the baseline concentration, the continuation of the GPC3-targeting drug therapy is determined.

As described above, when the concentration of free GPC3 is equal to or larger than the baseline concentration, the continuation of the GPC3-targeting drug therapy is determined. In this procedure, the expression level of GPC3 in a tissue, particularly, a cancer tissue (including a liver cancer tissue), isolated from the patient may be taken into consideration. Specifically, when the concentration of free GPC3 in the patient is equal to or larger than the baseline concentration and the expression level of GPC3 in a tissue, particularly, a cancer tissue (including a liver cancer tissue), isolated from the patient is equal to or larger than a particular evaluation score, the continuation of the GPC3-targeting drug therapy is determined. In another non-limiting aspect, the method of the present invention comprises monitoring a concentration of free GPC3 in blood, plasma, or serum isolated 2 months, 3 months, 4 months, 5 months, or 6 months after the start of GPC3-targeting drug therapy from the patient treated with the therapy, wherein when the concentration of free GPC3 is 1 time or more to $10^6$ times or more the baseline concentration and the expression level of GPC3 in a tissue, particularly, a cancer tissue (including a liver cancer tissue), isolated from the patient is equal to or larger than a predetermined immunohistochemical staining score, the continuation of the GPC3-targeting drug therapy is determined.

In a non-limiting aspect, examples of the case where the expression level of GPC3 in a tissue, particularly, a cancer tissue (including a liver cancer tissue), isolated from the patient is equal to or larger than a predetermined immunohistochemical staining score can include high expression and low or moderate expression (IHC total score: 7 or higher and lower than 7, respectively) in a composite score calculated as a result of staining according to the staining method 1. In a non-limiting aspect, alternative examples of the case where the expression level of GPC3 is equal to or larger than a predetermined immunohistochemical staining score can include GPC3-IHC scores of 1+, 2+, and 3+ calculated as a result of staining according to the staining method 2.

Drug and Preparation

In the present invention, the drug usually refers to an agent for the treatment or prevention of a disease or for examination or diagnosis. In the present invention, the phrase "GPC3-targeting drug which is to be administered to a cancer patient having a predetermined value of a concentration of free GPC3 in a biological sample isolated from the cancer patient before the start of GPC3-targeting drug therapy" may be translated into a "method for treating cancer, comprising administering a GPC3-targeting drug to a cancer patient having a predetermined value of a concentration of free GPC3 in a biological sample isolated from the cancer patient before the start of GPC3-targeting drug therapy" or may be translated into "use of a GPC3-targeting drug which is to be administered to a cancer patient having a predetermined value of a concentration of free GPC3 in a biological sample isolated from the cancer patient before the start of GPC3-targeting drug therapy, for production of an agent for the treatment of cancer". In the present invention, the phrase "GPC3-targeting drug which is to be further administered to a cancer patient having a predetermined value of a concentration of free GPC3 in a biological sample isolated from the cancer patient after the start of GPC3-targeting drug therapy" may be translated into a "method for treating cancer, comprising further administering a GPC3-targeting drug to a cancer patient having a predetermined value of a concentration of free GPC3 in a biological sample isolated from the cancer patient after the start of GPC3-targeting drug therapy" or may be translated into "use of a GPC3-targeting drug which is to be further administered to a cancer patient having a predetermined value of a concentration of free GPC3 in a biological sample isolated from the cancer patient after the start of GPC3-targeting drug therapy, for production of an agent for the treatment of cancer". The phrase "having a predetermined value of a concentration of free GPC3 in a biological sample isolated from the cancer patient after the start of GPC3-targeting drug therapy" may be translated into the phrase "the concentration of free GPC3 in the biological sample isolated from the cancer patient after the start of GPC3-targeting drug therapy has been increased as a result of receiving the GPC3-targeting drug therapy".

The drug of the present invention can be formulated using a method generally known to those skilled in the art. For example, the drug of the present invention can be parenterally used in the form of an injection in a sterile solution or suspension with water or any other pharmaceutically acceptable solution. For example, the active ingredient can be appropriately combined with pharmacologically acceptable carriers or media, specifically, sterile water or saline, a plant oil, an emulsifier, a suspending agent, a surfactant, a stabilizer, a flavor, an excipient, a vehicle, an antiseptic, a binder, and the like and mixed therewith in a unit dosage form required for generally accepted pharmaceutical practice to produce preparations. The amount of the active ingredient in these preparations is set to give an appropriate volume within a prescribed range.

Sterile compositions for injection can be formulated according to usual pharmaceutical practice using a vehicle such as injectable distilled water. Examples of injectable aqueous solutions include saline and isotonic solutions containing glucose or other adjuvants (e.g., D-sorbitol, D-mannose, D-mannitol, and sodium chloride). An appropriate solubilizer, for example, an alcohol (ethanol, etc.), a polyalcohol (propylene glycol, polyethylene glycol, etc.), or a nonionic surfactant (Polysorbate 80™, HCO-50, etc.) may be used in combination therewith.

Examples of oil solutions include sesame oil and soybean oil. Benzyl benzoate and/or benzyl alcohol may be used as a solubilizer in combination therewith. These injectable solutions may be mixed with a buffer (e.g., a phosphate buffer solution and a sodium acetate buffer solution), a soothing agent (e.g., procaine hydrochloride), a stabilizer (e.g., benzyl alcohol and phenol), and an antioxidant. The prepared injections are usually charged into appropriate ampules.

The drug of the present invention is preferably administered by parenteral administration. For example, the drug is administered in a dosage form of an injection, a transnasal agent, a transpulmonary agent, or a percutaneous agent. The drug can be administered systemically or locally by, for example, intravenous injection, intramuscular injection, intraperitoneal injection, or subcutaneous injection.

The administration method can be appropriately selected according to the age and symptoms of the patient. The single dose of a pharmaceutical preparation containing the drug can be set within the range of, for example, 0.0001 mg to 1000 mg per kg body weight. Alternatively, the dose can be set to, for example, 0.001 to 100000 mg per patient, though the dose of the present invention is not necessarily limited to these numeric values. The dose and the administration method vary depending on the body weight, age, symptoms, etc. of the patient. Those skilled in the art can set an appropriate dose and administration method in consideration of these conditions. As a preferred example of the dose and the administration method of the present invention, the drug of the present invention can be administered to achieve a blood trough level equal to or higher than a predetermined level in the patient. Preferred examples of the blood trough level can include 150 µg/mL or higher, 160 µg/mL or higher, 170 µg/mL or higher, 180 µg/mL or higher, 190 µg/mL or higher, 200 µg/mL or higher, 210 µg/mL or higher, 220 µg/mL or higher, 230 µg/mL or higher, 240 µg/mL or higher, 250 µg/mL or higher, 260 µg/mL or higher, 270 µg/mL or higher, 280 µg/mL or higher, 290 µg/mL or higher, 300 µg/mL or higher, and 400 µg/mL or higher. More preferred examples thereof can include 200 µg/mL or higher.

The preparation of the present invention comprises an instruction stating that the preparation is to be further administered to a cancer patient having a predetermined value of a concentration of free GPC3 in a biological sample isolated from the cancer patient after the start of GPC3-targeting drug therapy. In another non-limiting aspect, the preparation of the present invention comprises an instruction stating that the preparation is to be further administered to a cancer patient in which the concentration of free GPC3 in the biological sample isolated from the cancer patient after the start of GPC3-targeting drug therapy has been increased as a result of receiving the GPC3-targeting drug therapy.

In a non-limiting aspect, the present invention provides the preparation comprising an instruction stating that the patient is selected on the basis of a method comprising monitoring a concentration of free GPC3 in a biological sample isolated from the patient treated with the GPC3-targeting drug therapy, wherein when the concentration of free GPC3 is a predetermined value, the efficacy of the GPC3-targeting drug therapy is determined or the continuation of the therapy is determined.

In a non-limiting aspect, the present invention provides the preparation comprising an instruction stating that the patient is selected on the basis of a method comprising monitoring a concentration of free GPC3 in a biological sample isolated from the patient, wherein when the concentration is a predetermined value, the efficacy of the GPC3-targeting drug therapy for cancer in the patient is predicted, expected, or determined or the continuation of the therapy is determined. The predetermined value may be determined from particular values such as 0.1 ng/mL, 0.2 ng/mL, 0.3 ng/mL, 0.4 ng/mL, 0.5 ng/mL, 0.6 ng/mL, 0.7 ng/mL, 0.8 ng/mL, 0.9 ng/mL, 1.0 ng/mL, 2.0 ng/mL, 3.0 ng/mL, 4.0 ng/mL, 5.0 ng/mL, 6.0 ng/mL, 7.0 ng/mL, 8.0 ng/mL, 9.0 ng/mL, 10.0 ng/mL, 15.0 ng/mL, 20.0 ng/mL, 25.0 ng/mL, 30.0 ng/mL, 35.0 ng/mL, 40.0 ng/mL, 45.0 ng/mL, 50.0 ng/mL, 55.0 ng/mL, 60.0 ng/mL, 65.0 ng/mL, 70.0 ng/mL, 75.0 ng/mL, 80.0 ng/mL, 85.0 ng/mL, 90.0 ng/mL, 100.0 ng/mL or may be determined as a numerical range containing particular values arbitrarily selected as the upper and lower limits from the above group of particular values. As an example, such a numerical range can be appropriately selected from numerical ranges of 0.1 ng/mL to 100 ng/mL. Examples of the numeric range include 0.1 to 100 ng/mL, 0.5 to 80 ng/mL, 1.0 to 60 ng/mL, 2.0 to 55 ng/mL, 3.0 to 50 ng/mL, 4.0 to 45 ng/mL, 5.0 to 40 ng/mL, 6.0 to 35 ng/mL, 7.0 to 30 ng/mL, 8.0 to 25 ng/mL, 9.0 to 20 ng/mL, and 10 to 20 ng/mL. The numerical range is, for example, preferably 0.1 to 0.35 ng/mL, more preferably 0.15 to 0.3 ng/mL, though the numerical range of the present invention is not limited to these ranges. The predetermined value of the concentration of free GPC3 can slightly vary depending on many factors, for example, the assay method used, the type of a sample for free GPC3 assay, storage conditions (e.g., temperature and duration) of the sample, and the ethnic identity of the patient. In the method for predicting, expecting, or determining the efficacy or determining the continuation of the therapy, a concentration in a blood, plasma, or serum sample isolated from the patient is measured as the concentration of free GPC3.

The concentration of free GPC3 can be measured in a sample isolated before and/or after the start of the GPC3-targeting drug therapy and may be measured in a plurality of samples collected at predetermined time intervals. When the concentration of free GPC3 in any one of the plurality of samples collected at predetermined time intervals is the predetermined concentration, the efficacy of the GPC3-targeting drug therapy for cancer in the patient is predicted, expected, or determined or the continuation of the therapy is determined. The predetermined time intervals at which the sample is collected after the start of the GPC3-targeting drug therapy are appropriately set. In a non-limiting aspect of the intervals, the samples can be collected at intervals of 1 day, 2 days, 3 days, 4 days, 5 days, 6 days, 7 days (i.e., 1 week), 8 days, 9 days, 10 days, 11 days, 12 days, 13 days, 14 days (i.e., 2 weeks), 15 days, 16 days, 17 days, 18 days, 19 days, 20 days, 21 days (i.e., 3 weeks), 22 days, 23 days, 24 days, 25 days, 26 days, 27 days, 28 days (i.e., 4 weeks), 29 days, 30 days, 1 month, 5 weeks, 6 weeks, 7 weeks, 8 weeks, 9 weeks, 10 weeks, 2 months, 3 months, 4 months, 5 months, or 6 months after the initial administration of the GPC3-targeting drug, or at arbitrary points in time between the start and completion of the therapy, for example, after 1, 2, 3, 4 or more treatment cycles. The dosing intervals, i.e., the treatment cycles, can be appropriately set. One non-limiting example thereof includes 1 day, 2 days, 3 days, 4 days, 5 days, 6 days, 7 days (i.e., 1 week), 8 days, 9 days, 10 days, 11 days, 12 days, 13 days, 14 days (i.e., 2 weeks), 15 days, 16 days, 17 days, 18 days, 19 days, 20 days, 21 days (i.e., 3 weeks), 22 days, 23 days, 24 days, 25 days, 26 days, 27 days, 28 days (i.e., 4 weeks), 29 days, 30 days, 1 month, 5 weeks, 6 weeks, 7 weeks, 8 weeks, 9 weeks, 10 weeks, 2 months, 3 months, 4 months, 5 months, or 6 months.

In a non-limiting aspect, the instruction states that the patient is selected on the basis of a method comprising monitoring a concentration of free GPC3 in blood, plasma, or serum isolated 30 days or 1 month after the start of GPC3-targeting drug therapy from the patient treated with the therapy, wherein when the concentration of free GPC3 ranges from 0.1 ng/mL to 100 ng/mL, the efficacy of the GPC3-targeting drug therapy is determined. In another non-limiting aspect, the instruction states that the patient is selected on the basis of a method comprising monitoring a concentration of free GPC3 in blood, plasma, or serum isolated 2 months, 3 months, 4 months, 5 months, or 6 months after the start of GPC3-targeting drug therapy from the patient treated with the therapy, wherein when the concentration of free GPC3 ranges from 0.1 ng/mL to 100 ng/mL, the efficacy of the GPC3-targeting drug therapy is determined.

In a non-limiting aspect, the instruction states that the patient is selected on the basis of a method comprising monitoring a concentration of free GPC3 in blood, plasma, or serum isolated 30 days or 1 month after the start of GPC3-targeting drug therapy from the patient treated with the therapy, wherein when the concentration of free GPC3 ranges from 0.1 ng/mL to 100 ng/mL, the continuation of the GPC3-targeting drug therapy is determined. In another non-limiting aspect, the instruction states that the patient is selected on the basis of a method comprising monitoring a concentration of free GPC3 in blood, plasma, or serum isolated 2 months, 3 months, 4 months, 5 months, or 6 months after the start of GPC3-targeting drug therapy from the patient treated with the therapy, wherein when the concentration of free GPC3 ranges from 0.1 ng/mL to 100 ng/mL, the continuation of the GPC3-targeting drug therapy is determined.

In another non-limiting aspect of the present invention, the concentration of free GPC3 can be compared with a concentration of free GPC3 ("baseline concentration") measured in a blood, plasma, or serum sample isolated before the start of the GPC3-targeting drug therapy from the patient. In this aspect, the "predetermined value" of the concentration of free GPC3 means that the concentration of free GPC3 in the biological sample isolated from the patient treated with the GPC3-targeting drug therapy is equal to or higher than the baseline concentration. Specifically, when the concentration of free GPC3 after the start of the GPC3-targeting drug therapy is equal to or larger than that before the start of the therapy in one patient, the efficacy of the GPC3-targeting drug therapy for cancer in the patient is predicted, expected, or determined or the continuation of the therapy is determined. The rate at which the concentration of free GPC3 after the start of the GPC3-targeting drug therapy is equal to or larger than that before the start of the therapy can be appropriately selected by those skilled in the art and is not limited to a particular value. Such a rate can be appropriately selected from a numerical range of 1 time to $10^6$ times. When the rate is, for example, 1 time or more, 1.05 times or more, 1.1 times or more, 1.2 times or more, 1.3 times or more, 1.4 times or more, 1.5 times or more, 1.6 times or more, 1.7 times or more, 1.8 times or more, 1.9 times or more, 2 times or more, 2.1 times or more, 2.2 times or more, 2.3 times or more, 2.4 times or more, 2.5 times or more, 2.6 times or more, 2.7 times or more, 2.8 times or more, 2.9 times or more, 3 times or more, 3.1 times or more, 3.2 times or more, 3.3 times or more, 3.4 times or more, 3.5 times or more, 3.6 times or more, 3.7 times or more, 3.8 times or more, 3.9 times or more, 4 times or more, 4.1 times or more, 4.2 times or more, 4.3 times or more, 4.4 times or more, 4.5 times or more, 4.6 times or more, 4.7 times or more, 4.8 times or more, 4.9 times or more, 5 times or more, 5.1 times or more, 5.2 times or more, 5.3 times or more, 5.4 times or more, 5.5 times or more, 5.6 times or more, 5.7 times or more, 5.8 times or more, 5.9 times or more, 6 times or more, 6.1 times or more, 6.2 times or more, 6.3 times or more, 6.4 times or more, 6.5 times or more, 6.6 times or more, 6.7 times or more, 6.8 times or more, 6.9 times or more, 7 times or more, 7.1 times or more, 7.2 times or more, 7.3 times or more, 7.4 times or more, 7.5 times or more, 7.6 times or more, 7.7 times or more, 7.8 times or more, 7.9 times or more, 8 times or more, 8.1 times or more, 8.2 times or more, 8.3 times or more, 8.4 times or more, 8.5 times or more, 8.6 times or more, 8.7 times or more, 8.8 times or more, 8.9 times or more, 9 times or more, 9.1 times or more, 9.2 times or more, 9.3 times or more, 9.4 times or more, 9.5 times or more, 9.6 times or more, 9.7 times or more, 9.8 times or more, 9.9 times or more, 10 times or more, 11 times or more, 12 times or more, 13 times or more, 14 times or more, 15 times or more, 16 times or more, 17 times or more, 18 times or more, 19 times or more, 20 times or more, 21 times or more, 22 times or more, 23 times or more, 24 times or more, 25 times or more, 26 times or more, 27 times or more, 28 times or more, 29 times or more, 30 times or more, 31 times or more, 32 times or more, 33 times or more, 34 times or more, 35 times or more, 36 times or more, 37 times or more, 38 times or more, 39 times or more, 40 times or more, 41 times or more, 42 times or more, 43 times or more, 44 times or more, 45 times or more, 46 times or more, 47 times or more, 48 times or more, 49 times or more, 50 times or more, 55 times or more, 60 times or more, 65 times or more, 70 times or more, 75 times or more, 80 times or more, 85 times or more, 90 times or more, 95 times or more, 100 times or more, 105 times or more, 110 times or more, 120 times or more, 130 times or more, 140 times or more, 150 times or more, 160 times or more, 170 times or more, 180 times or more, 190 times or more, 200 times or more, 220 times or more, 240 times or more, 260 times or more, 280 times or more, 300 times or more, 320 times or more, 340 times or more, 360 times or more, 380 times or more, 400 times or more, 420 times or more, 440 times or more, 460 times or more, 480 times or more, 500 times or more, 550 times or more, 600 times or more, 650 times or more, 700 times or more, 750 times or more, 800 times or more, 850 times or more, 900 times or more, 950 times or more, 1000 times or more, 2000 times or more, 3000 times or more, 4000 times or more, 5000 times or more, 6000 times or more, 7000 times or more, 8000 times or more, 9000 times or more, $10^4$ times or more, $2\times10^4$ times or more, $4\times10^4$ times or more, $6\times10^4$ times or more, $8\times10^4$ times or more, $10^5$ times or more, $2\times10^5$ times or more, $4\times10^5$ times or more, $6\times10^5$ times or more, $8\times10^5$ times or more, or $10^6$ times or more, the efficacy of the GPC3-targeting drug therapy for cancer in the patient is predicted, expected, or determined or the continuation of the therapy is determined.

In a non-limiting aspect, the instruction states that the patient is selected on the basis of a method comprising monitoring a concentration of free GPC3 in blood, plasma, or serum isolated 30 days or 1 month after the start of GPC3-targeting drug therapy from the patient treated with the therapy, wherein when the concentration of free GPC3 is equal to or larger than the baseline concentration, the efficacy of the GPC3-targeting drug therapy is determined. In another non-limiting aspect, the instruction states that the patient is selected on the basis of a method comprising monitoring a concentration of free GPC3 in blood, plasma, or serum isolated 2 months, 3 months, 4 months, 5 months, or 6 months after the start of GPC3-targeting drug therapy from the patient treated with the therapy, wherein when the concentration of free GPC3 is 1 time or more to $10^6$ times or more the baseline concentration, the efficacy of the GPC3-targeting drug therapy is determined.

As described above, the instruction states that when the concentration of free GPC3 is equal to or larger than the baseline concentration, the efficacy of the GPC3-targeting drug therapy is determined. In this case, the instruction may state that the expression level of GPC3 in a tissue, particularly, a cancer tissue (including a liver cancer tissue), isolated from the patient is also taken into consideration. Specifically, the instruction may state that when the concentration of free GPC3 in the patient is equal to or larger than the baseline concentration and the expression level of GPC3 in a tissue, particularly, a cancer tissue (including a liver cancer tissue), isolated from the patient is equal to or larger than a particular evaluation score, the efficacy of the GPC3-targeting drug therapy is determined. In another non-limiting aspect, the instruction can state that the patient is selected on the basis of a method comprising monitoring a concentration of free GPC3 in blood, plasma, or serum isolated 2 months, 3 months, 4 months, 5 months, or 6 months after the start of GPC3-targeting drug therapy from the patient treated with the therapy, wherein when the concentration of free GPC3 is 1 time or more to $10^6$ times or more the baseline concentration and the expression level of GPC3 in a tissue, particularly, a cancer tissue (including a liver cancer tissue), isolated from the patient is equal to or larger than a predetermined immunohistochemical staining score, the efficacy of the GPC3-targeting drug therapy is determined.

In a non-limiting aspect, examples of the case where the expression level of GPC3 in a tissue, particularly, a cancer tissue (including a liver cancer tissue), isolated from the patient is equal to or larger than a predetermined immunohistochemical staining score can include high expression and low or moderate expression (IHC total score: 7 or higher and lower than 7, respectively) in a composite score calculated as a result of staining according to the staining method 1. In a non-limiting aspect, alternative examples of the case where the expression level of GPC3 is equal to or larger than a predetermined immunohistochemical staining score can include GPC3-IHC scores of 1+, 2+, and 3+ calculated as a result of staining according to the staining method 2.

In a non-limiting aspect, the instruction states that the patient is selected on the basis of a method comprising monitoring a concentration of free GPC3 in blood, plasma, or serum isolated 30 days or 1 month after the start of GPC3-targeting drug therapy from the patient treated with the therapy, wherein when the concentration of free GPC3 is equal to or larger than the baseline concentration, the continuation of the GPC3-targeting drug therapy is determined. In another non-limiting aspect, the instruction states that the patient is selected on the basis of a method comprising monitoring a concentration of free GPC3 in blood, plasma, or serum isolated 2 months, 3 months, 4 months, 5 months, or 6 months after the start of GPC3-targeting drug therapy from the patient treated with the therapy, wherein when the concentration of free GPC3 is 1 time or more to $10^6$ times or more the baseline concentration, the continuation of the GPC3-targeting drug therapy is determined.

As described above, the instruction states that when the concentration of free GPC3 is equal to or larger than the baseline concentration, the continuation of the GPC3-targeting drug therapy is determined. In this case, the instruction may state that the expression level of GPC3 in a tissue, particularly, a cancer tissue (including a liver cancer tissue), isolated from the patient is also taken into consideration. Specifically, the instruction may state that when the concentration of free GPC3 in the patient is equal to or larger than the baseline concentration and the expression level of GPC3 in a tissue, particularly, a cancer tissue (including a liver cancer tissue), isolated from the patient is equal to or larger than a particular evaluation score, the continuation of the GPC3-targeting drug therapy is determined. In another non-limiting aspect, the instruction can state that the patient is selected on the basis of a method comprising monitoring a concentration of free GPC3 in blood, plasma, or serum isolated 2 months, 3 months, 4 months, 5 months, or 6 months after the start of GPC3-targeting drug therapy from the patient treated with the therapy, wherein when the concentration of free GPC3 is 1 time or more to $10^6$ times or more the baseline concentration and the expression level of GPC3 in a tissue, particularly, a cancer tissue (including a liver cancer tissue), isolated from the patient is equal to or larger than a predetermined immunohistochemical staining score, the continuation of the GPC3-targeting drug therapy is determined.

In a non-limiting aspect, examples of the case where the expression level of GPC3 in a tissue, particularly, a cancer tissue (including a liver cancer tissue), isolated from the patient is equal to or larger than a predetermined immunohistochemical staining score can include high expression and low or moderate expression (IHC total score: 7 or higher and lower than 7, respectively) in a composite score calculated as a result of staining according to the staining method 1. In a non-limiting aspect, alternative examples of the case where the expression level of GPC3 is equal to or larger than a predetermined immunohistochemical staining score can include GPC3-IHC scores of 1+, 2+, and 3+ calculated as a result of staining according to the staining method 2.

Hereinafter, the present invention will be described specifically with reference to Examples. However, the present invention is not limited by these Examples.

Example 1

GC33 is a recombinant humanized IgG1 monoclonal antibody capable of binding to human GPC3 with high affinity (WO2006/006693). In order to confirm the dose limiting toxicity (DLT) of GC33 in patients with advanced and/or recurrent hepatocellular cancer (HCC), a phase-I multicenter clinical trial was carried out (GC-001US test). In this test aimed at confirming safety and/or tolerability in the patients with advanced and/or recurrent HCC, the pharmacokinetic profiles of GC33, and its antitumor effects, and searching for biomarkers, GC33 (2.5 mg/kg to 20 mg/kg) was administered by injection through an intravenous drip to each HCC patient once a week.

The HCC patients subjected to the administration had histologically or cytologically confirmed advanced or metastatic HCC unsuitable for surgical operation and/or curative treatment. Eligible patients were at least 18 years old and exhibited Eastern Cooperative Oncology Group Performance Status of 0 or 1 and Child-Pugh class A or B. The patients also had at least one lesion that was evaluable according to the response evaluation criteria in solid tumors (RECIST). The provision of HCC tumor tissues (needle biopsy preparations) for use in GPC3 immunohistochemical staining (GPC3-IHC), appropriate hematopoietic functions (absolute neutrophil count ≥1500/μl, platelet ≥50000/μl), hepatic functions (total bilirubin ≤3 times the normal level, aspartate aminotransferase and alanine aminotransferase ≤5 times the normal level, PT-INR ≤2.0), and renal functions (serum creatinine≤twice the normal level) were evaluated as other criteria. The registered subjects excluded pregnant, nursing, or pregnancy test-positive (women who underwent menstruation within 12 months from the registration date were subjected to the pregnancy test) patients, patients who did not plan to use appropriate fertility control, HIV antibody-positive patients, patients having active infection requiring treatment except for HBV or HCV, patients having other active malignant tumors with a disease-free interval shorter than 5 years, patients having a past history of transplantation, patients confirmed to have brain metastasis with symptoms, patients having central nervous system disorder or other mental disorders that interfered with consent or understanding of the protocol, patients who presented central nervous system symptoms attributed to hepatic encephalopathy, and patients who exhibited known hypersensitivity to other antibody drugs or pharmaceutical agents produced using CHO cells. Alternatively, patients who received treatment including major surgical operation, radiation therapy, and other chemotherapies within 4 weeks before the administration of the GPC3-targeting drug, patients who received treatment with sorafenib within 2 weeks before the administration, or patients who received needle biopsy within 1 week before the administration were excluded from the subjects registered in the GPC3-targeting drug therapy, but were subjected to the GPC3-targeting treatment after a predetermined wash-out period. The protocol was carried out according to the guideline of the Good Clinical Practice (GCP) and approved by each participating ethical committee on clinical trials. All patients signed their names on written informed consent before registration. The patients received the continuous administration of GC33 (each cycle involved four doses of GC33) unless the disease progressed or unacceptable toxicity appeared. Tumor was evaluated on the basis of a baseline and repetitively evaluated every two cycles until the disease progressed. The state of the disease was evaluated by principal investigators.

The expression of GPC3 proteins in HCC tumor tissues was evaluated by GPC3 immunohistochemical staining (GPC3-IHC). The median measurement of GPC3-IHC was carried out by Charles River Laboratory (USA). Unstained slides of HCC tumor tissues prepared from tumor blocks formalin-fixed and paraffin-embedded after excision by needle biopsy in each hospital were subjected to immunohistochemical staining. The histochemical staining approach such as epitope retrieval for the measurement by Charles River Laboratory (USA) was performed according to a method described in WO2009/116659. The antibodies used were a mouse GC33 antibody and a mouse IgG2a antibody as a negative control antibody (WO2006/006693).

As for GPC3-IHC (staining method 1) carried out by Charles River Laboratory, the respective scores of positive cell rate (PR), staining intensity of cytoplasm (SI-cp) or staining intensity of cell membrane (SI-cm), and staining pattern of cell membrane (Sp-cm) were calculated according to the criteria shown in Table 4 and added on the basis of calculation expressions 1 and 2 to evaluate each stained preparation. The evaluation of each stained preparation was finalized at the Peer review meeting involving three pathologists.

TABLE 4

| Criterion | Evaluation | Score |
| --- | --- | --- |
| Positive cell rate (PR) | 0 | 0 |
| | 1% or more and less than 20% | 1 |
| | 20% or more and less than 50% | 2 |
| | 50% or more | 3 |
| Staining intensity (SI) | Slightly positive | 0 |
| Cytoplasm (SI-cp) | Weakly positive | 1 |
| Cell membrane (SI-cm) | Moderately positive and/or weakly positive with strong positivity | 2 |
| | Moderately positive | 3 |
| | Strongly positive | 4 |
| Staining pattern of cell membrane (SP-cm) | Negative | 0 |
| | When only a portion of the cell membranes of cells was stained | 1 |
| | When a portion of the cell membranes of most of these cells was stained and the cell membranes of some of the cells were circumferentially stained | 2 |
| | When the cell membranes of most of these cells were circumferentially stained | 3 |

(Sp-cm scores were calculated by the evaluation of cell staining in the visual field under microscope using an objective lens with a magnification of 4 or 10)

$$IHC\ total = PR + SI\text{-}Cp + SI\text{-}Cm + Sp\text{-}Cm \quad \text{[Expression 3]}$$

Figure 1B:
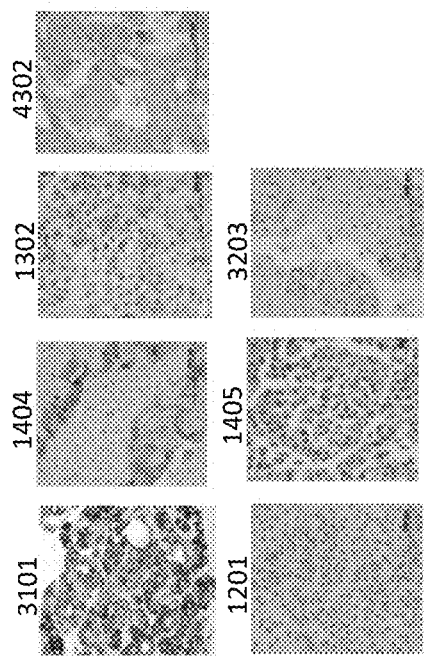
FIG. 1B is a diagram showing the histochemical staining images of tissues evaluated as being negative or having low expression in a staining score of GPC3-IHC (staining method 1). The numeral shown in the upper part of each staining image represents a patient number.

One out of 20 cases that were registered in this test and received the administration failed to produce a preparation, and 3 of the cases did not contain tumor cells sufficient for evaluation. Finally, 16 cases were able to be evaluated. These cases were divided into two groups on the basis of an IHC total score around 7, which was half the maximum value (14) in staining based on epitope retrieval using autoclaving. The evaluation results of each case are shown in Table 5 and FIG. 1.

TABLE 5

| Evaluation by GPC-IHC (IHC total score) | The number of patients (percentage to the total number 20) |
| --- | --- |
| High expression (7 or higher) | 9 (45%) |
| Low or moderate expression (Lower than 7) | 7 (35%) |
| Unevaluable | 4 (20%) |

Example 2

Figure 2:
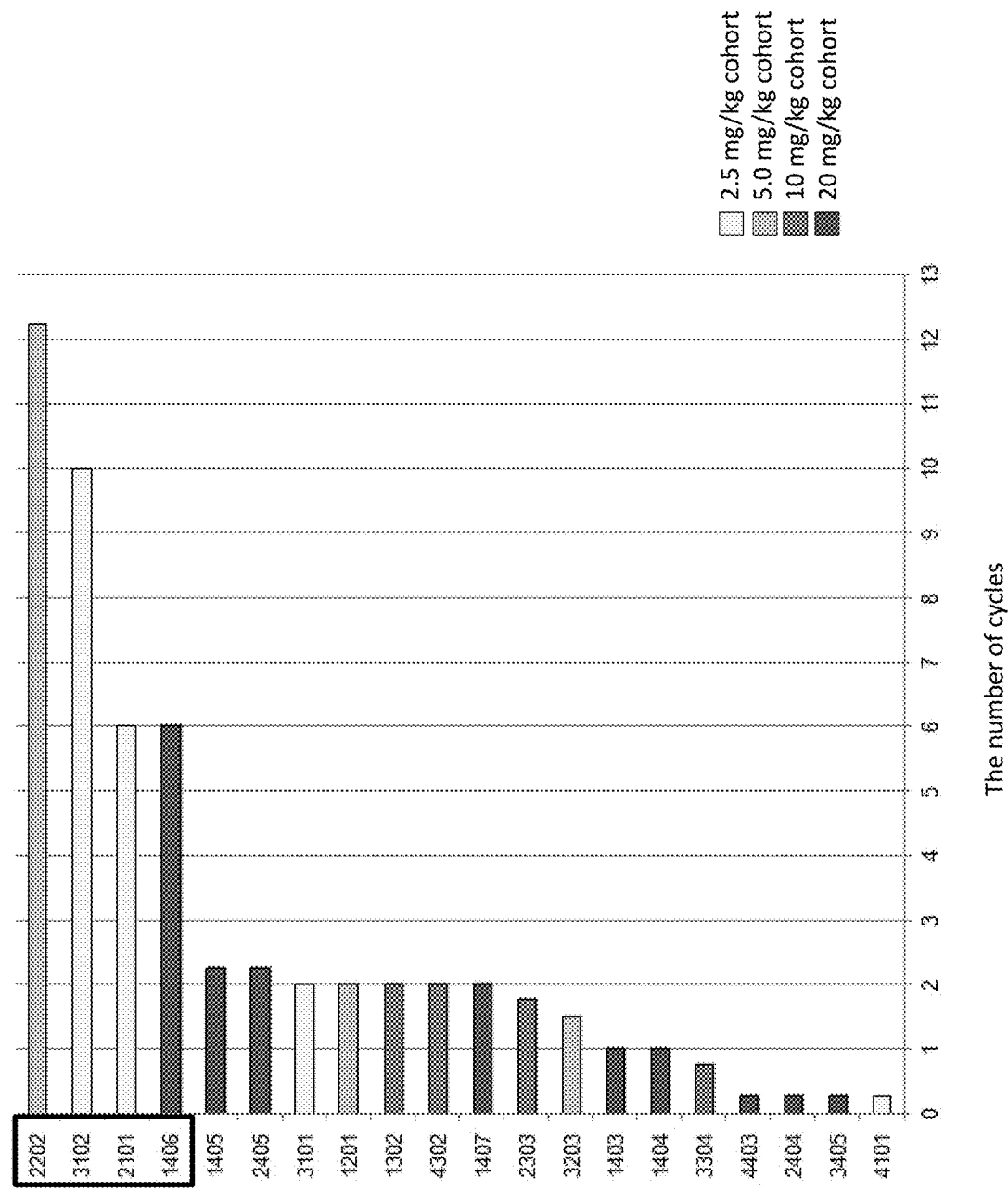
FIG. 2 is a diagram showing the durations of GC33 administration to 20 cases. Each cycle involves four doses of GC33 (administered once a week).

Antitumor effects were evaluated by the administration of GC33 in GPC3-targeting treatment. The durations of GC33 administration to 20 cases as described above are shown in FIG. 2. As a result of evaluating the state of the disease, 5-month or longer stable disease (SD) was confirmed in 4 cases.

The expression of GPC3 in tumor tissues was examined for its relation to the antitumor effects of GC33. As a result of showing the relation of the IHC total scores of 16 cases evaluable by GPC3-IHC to the duration of administration, all cases confirmed to have SD in a 5-month or longer period were included in a high-value group when the 16 cases were divided into two groups (with an IHC total score of 7 or higher and with an IHC total score lower than 7). In addition, the obtained results showed that the percentage of the long-period SD cases in the high-value group was also high (Table 6).

TABLE 6

| IHC total score | High-value group | | Low-value group | |
|---|---|---|---|---|
| 6 or higher | 36% | (4/11) | 0% | (0/5) |
| 7 or higher | 44% | (4/9) | 0% | (0/7) |
| 8 or higher | 50% | (3/6) | 10% | (1/10) |
| 9 or higher | 50% | (2/4) | 17% | (2/12) |
| 10 or higher | 50% | (1/2) | 21% | (3/14) |

Figure 3:
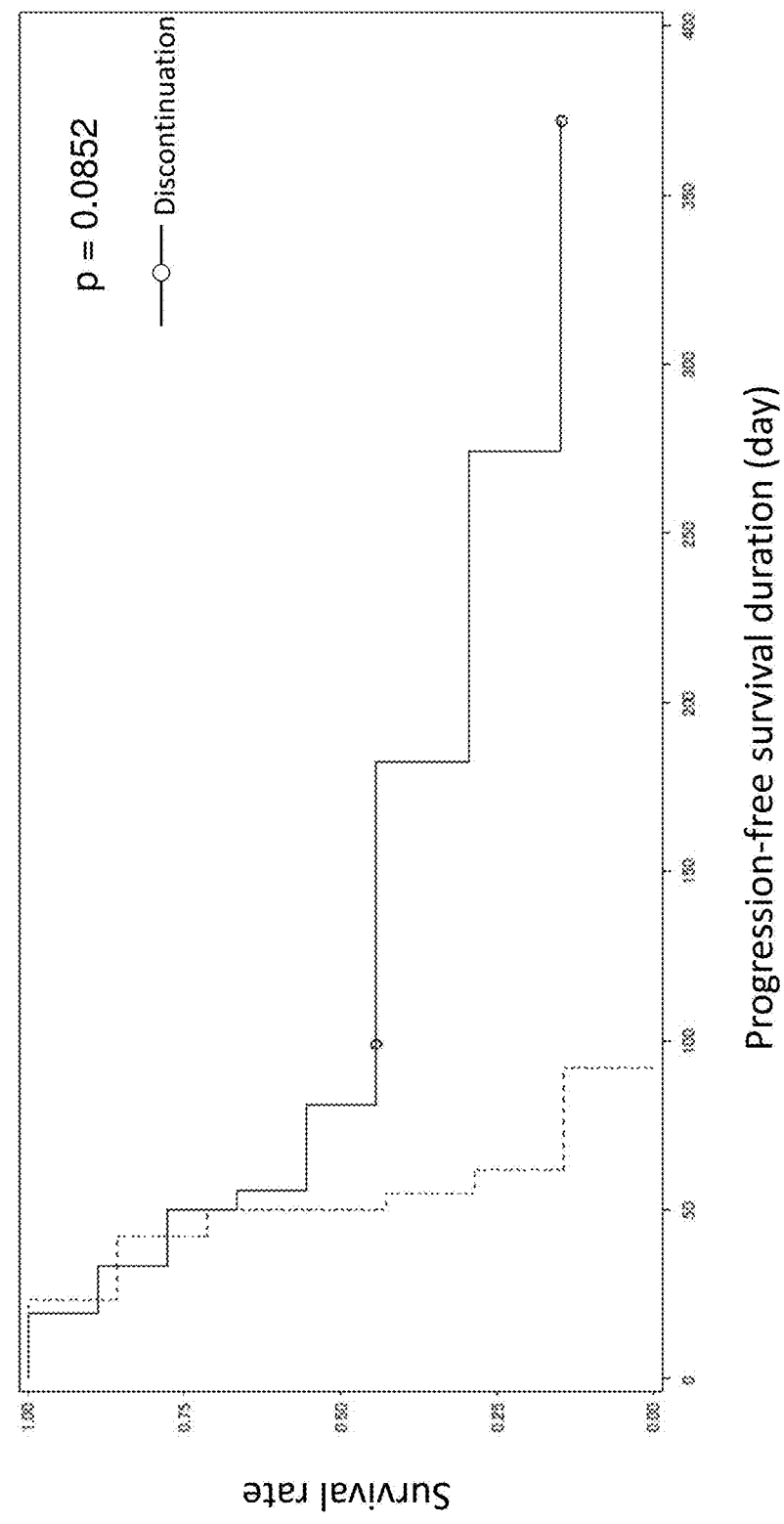
FIG. 3 is a diagram showing a difference in progression-free survival duration among a patient group from which samples divided into two groups (with a total score of 7 or higher and with a total score lower than 7) according to a staining method based on epitope retrieval using autoclaving were isolated. The solid line represents the progression-free survival duration of the group with a total score of 7 or higher (9 cases). The broken line represents the progression-free survival duration of the group with a total score lower than 7 (7 cases). The hazard ratio of the group with a total score of 7 or higher to the group with a total score lower than 7 was 0.376 (95% confidence interval: 0.116-1.227, p=0.0852).

Subsequently, progression-free survival duration or progression-free survival (PFS) was compared between the group with an IHC total score of 7 or higher and the group with an IHC total score lower than 7. The results showed that the group with an IHC total score of 7 or higher had significantly long PFS (FIG. 3).

Some of the tumor samples thus evaluated were used in the additional evaluation of GPC3-IHC. The median measurement of staining of preparations obtained from 14 cases was carried out by Ventana Medical Systems, Inc. (USA) according to an instruction attached to anti-glypican 3 Mouse GC33 Monoclonal Primary Antibody (Ventana Medical Systems, Inc.) using an automatic staining apparatus BenchMark (manufactured by Ventana Medical Systems, Inc.). In GPC3-IHC (staining method 2) carried out by Ventana Medical Systems, Inc., the preparations were stained according to the attached instruction and then scored on 4 scales of 0 to 3+ in terms of the degree, intensity, etc. of staining in tumor cells. As a result, distribution shown in Table 7 was obtained.

TABLE 7

| GPC3-IHC score | The number of patients (percentage to 14 evaluable cases) |
|---|---|
| 3+ | 3 (21.4%) |
| 2+ | 1 (7.1%) |
| 1+ | 7 (50%) |
| 0+ | 3 (21.4%) |

In the staining method 2, cases exhibiting long-period SD were included at a high percentage and with no omission in a 2+/3+ group when the cases were divided into two groups (with a score of 0 and 1+ and with a score of 2+ and 3+) (Table 8).

TABLE 8

| GPC3-IHC score | High-value group | | Low-value group | |
|---|---|---|---|---|
| 1+/2+/3+ | 18% | (2/11) | 0% | (0/3) |
| 2+/3+ | 50% | (2/4) | 0% | (0/10) |
| 3+ | 33% | (1/3) | 9% | (1/11) |

Example 3

The concentration of free GPC3 was measured in the serum of patients who received the administration of GC33 in GPC3-targeting treatment. Mouse anti-GPC3 monoclonal antibodies M3C11 and L9G11 (WO2004/022739) were each diluted into 7.5 µg/mL with an immobilizing buffer (0.05 mol/L sodium bicarbonate, pH 9.6) and then dispensed to a plate at a concentration of 100 µL/well. Then, the plate was left standing at room temperature for 1 hour. Each well was washed three times with a washing buffer (0.05 mol/L tris-buffered saline, pH 8.0, 0.05% Tween-20). Then, a blocking buffer (25 mmol/L tris-HCl buffer, pH 8.1, 0.5 mmol/L magnesium chloride, 72 mmol/L sodium chloride, 0.05% ProClin 150, 5 mg/mL bovine serum albumin, 0.025% Tween-20, 1% Block Ace) was dispensed thereto at a concentration of 200 µL/well. The plate was left standing at room temperature for 2 hours to prepare an antibody-immobilized plate. If the plate was not immediately used, the plate was stored at 4° C. and then used in the measurement.

The serum of each patient collected in the clinical trial was diluted 4-fold with a diluting buffer (25 mmol/L tris-HCl buffer, pH 8.1, 0.5 mmol/L magnesium chloride, 72 mmol/L sodium chloride, 0.05% ProClin 150, 5 mg/mL bovine serum albumin, 0.025% Tween-20, 0.4% Block Ace) and added to the plate at a concentration of 100 µL/well. The plate was left standing overnight at 4° C. The GPC3 standard used was recombinant GPC3 with serine residues at positions 495 and 509 substituted by alanine residues so as not to permit the binding of heparan sulfate sugar chains (Hippo et al., Cancer Res. (2004) 64, 2418-2423).

Subsequently, each well of the plate was washed three times with a washing buffer, and a biotin-labeled anti-glypican-3 polyclonal antibody (manufactured by R&D systems, Inc.) diluted into 0.3 µg/mL with a diluting buffer was added thereto at a concentration of 100 µL/well. The plate was further left standing at 25° C. for 1 hour, and each well was washed three times with a washing buffer. Then, HRP-labeled streptavidin (Streptavidin-Poly HRP80; manufactured by Stereospecific Detection Technologies (SDT)) diluted with a diluting buffer according to the instruction was added thereto at a concentration of 100 µL/well. The plate was left standing at 25° C. for 1 hour. Then, each well of the plate was washed three times with a washing buffer. Then, color was developed using TMB Microwell Peroxidase Substrate System (manufactured by Kirkegaard & Perry Laboratories Inc.) according to the instruction attached to the kit. The absorbance of the reaction solution in each well was measured at 450 nm and 650 nm. A calibration curve prepared on the basis of the standard sample containing the recombinant GPC3 was used to calculate the GPC3 antigen level in the serum of each patient from the obtained absorbance of each well.

Example 4

Figure 4:
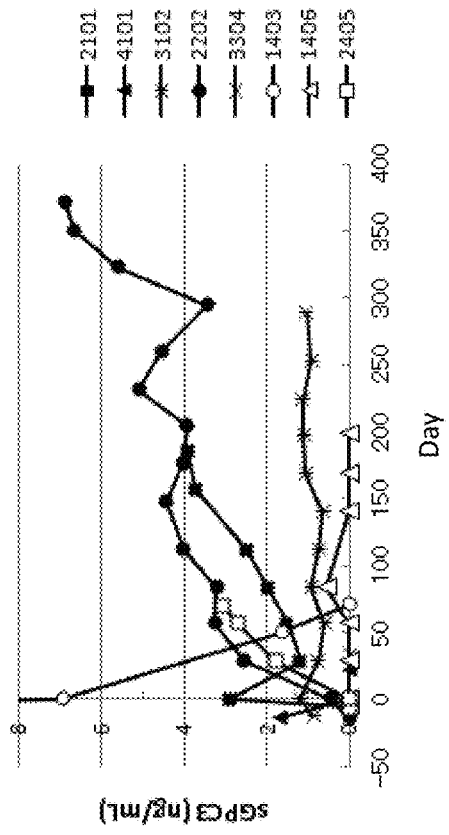
FIG. 4A is a diagram showing the correlation between the concentration of free GPC3 detected in serum and the GPC3-IHC score of tumor tissues, in a group evaluated as having high expression of GPC3. The ordinate shows the serum concentration (ng/mL) of free GPC3. The abscissa shows the number of lapsed days (day) after the start of GPC3-targeting drug therapy.
FIG. 4B is a diagram showing the correlation between the concentration of free GPC3 detected in serum and the GPC3-IHC score of tumor tissues, in a group evaluated as having low expression of GPC3 or being negative. The ordinate shows the serum concentration (ng/mL) of free GPC3. The abscissa shows the number of lapsed days (day) after the start of GPC3-targeting drug therapy.
Figure 4:
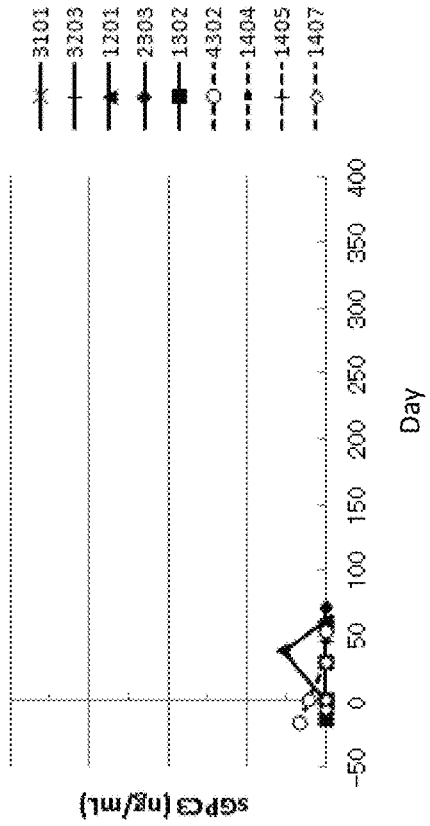

Change in the serum concentration of detected free GPC3 calculated in Example 3 is shown in FIG. 4 for two groups, i.e., the high-value group and the low-value group, of tumor tissue GPC3-IHC scores determined in Example 2. A large number of cases with a measurable level of free GPC3 was included in the group evaluated as having high expression of GPC3 on the basis of the GPC3-IHC score (FIG. 4A). A rise in the concentration of free GPC3 or stabilization thereof was observed in cases exhibiting long SD. By contrast, a small number of cases with a measurable level of free GPC3 was included in the group evaluated as having low expression of GPC3 or being negative on the basis of the GPC3-IHC score (FIG. 4B).

Figure 5A:
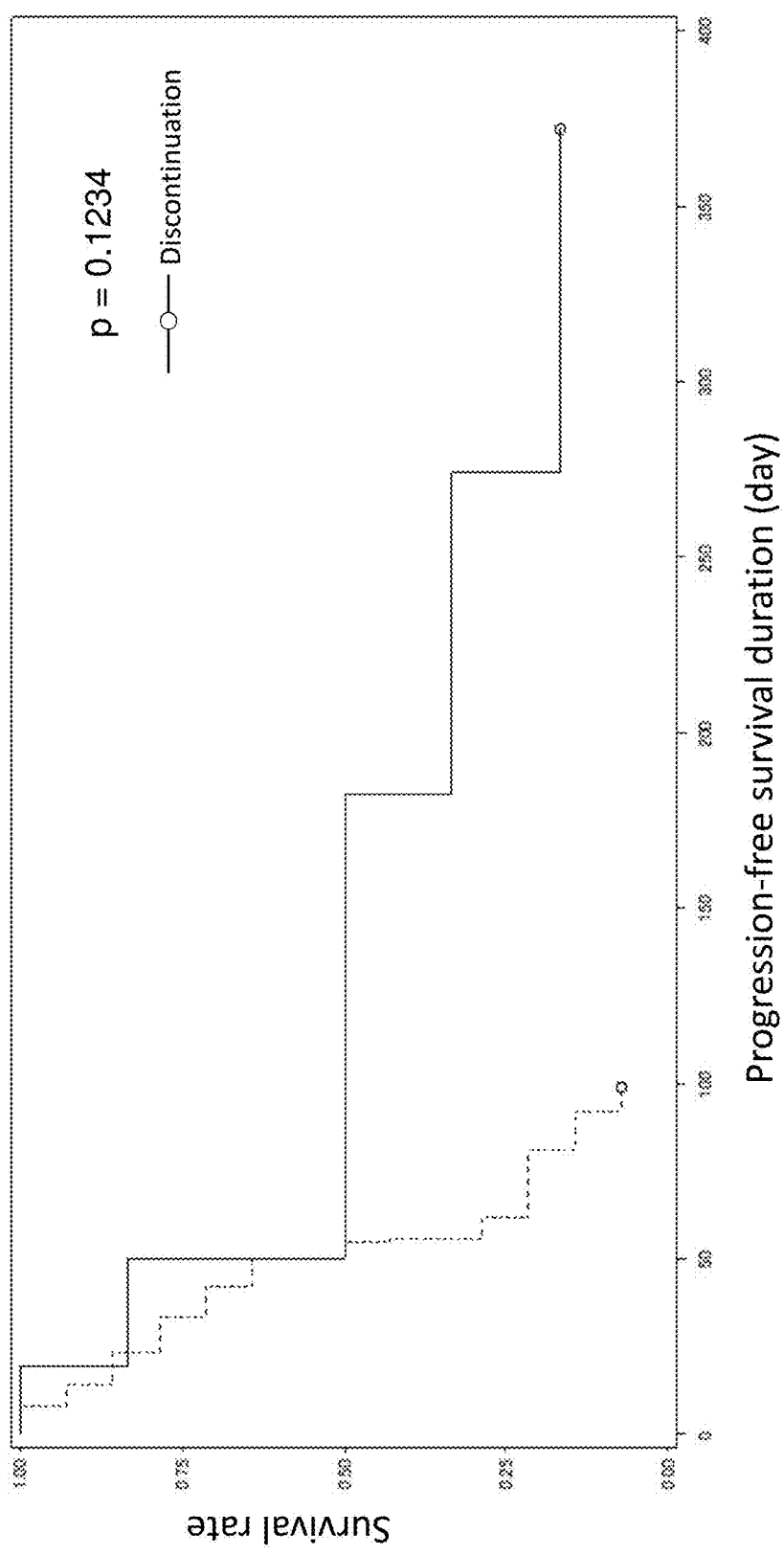
FIG. 5A is a diagram showing the correlation between the concentration of free GPC3 in serum isolated from serum collected from patients before the start of GPC3-targeting drug therapy and the progression-free survival duration of the patients. The ordinate shows a survival rate. The abscissa shows progression-free survival duration (day) after the start of GPC3-targeting drug therapy. The solid line represents the progression-free survival duration of a group having a measurable level of free GPC3 (6 cases). The broken line represents the progression-free survival duration of a group having a GPC3 level below the measurement limit (0.4 ng/mL) (14 cases).
Figure 5B:
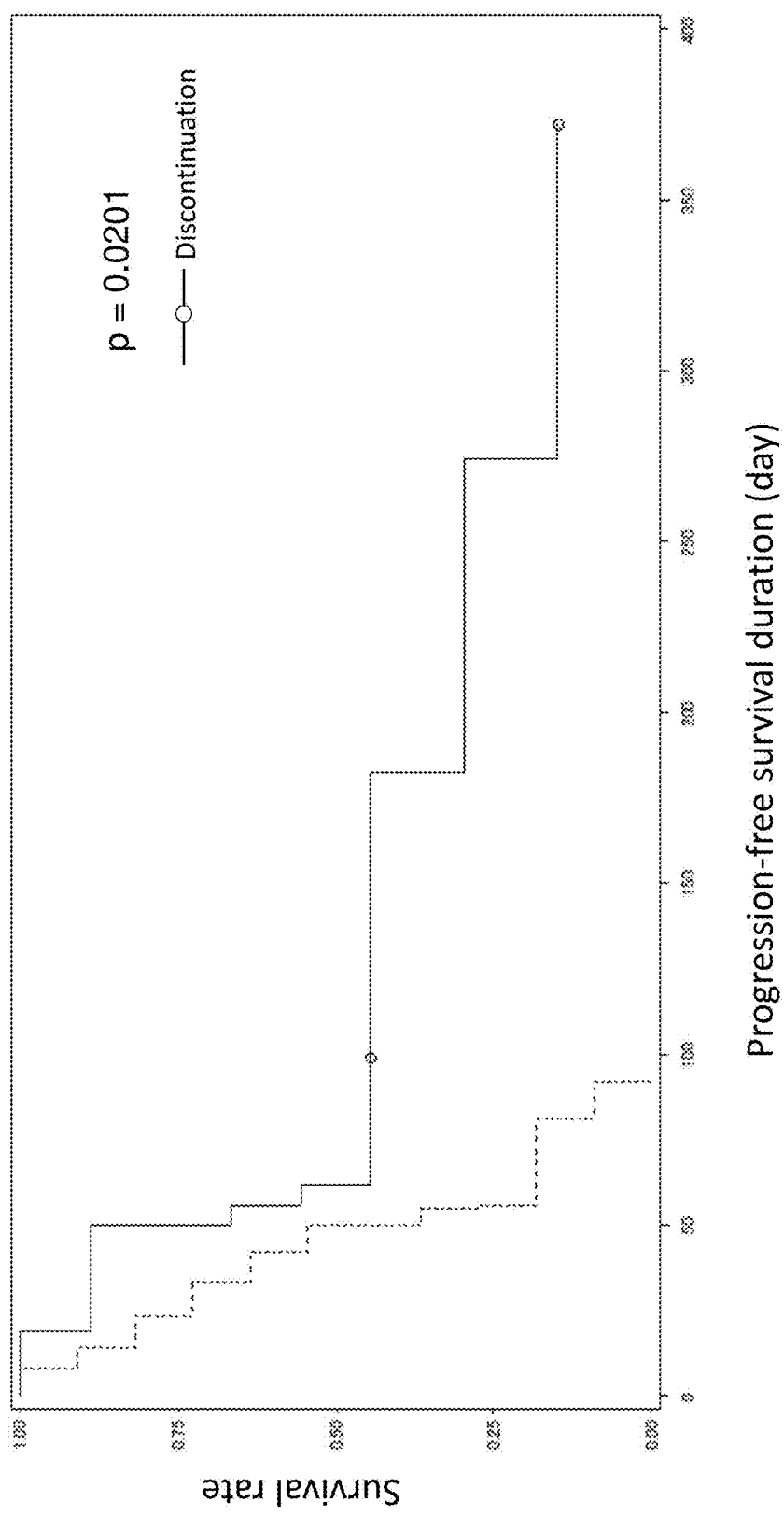
FIG. 5B is a diagram showing the correlation between the concentration of free GPC3 in serum isolated from serum collected from patients during a test period (including before and after the start of GPC3-targeting drug therapy) and the progression-free survival duration of the patients. The ordinate shows a survival rate. The abscissa shows progression-free survival duration (day) after the start of GPC3-targeting drug therapy. The solid line represents the progression-free survival duration of a group having a measurable level of free GPC3 (9 cases) in serum isolated from serum collected from the patients before or during GPC3-targeting drug therapy. The broken line represents the progression-free survival duration of a group having a GPC3 level below the measurement limit (0.4 ng/mL) (both before and after the start of GPC3-targeting drug therapy) (11 cases) in serum isolated from serum collected from the patients treated with the therapy.

Progression-free survival duration or progression-free survival (PFS) was compared between a group having a measurable level of GPC3 in serum collected during screening or before initial administration (GPC3-positive group) and a group with a GPC3 level below the detection limit. The PFS of the serum GPC3-positive group before the practice of GPC3-targeting treatment was confirmed to be longer than that of the negative group (FIG. 5A). A logrank test was further conducted if the serum GPC3-positive group involved serum in which serum GPC3 was measured after the start of administration of the GPC3-targeting drug. The test results showed that the PFS of this group was significantly longer than that of the negative group (cases with a GPC3 level below the measurement limit, regardless of before or after administration of the GPC3-targeting drug) and the positive group (FIG. 5B).

Example 5

As shown in Tables 9 and 10, serum GPC3-positive high-value groups of GPC3-IHC scores evaluated using the staining method 1 and the staining method 2 were shown to have a higher percentage of long SD than that of the high-value group of GPC3-IHC scores (Tables 6 and 8 to 10).

TABLE 9

| GPC3-IHC (staining method 1) | Serum GPC3-positive with high IHC value (7 or higher) | | Others | |
|---|---|---|---|---|
| Serum GPC3 before administration GPC3 | 60% | (3/5) | 9% | (1/11) |
| Serum GPC3 after administration GPC3 | 80% | (4/5) | 0% | (0/11) |

TABLE 10

| GPC3-IHC (staining method 2) | Serum GPC3-positive with IHC (2-3+) | | Others | |
|---|---|---|---|---|
| Serum GPC3 before administration GPC3 | 100% | (2/2) | 0% | (0/12) |
| Serum GPC3 after administration GPC3 | 67% | (2/3) | 0% | (0/11) |

Example 6

Figure 6A:
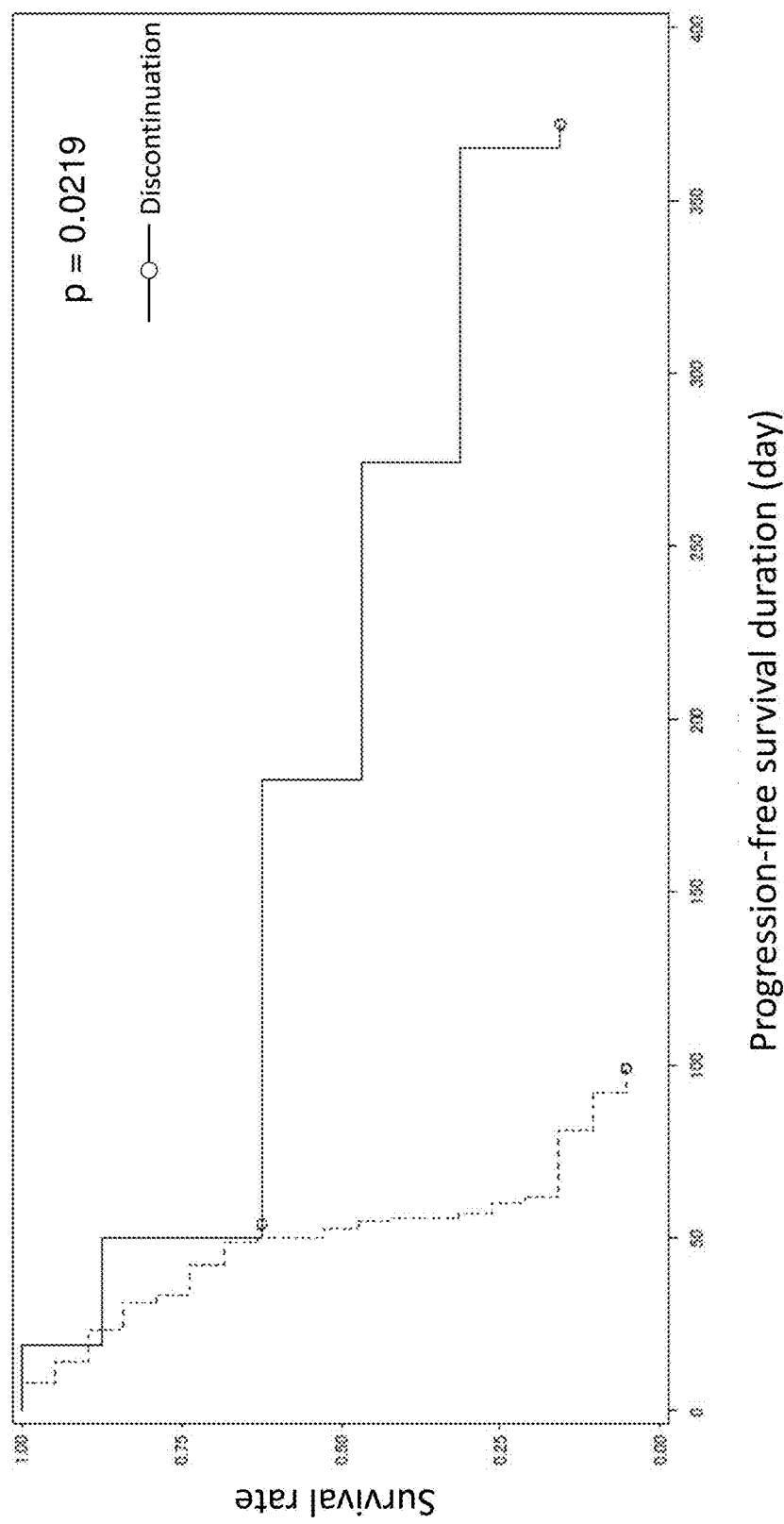
FIG. 6A is a diagram showing the correlation between the concentration of free GPC3 in serum isolated from serum collected from patients before the start of GPC3-targeting drug therapy and the progression-free survival duration of the patients. The ordinate shows a survival rate. The abscissa shows progression-free survival duration (day) after the start of GPC3-targeting drug therapy. The solid line represents the progression-free survival duration of a group having a measurable level of free GPC3 (8 cases). The broken line represents the progression-free survival duration of a group having a GPC3 level below the measurement limit (0.4 ng/mL) (19 cases). The hazard ratio of the group with a detectable level of GPC3 to the group with a GPC3 level below the detection limit was 0.265 (95% confidence interval: 0.077-0.914, p=0.0219).
Figure 6B:
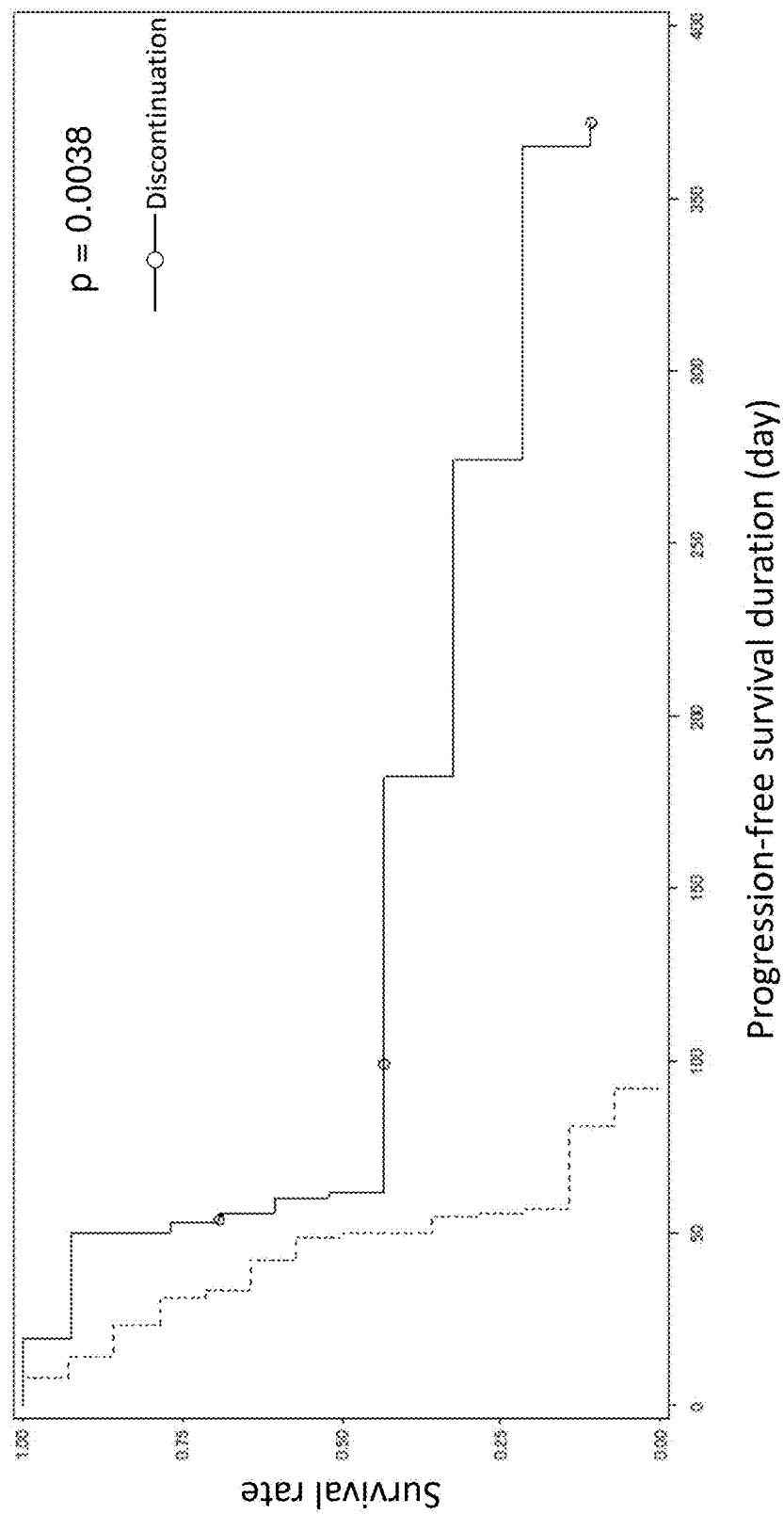
FIG. 6B is a diagram showing the correlation between the concentration of free GPC3 in serum isolated from serum collected from patients during a test period (including before and after the start of GPC3-targeting drug therapy) and the progression-free survival duration of the patients. The ordinate shows a survival rate. The abscissa shows progression-free survival duration (day) after the start of GPC3-targeting drug therapy. The solid line represents the progression-free survival duration of a group having a measurable level of free GPC3 (13 cases) in serum isolated from serum collected from the patients before or during GPC3-targeting drug therapy. The broken line represents the progression-free survival duration of a group having a GPC3 level below the measurement limit (0.4 ng/mL) (both before and after the start of GPC3-targeting drug therapy) (14 cases) in serum isolated from serum collected from the patients treated with the therapy. The hazard ratio of the group with a detectable level of GPC3 to the group with a GPC3 level below the detection limit was 0.283 (95% confidence interval: 0.112-0.715, p=0.0038).
Figure 7A:
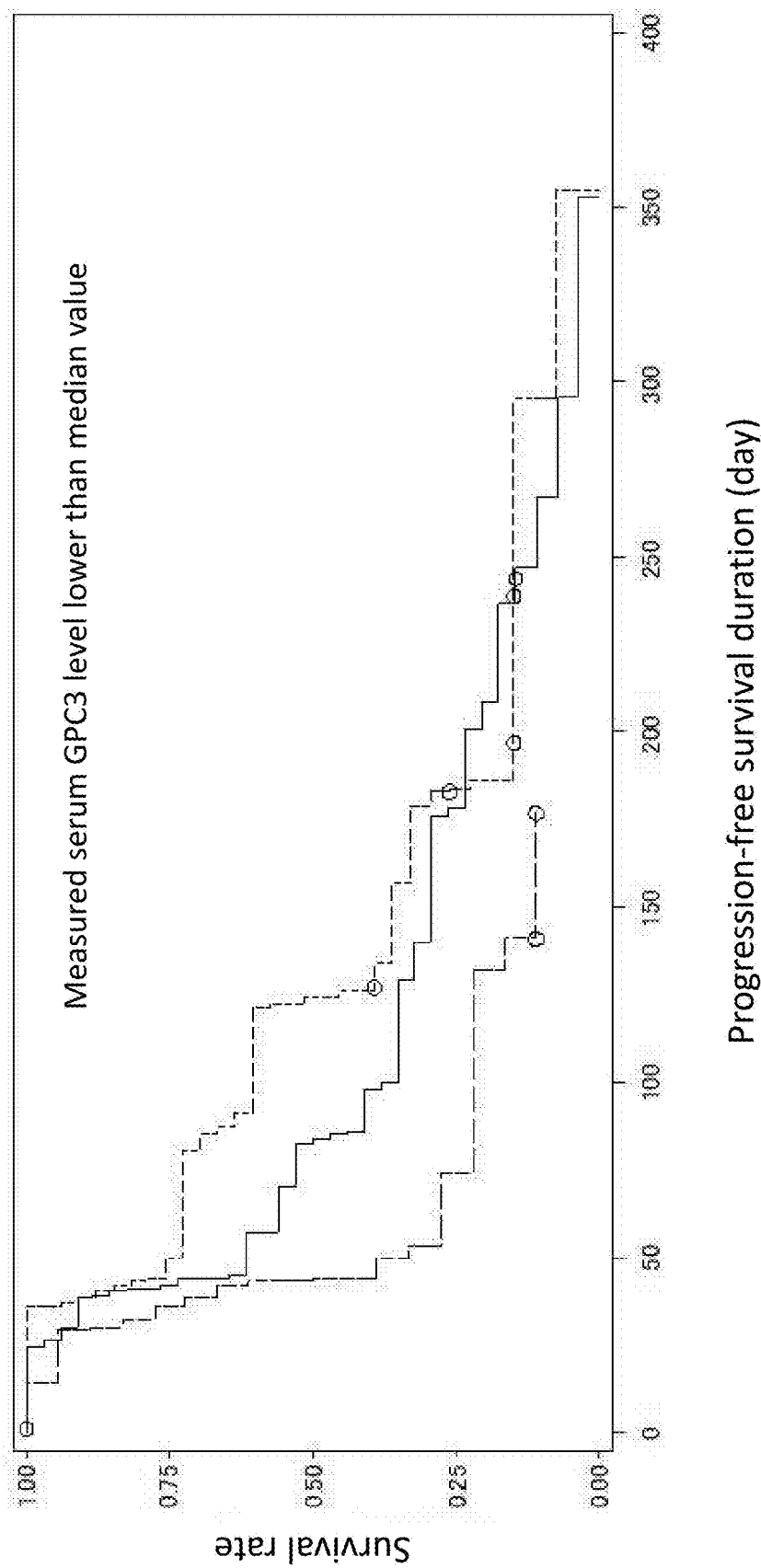
FIG. 7A is a diagram showing the correlation between the serum concentration of free GPC3 isolated from serum collected from patients before the start of GPC3-targeting drug therapy and the progression-free survival duration of the patients in a group with the serum concentration of free GPC3 lower than the median value (1129.7 pg/mL). The solid line represents the progression-free survival duration of a placebo group (34 cases). The broken line represents the progression-free survival duration of a group with a putative trough level of GC33 lower than the median value (low-GC33-exposed group: 19 cases). The dotted line represents the progression-free survival duration of a group with a putative trough level of GC33 equal to or higher than the median value (high-GC33-exposed group: 34 cases). The median value of the progression-free survival duration was 83 days for the placebo group, 43.5 days for the low-GC33-exposed group, and 124 days for the high-GC33-exposed group. The hazard ratio of the high-GC33-exposed group to the placebo group was 0.803 (p=0.397), whereas the hazard ratio of the high-GC33-exposed group to the low-GC33-exposed group was 0.425 (p=0.010).
Figure 7B:
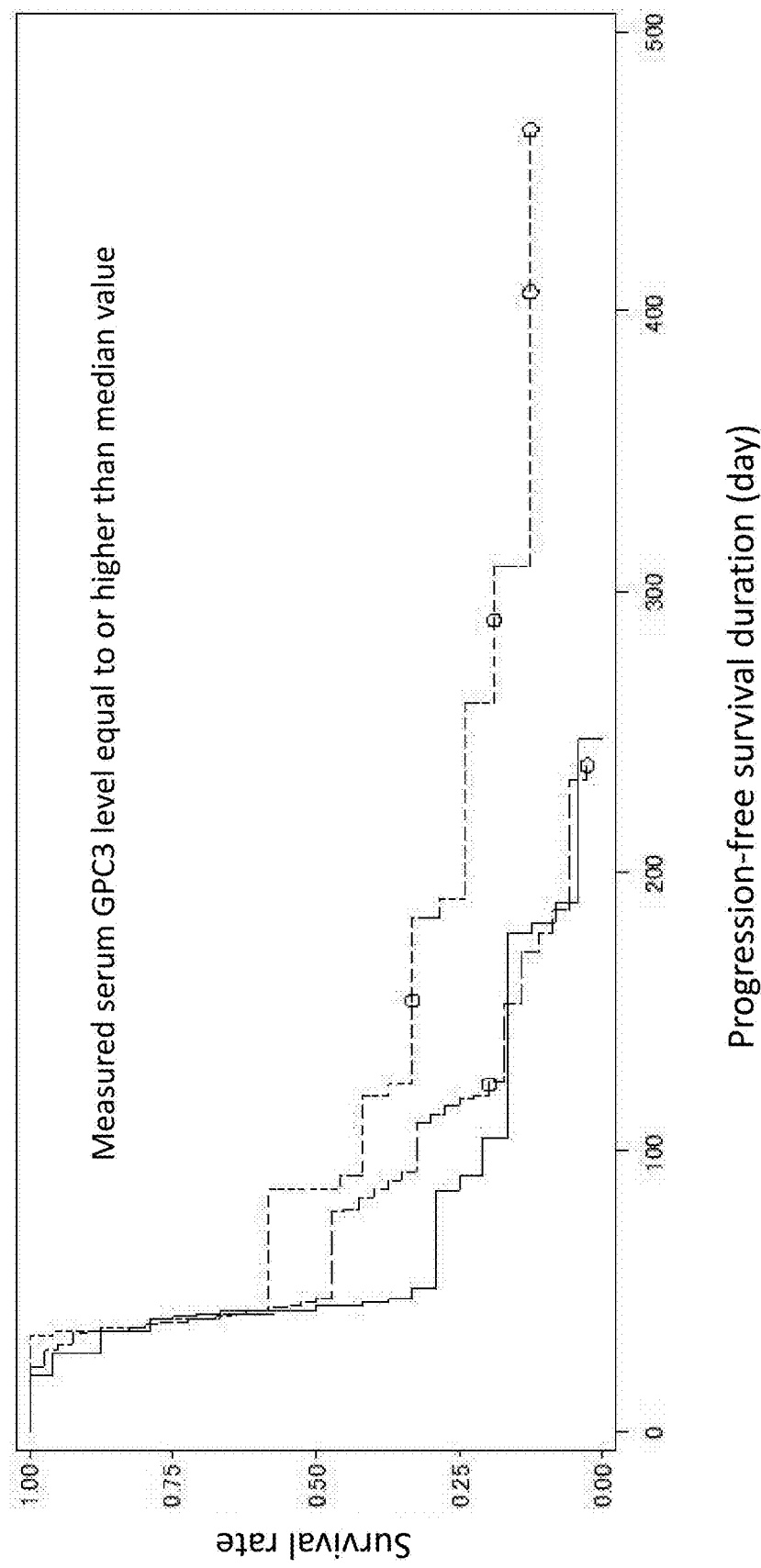
FIG. 7B is a diagram showing the correlation between the serum concentration of free GPC3 isolated from serum collected from patients before the start of GPC3-targeting drug therapy and the progression-free survival duration of the patients in a group with the serum concentration of free GPC3 equal to or higher than the median value (1129.7 pg/mL). The solid line represents the progression-free survival duration of a placebo group (24 cases). The broken line represents the progression-free survival duration of a low-GC33-exposed group (40 cases). The dotted line represents the progression-free survival duration of a high-GC33-exposed group (24 cases). The median value of the progression-free survival duration was 44 days for the placebo group, 46.5 days for the low-GC33-exposed group, and 87 days for the high-GC33-exposed group. The hazard ratio of the high-GC33-exposed group to the placebo group was 0.510 (p=0.036), whereas the hazard ratio of the high-GC33-exposed group to the low-GC33-exposed group was 0.572 (p=0.056).
Figure 7C:
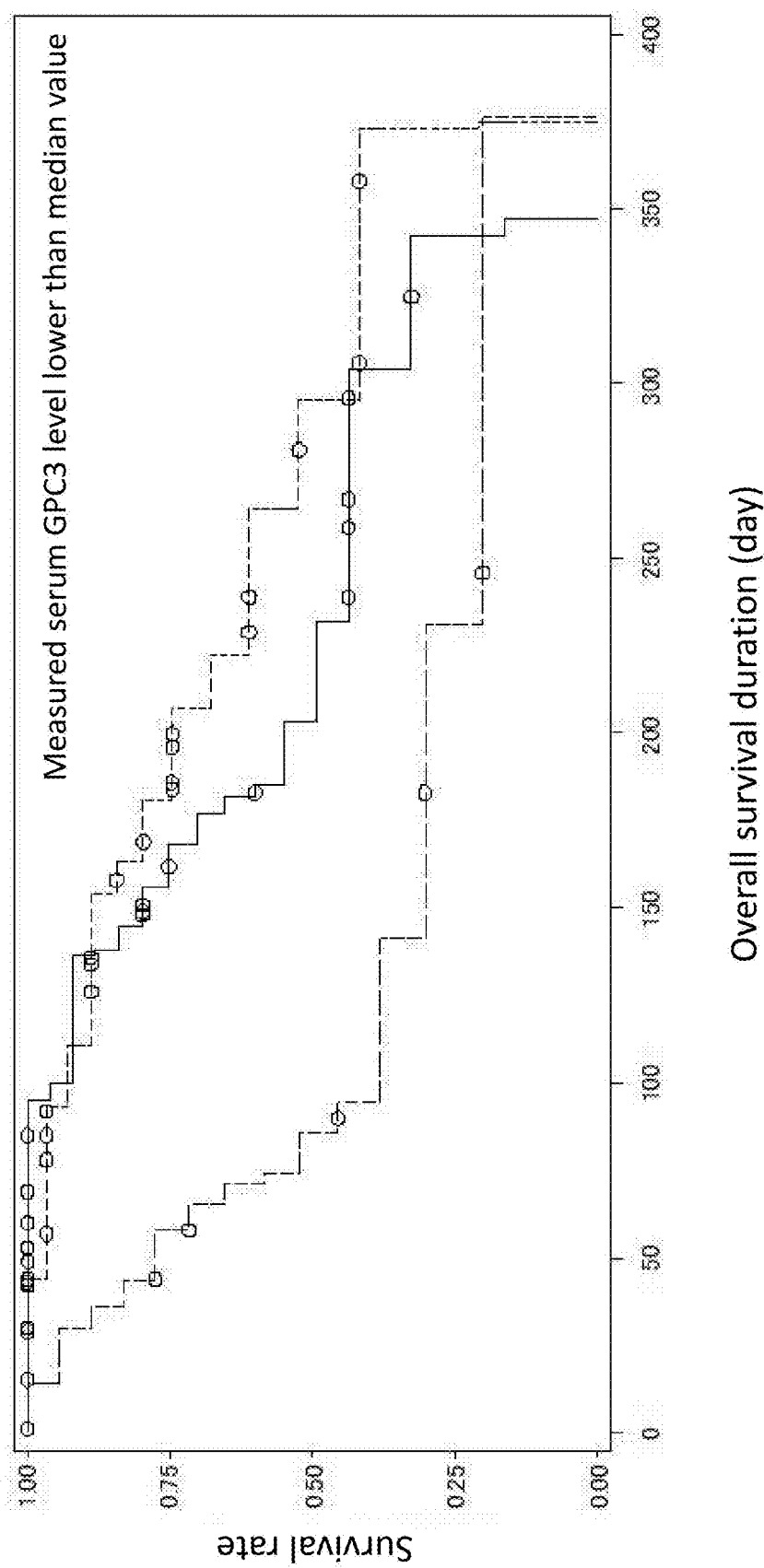
FIG. 7C is a diagram showing the correlation between the serum concentration of free GPC3 isolated from serum collected from patients before the start of GPC3-targeting drug therapy and the overall survival duration of the patients in a group with the serum concentration of free GPC3 lower than the median value (1129.7 pg/mL). The solid line represents the overall survival duration of a placebo group (34 cases). The broken line represents the overall survival duration of a low-GC33-exposed group (19 cases). The dotted line represents the overall survival duration of a high-GC33-exposed group (34 cases). The median value of the overall survival duration was 203 days for the placebo group, 86 days for the low-GC33-exposed group, and 295 days for the high-GC33-exposed group. The hazard ratio of the high-GC33-exposed group to the placebo group was 0.590 (p=0.200), whereas the hazard ratio of the high-GC33-exposed group to the low-GC33-exposed group was 0.329 (p=0.008).
Figure 7D:
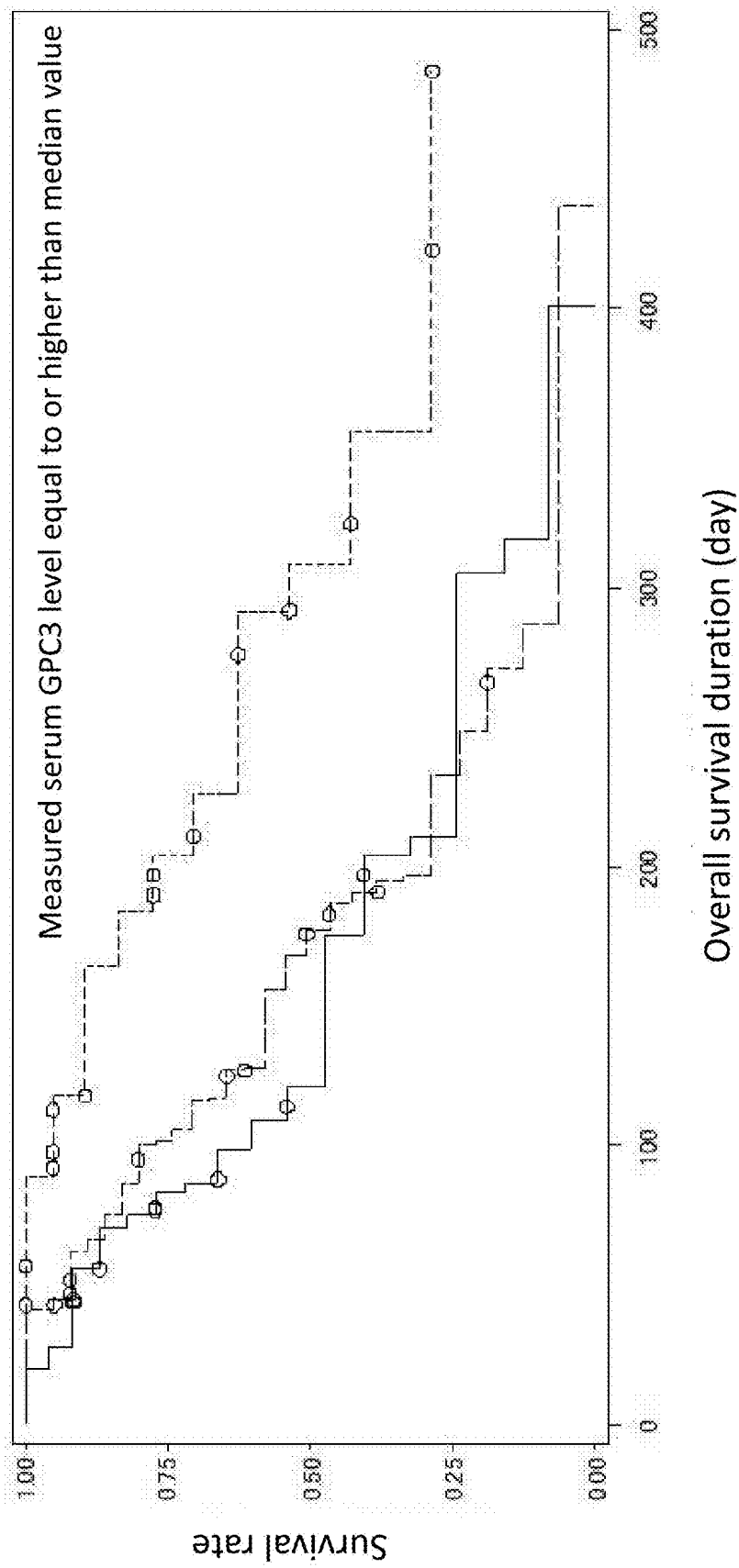
FIG. 7D is a diagram showing the correlation between the serum concentration of free GPC3 isolated from serum collected from patients before the start of GPC3-targeting drug therapy and the overall survival duration of the patients in a group with the serum concentration of free GPC3 equal to or higher than the median value (1129.7 pg/mL). The solid line represents the overall survival duration of a placebo group (24 cases). The broken line represents the overall survival duration of a low-GC33-exposed group (40 cases). The dotted line represents the overall survival duration of a high-GC33-exposed group (24 cases). The median value of the overall survival duration was 121 days for the placebo group, 177 days for the low-GC33-exposed group, and 308 days for the high-GC33-exposed group. The hazard ratio of the high-GC33-exposed group to the placebo group was 0.303 (p=0.005), whereas the hazard ratio of the high-GC33-exposed group to the low-GC33-exposed group was 0.280 (p=0.002).
Figure 7E:
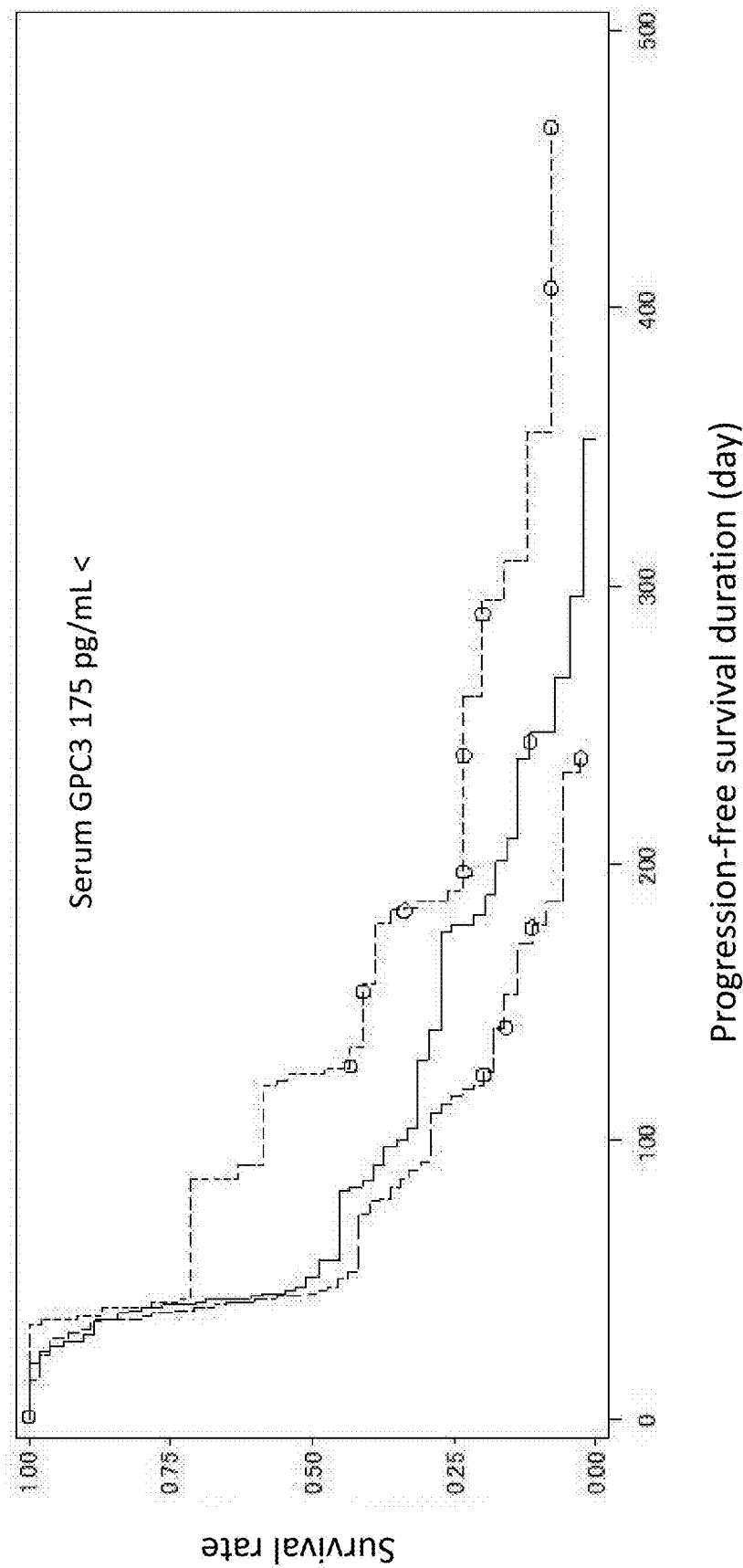
FIG. 7E is a diagram showing the correlation between the serum concentration of free GPC3 isolated from serum collected from patients before the start of GPC3-targeting drug therapy and the progression-free survival duration of the patients in a group with the serum concentration of free GPC3 higher than 175 pg/mL. The solid line represents the progression-free survival duration of a placebo group (51 cases). The broken line represents the progression-free survival duration of a low-GC33-exposed group (56 cases). The dotted line represents the progression-free survival duration of a high-GC33-exposed group (47 cases). The median value of the progression-free survival duration was 51 days for the placebo group, 45 days for the low-GC33-exposed group, and 124 days for the high-GC33-exposed group. The hazard ratio of the high-GC33-exposed group to the placebo group was 0.597 (p=0.0184), whereas the hazard ratio of the high-GC33-exposed group to the low-GC33-exposed group was 0.439 (p=0.0003).
Figure 7F:
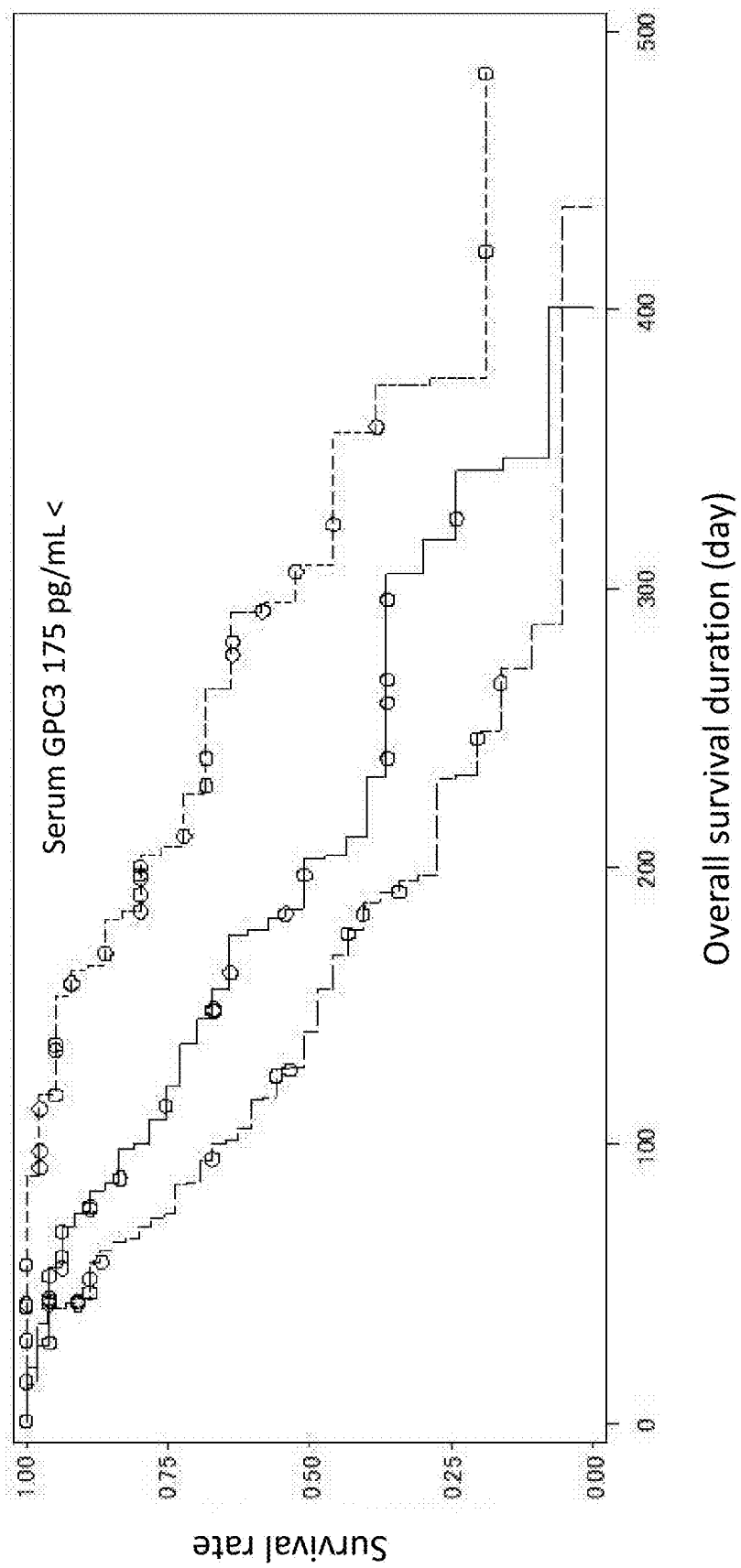
FIG. 7F is a diagram showing the correlation between the serum concentration of free GPC3 isolated from serum collected from patients before the start of GPC3-targeting drug therapy and the overall survival duration of the patients in a group with the serum concentration of free GPC3 higher than 175 pg/mL. The solid line represents the overall survival duration of a placebo group (51 cases). The broken line represents the overall survival duration of a low-GC33-exposed group (56 cases). The dotted line represents the overall survival duration of a high-GC33-exposed group (47 cases). The median value of the overall survival duration was 203 days for the placebo group, 141 days for the low-GC33-exposed group, and 308 days for the high-GC33-exposed group. The hazard ratio of the high-GC33-exposed group to the placebo group was 0.402 (p=0.0037), whereas the hazard ratio of the high-GC33-exposed group to the low-GC33-exposed group was 0.238 (p=<0.0001).
Figure 8A:
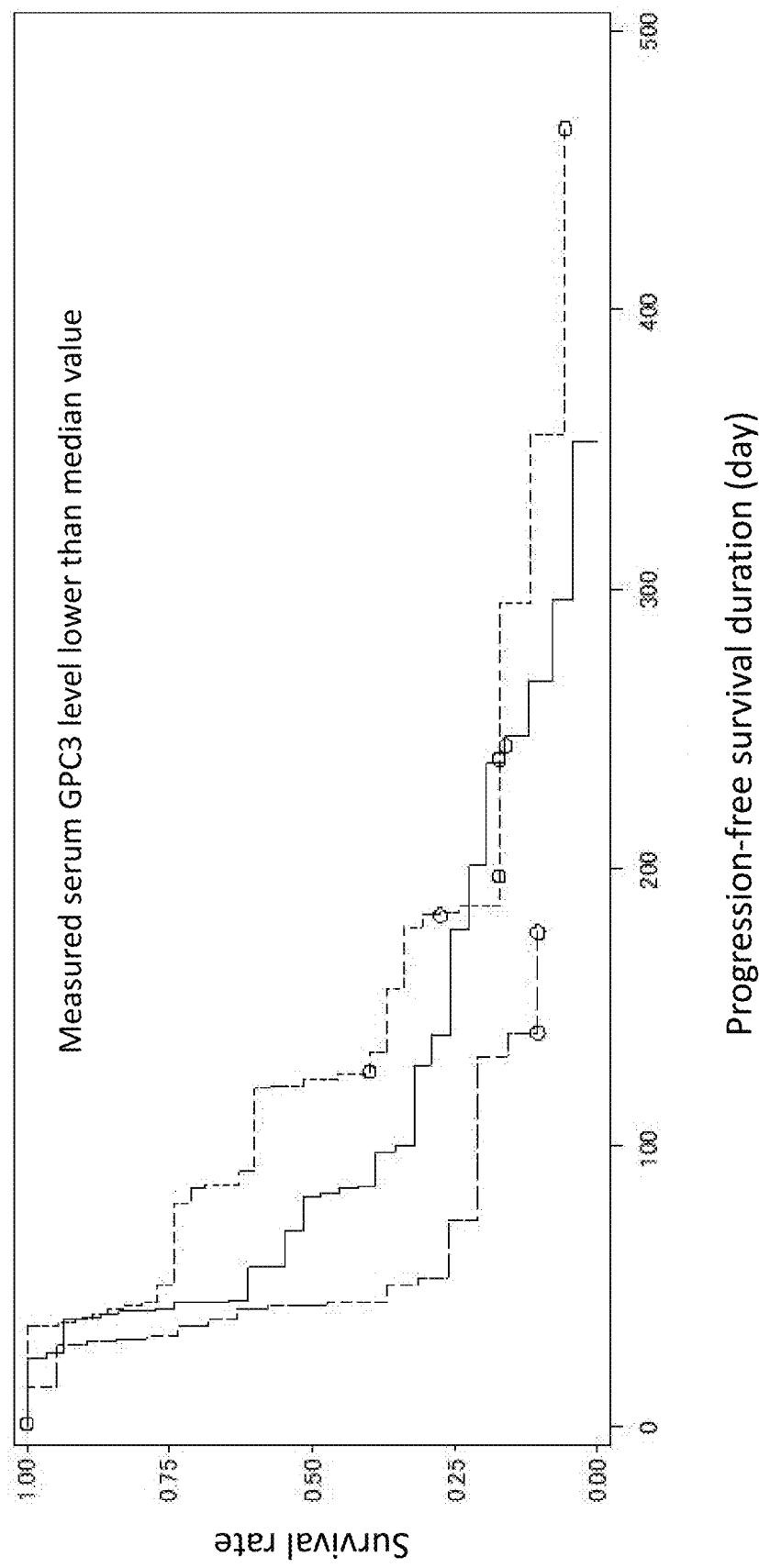
FIG. 8A is a diagram showing the correlation between the serum concentration of free GPC3 isolated from serum collected from patients before the start of GPC3-targeting drug therapy and the progression-free survival duration of the patients in a group with the serum concentration of free GPC3 lower than the median value (1161.5 pg/mL). The solid line represents the progression-free survival duration of a placebo group (31 cases). The broken line represents the progression-free survival duration of a low-GC33-exposed group (20 cases). The dotted line represents the progression-free survival duration of a high-GC33-exposed group (36 cases). The median value of the progression-free survival duration was 82 days for the placebo group, 43 days for the low-GC33-exposed group, and 124 days for the high-GC33-exposed group. The hazard ratio of the high-GC33-exposed group to the placebo group was 0.713 (p=0.197), whereas the hazard ratio of the high-GC33-exposed group to the low-GC33-exposed group was 0.392 (p=0.004).
Figure 8B:
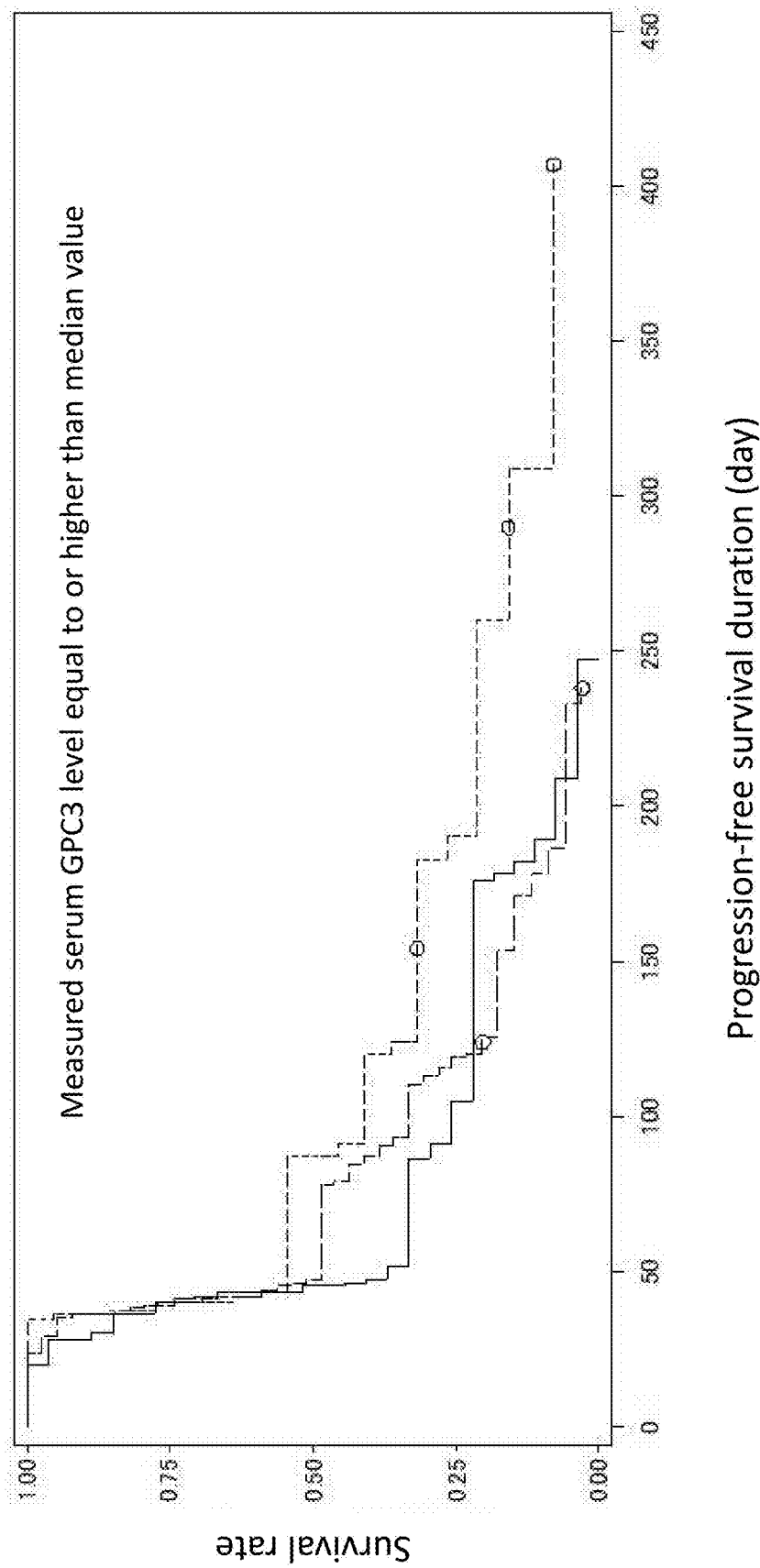
FIG. 8B is a diagram showing the correlation between the serum concentration of free GPC3 isolated from serum collected from patients before the start of GPC3-targeting drug therapy and the progression-free survival duration of the patients in a group with the serum concentration of free GPC3 equal to or higher than the median value (1161.5 pg/mL). The solid line represents the progression-free survival duration of a placebo group (27 cases). The broken line represents the progression-free survival duration of a low-GC33-exposed group (39 cases). The dotted line represents the progression-free survival duration of a high-GC33-exposed group (22 cases). The median value of the progression-free survival duration was 45 days for the placebo group, 47 days for the low-GC33-exposed group, and 87 days for the high-GC33-exposed group. The hazard ratio of the high-GC33-exposed group to the placebo group was 0.588 (p=0.092), whereas the hazard ratio of the high-GC33-exposed group to the low-GC33-exposed group was 0.626 (p=0.116).
Figure 8C:
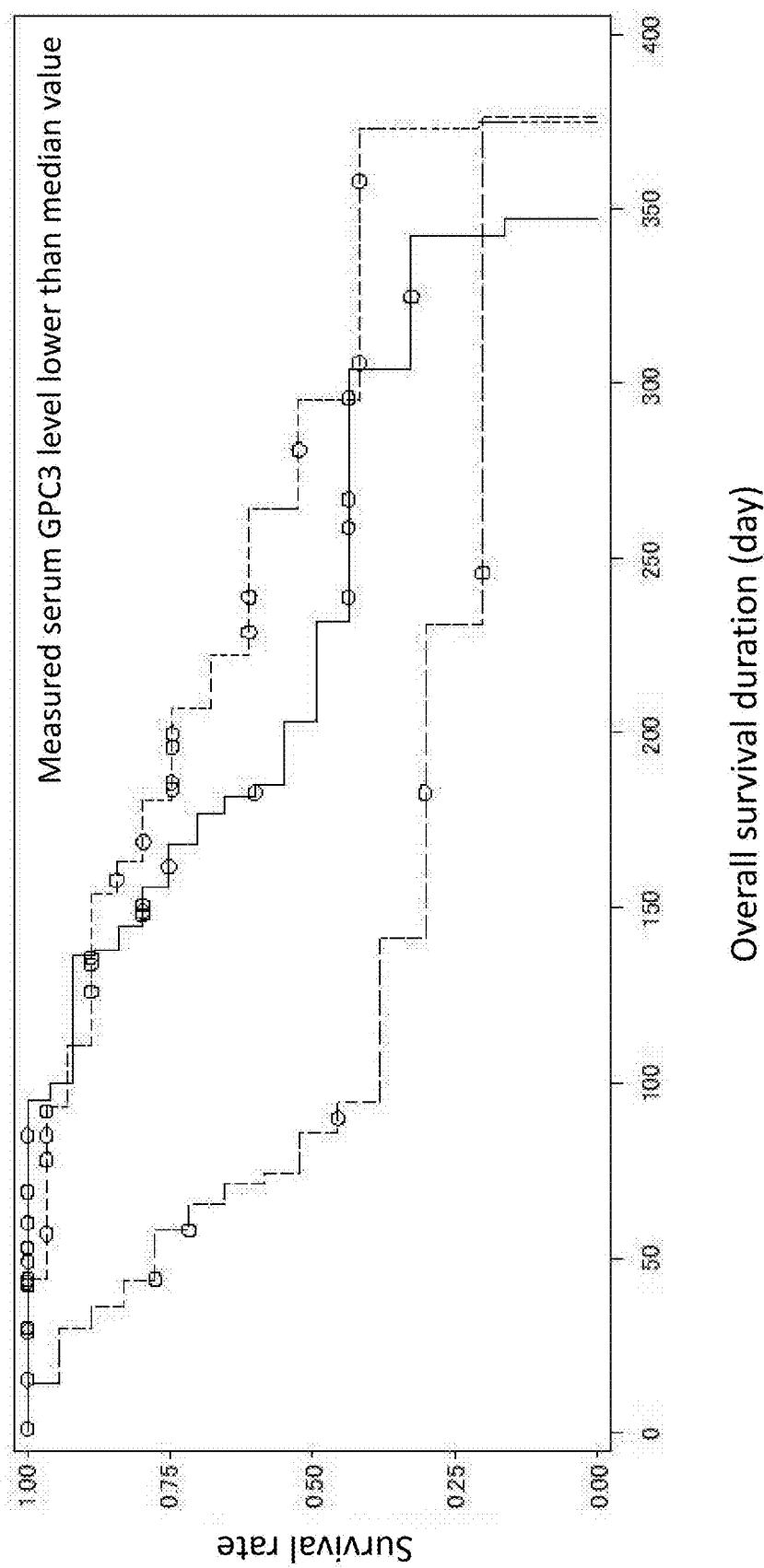
FIG. 8C is a diagram showing the correlation between the serum concentration of free GPC3 isolated from serum collected from patients before the start of GPC3-targeting drug therapy and the overall survival duration of the patients in a group with the serum concentration of free GPC3 lower than the median value (1161.5 pg/mL). The solid line represents the overall survival duration of a placebo group (31 cases). The broken line represents the overall survival duration of a low-GC33-exposed group (20 cases). The dotted line represents the overall survival duration of a high-GC33-exposed group (36 cases). The median value of the overall survival duration was 203 days for the placebo group, 86 days for the low-GC33-exposed group, and 295 days for the high-GC33-exposed group. The hazard ratio of the high-GC33-exposed group to the placebo group was 0.508 (p=0.100), whereas the hazard ratio of the high-GC33-exposed group to the low-GC33-exposed group was 0.287 (p=0.002).
Figure 8D:
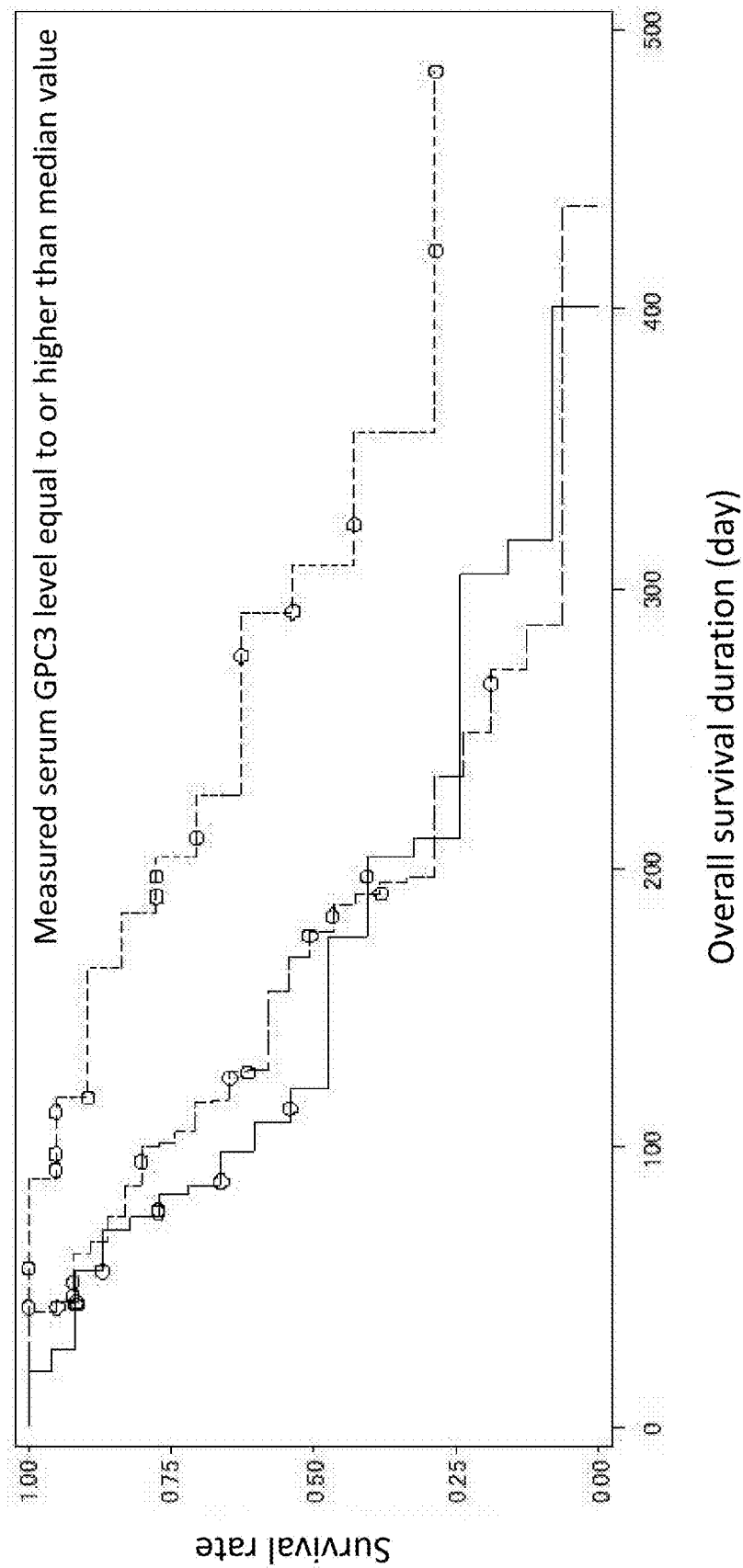
FIG. 8D is a diagram showing the correlation between the serum concentration of free GPC3 isolated from serum collected from patients before the start of GPC3-targeting drug therapy and the overall survival duration of the patients in a group with the serum concentration of free GPC3 equal to or higher than the median value (1161.5 pg/mL). The solid line represents the overall survival duration of a placebo group (27 cases). The broken line represents the overall survival duration of a low-GC33-exposed group (39 cases). The dotted line represents the overall survival duration of a high-GC33-exposed group (22 cases). The median value of the overall survival duration was 176 days for the placebo group, 177 days for the low-GC33-exposed group, and 291 days for the high-GC33-exposed group. The hazard ratio of the high-GC33-exposed group to the placebo group was 0.300 (p=0.022), whereas the hazard ratio of the high-GC33-exposed group to the low-GC33-exposed group was 0.324 (p=0.005).
Figure 8E:
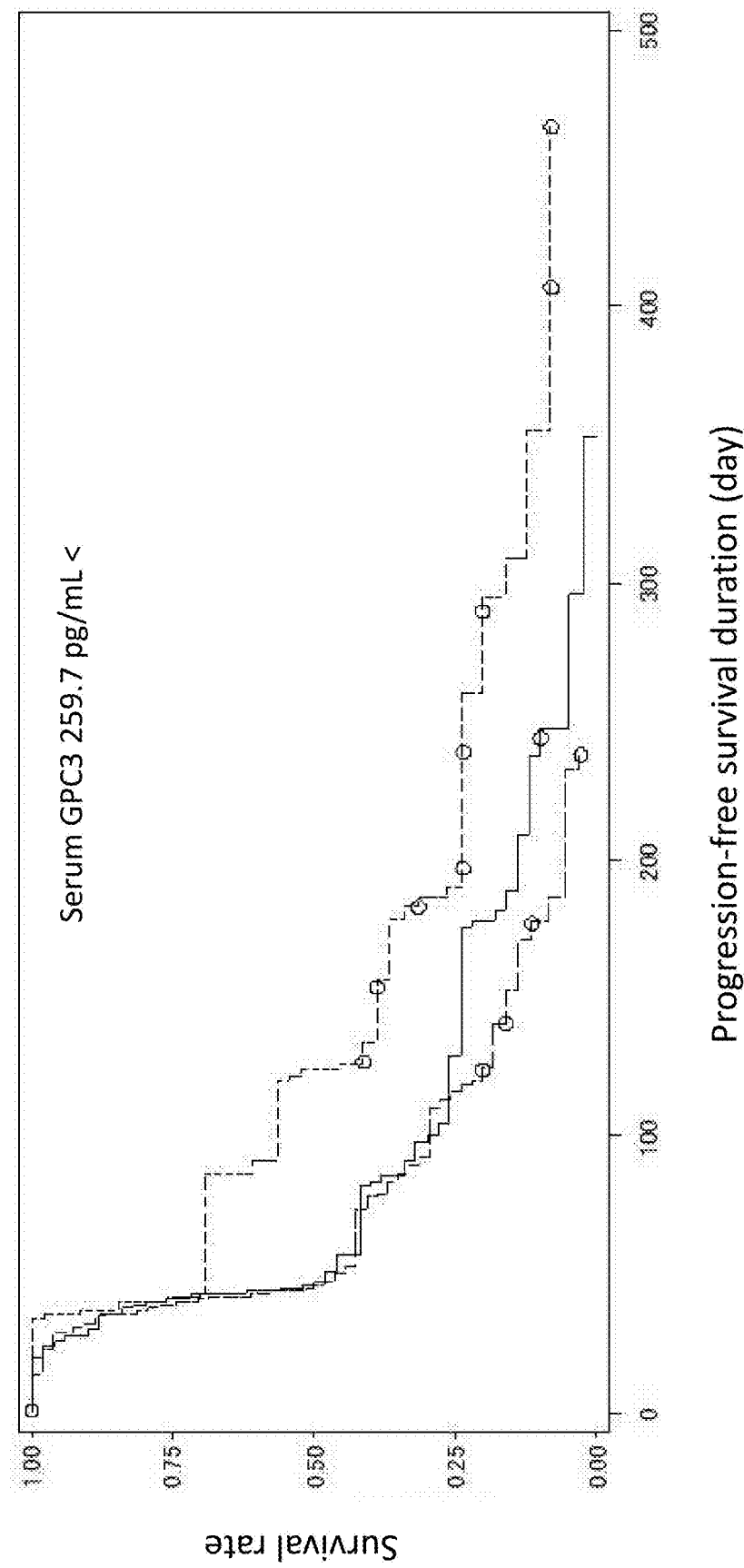
FIG. 8E is a diagram showing the correlation between the serum concentration of free GPC3 isolated from serum collected from patients before the start of GPC3-targeting drug therapy and the progression-free survival duration of the patients in a group with the serum concentration of free GPC3 higher than 259.7 pg/mL. The solid line represents the progression-free survival duration of a placebo group (50 cases). The broken line represents the progression-free survival duration of a low-GC33-exposed group (55 cases). The dotted line represents the progression-free survival duration of a high-GC33-exposed group (47 cases). The median value of the progression-free survival duration was 46.5 days for the placebo group, 45.5 days for the low-GC33-exposed group, and 124 days for the high-GC33-exposed group. The hazard ratio of the high-GC33-exposed group to the placebo group was 0.567 (p=0.010), whereas the hazard ratio of the high-GC33-exposed group to the low-GC33-exposed group was 0.467 (p=0.0009).
Figure 8F:
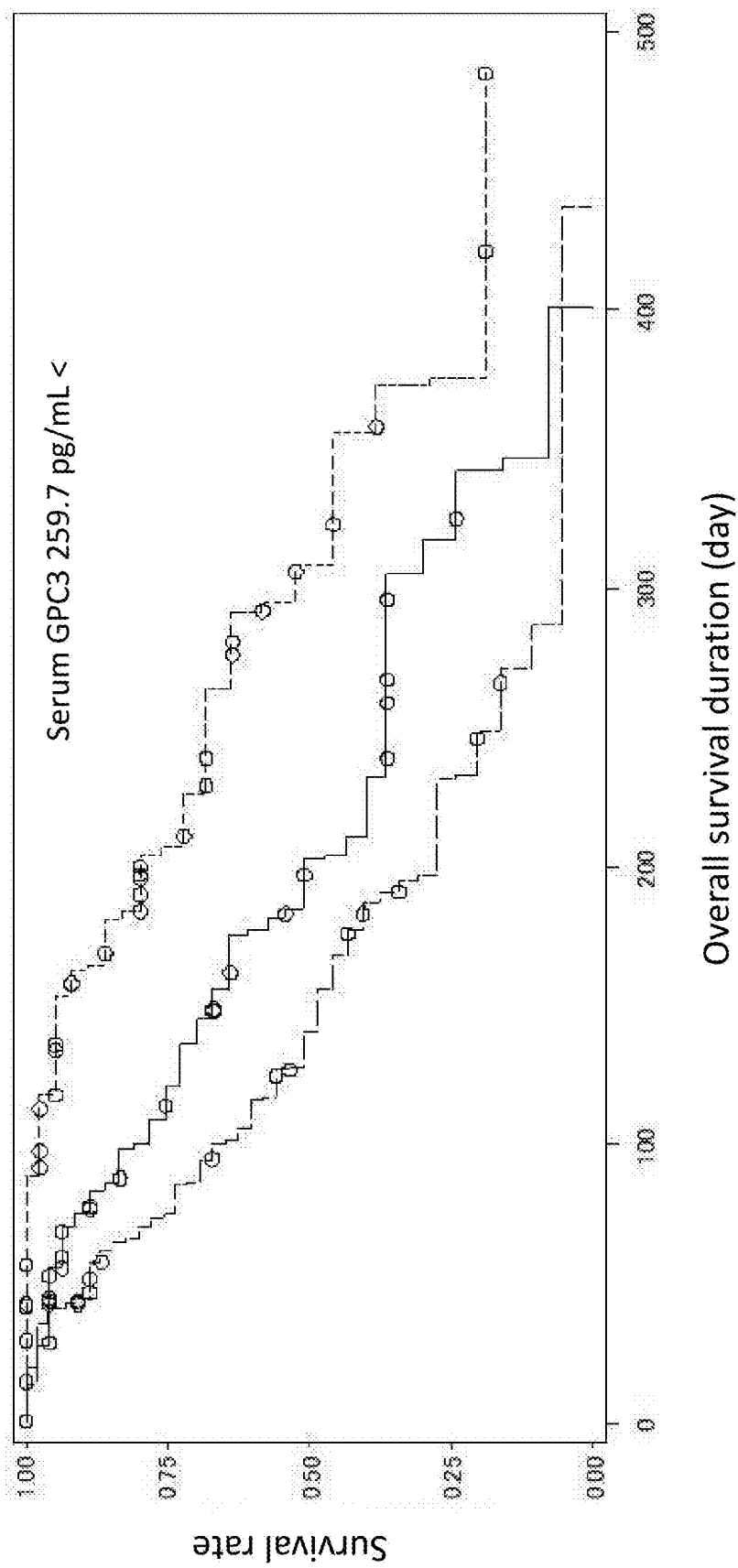
FIG. 8F is a diagram showing the correlation between the serum concentration of free GPC3 isolated from serum collected from patients before the start of GPC3-targeting drug therapy and the overall survival duration of the patients in a group with the serum concentration of free GPC3 higher than 259.7 pg/mL. The solid line represents the overall survival duration of a placebo group (50 cases). The broken line represents the overall survival duration of a low-GC33-exposed group (55 cases). The dotted line represents the overall survival duration of a high-GC33-exposed group (47 cases). The median value of the overall survival duration was 185 days for the placebo group, 156 days for the low-GC33-exposed group, and 308 days for the high-GC33-exposed group. The hazard ratio of the high-GC33-exposed group to the placebo group was 0.414 (p=0.0043), whereas the hazard ratio of the high-GC33-exposed group to the low-GC33-exposed group was 0.304 (p=<0.0001).

In the clinical trial, additional 7 cases (one of which was assessed as having an IHC total score of 6 as a result of final evaluation) were further registered as cases having an IHC total score of 7 or higher in GPC3-IHC on the basis of results of the staining method 1 and Child-Pugh score A. Their serum GPC3 levels were measured according to the method of Example 3. A total of 27 cases that received the administration of the GPC3-targeting drug were evaluated for their PFS in the same way as in Example 4. The relation of the serum GPC3 levels to PFS in these cases was studied using the logrank test. The test results showed that the PFS of a group having a measurable level of serum GPC3 before the administration (FIG. 6A) and the PFS of a group having a measurable level of serum GPC3 either before or after the administration (FIG. 6B) were both significantly longer than that of a group with a serum GPC3 level below the measurement limit.

Example 7

In order to confirm the efficacy and safety of GC33 in patients with advanced and/or recurrent hepatocellular cancer (HCC), a phase-II multicenter randomized double-blind placebo-controlled clinical trial which involved administering 1600 mg of GC33 every other week was carried out (NP27884 study), targeting adult patients with unrespectable advanced or metastatic hepatocellular cancer having a past history of treatment. These patients were randomized to a GC33 group (the fixed dose of 1600 mg was administered every other week after administration of two doses at a 1-week interval; n=121 cases) or a placebo group (n=60 cases) at a ratio of 2:1 and stratified to 3 cohorts on the basis of GPC3 expression levels (0, 1+, and 2+/3+) by IHC staining using GPC3-IHC kit (manufactured by Ventana Medical Systems, Inc.). Primary analysis was carried out at the time of occurrence of progression-free survival (PFS) events in 128 cases planned in the protocol.

The HCC patients subjected to the administration had histologically confirmed advanced or metastatic HCC (except for fibrolamellar type) unsuitable for curative therapy (surgical resection, liver transplantation, etc.) and/or local therapy or exacerbated after treatment and had a past history of treatment based on systemic therapy with at least one agent. Eligible patients were at least 18 years old with the capability of providing a tumor sample for GPC3 assay and exhibited Eastern Cooperative Oncology Group Performance Status of 0 or 1 and Child-Pugh class A. The patients also had at least one lesion that was evaluable according to the response evaluation criteria in solid tumors (RECIST). Appropriate hematopoietic functions (absolute neutrophil count ≥1500/μl, platelet ≥50000/μl, hemoglobin ≥8.0 g/dl), hepatic functions (total bilirubin ≤2 mg/dl, aspartate aminotransferase and alanine aminotransferase ≤5 times the upper limit of the normal level), and renal functions (serum creatinine≤twice the upper limit of the normal level) were evaluated as other criteria. Registrable female subjects were premenopausal female patients confirmed to be negative for a serum pregnancy test conducted within 10 days before the start of administration of the study drug, women without the possibility of pregnancy as a result of surgical contraception or after a lapse of 1 year or longer after menopause, and female patients other than the postmenopausal women (12-month or longer absence of menstruation) or the surgically contracepted women (resection of the ovary and/or the uterus), who consented to use two types of appropriate fertility control methods during clinical trial treatment and for at least 3 months or longer after the completion of administration of the study drug. Registrable male subjects were patients who consented to use fertility control based on the barrier method during clinical trial treatment and for at least 40 days after the completion of administration of the study drug. On the other hand, the registered subjects excluded patients who received major surgical operation within 2 weeks before the administration of the GPC3-targeting drug or did not get over severe disorder, patients confirmed to have brain or leptomeningeal metastasis, patients having a past history of malignant tumor within the last 5 years, patients having active infection requiring treatment except for hepatitis B or hepatitis C, patients having a past history of NCI-CTCAE v4.0 Grade 3 or higher hemorrhage within 4 weeks before the start of administration of the study drug, patients having a past history of organ transplantation including liver transplantation, patients who were scheduled to receive or were receiving the administration of an anticancer agent other than the agent to be administered in this test, patients who received the administration of an anticancer agent within 2 weeks before trial registration, patients who did not completely get over adverse reactions associated with the preceding locoregional or systemic therapy of hepatocellular cancer, patients under interferon therapy, patients who had baseline QTc exceeding 470 ms or exhibited baseline resting bradycardia (less than 45 beads/min.), patients who received the administration of an anticoagulant or a thrombolytic agent for therapeutic purposes within 2 weeks before the start of administration of the study drug (except for the administration of the agent at a low dose for the purpose of removing clogs in a catheter or for preventive purposes), pregnant or nursing patients, HIV-positive patients or patients having an AIDS-related disease, patients having a past history of hypersensitivity for similar agents (monoclonal antibodies, protein-containing preparations, and Chinese hamster ovary-derived preparations), and patients having a serious comorbidity judged by a principal investigator or a sub-investigator as being possibly worsened due to the study drug.

The protocol was carried out according to the guideline of the Good Clinical Practice (GCP) and approved by each participating ethical committee on clinical trials. All patients signed their names on written informed consent before registration. The patients received the continuous administration of GC33 unless the disease progressed or unacceptable toxicity appeared. Tumor was evaluated on the basis of a baseline and evaluated after 4 cycles, 7 cycles, and 10 cycles from the start of administration and then repetitively every four cycles until the disease progressed. Each cycle involved two weeks. The state of the disease was evaluated by principal investigators.

The expression of GPC3 proteins in HCC tumor tissues was evaluated by GPC3 immunohistochemical staining (GPC3-IHC). The central measurement of GPC3-IHC was carried out by Ventana Medical Systems, Inc. (USA). Unstained slides of HCC tumor tissues prepared from tumor blocks formalin-fixed and paraffin-embedded after excision by needle biopsy in each hospital were subjected to immunohistochemical staining. The antibody used was a mouse GC33 antibody.

Example 8

In the cases who received GC33 or a placebo in GPC3-targeting treatment, the serum concentration of free GPC3 was measured before the initial administration using a combination of two types of different antibodies capable of binding to free GPC3 (a combination of a GT30 antibody and a GT607 antibody or a combination of GT114 and GT165). GT30, GT607, GT114, and GT165 were prepared according to a method described in WO2004/022739 and selected as antibodies capable of binding to free GPC3. The H and L chains of GT30 are shown in SEQ ID NOs: 83 and 84, respectively. The H and L chains of GT607 are shown in SEQ ID NOs: 85 and 86, respectively. The H and L chains of GT114 are shown in SEQ ID NOs: 87 and 88, respectively. The H and L chains of GT165 are shown in SEQ ID NOs: 89 and 90, respectively.

An antibody-bound particle solution containing GT30 or GT114 bound to magnetic particle beads (manufactured by JSR Corp.) was added at a concentration of 25 µL/well to a 96-well microplate. Subsequently, a standard sample solution for a calibration curve (the GPC3 standard described in Example 3 was used) or an appropriately diluted serum sample was added thereto at a concentration of 25 µL/well, and further, alkaline phosphatase-labeled GT607 or GT165 was added thereto at a concentration of 25 µL/well. After shaking at 25° C. for 20 minutes, each well was washed 5 times with a washing solution, with the magnetic beads collected using Dyna-Mag-96 Side Skirted (manufactured by VERITAS Corp.). A luminescent substrate solution preheated to 37° C. was added thereto at a concentration of 50 µL/well. The plate was shaken at room temperature for 1 minute and then left standing for 4 minutes to emit light. Chemiluminescence intensity was measured using a luminometer (manufactured by VERITAS Corp.).

A calibration curve (standard curve) prepared on the basis of the standard sample containing the recombinant GPC3 was used to calculate the GPC3 antigen level in the serum of each patient from the obtained chemiluminescence intensity of each well.

Example 9

Once the PFS events of 128 cases were obtained from among 125 GC33-administered cases and 60 placebo-administered cases as described above, the effects of administration of GC33 in GPC3-targeting treatment were evaluated on the basis of PFS. In addition, overall survival (OS) was evaluated as a secondary endpoint when reaching 78 events.

The GC33-administered group was further divided into two groups (a group exposed to GC33 at a lower level than a cutoff value: low-GC33-exposed group, and a group exposed to GC33 at a higher level than a cutoff value: high-GC33-exposed group) using, as the cutoff value, the median value 230 µg/ml of projected blood trough levels of GC33 before administration of day 1 in the 3rd cycle (on the 4th week from the start of initial administration) based on population PK models obtained using the serum GC33 concentration values of this phase-II clinical trial. The progression-free survival duration or progression-free survival (PFS) or the overall survival duration or overall survival (OS) was compared as an index for clinical effects between these groups or between these groups and the placebo group by the Kaplan-Meier method.

Example 10

The serum concentrations of detected free GPC3 calculated in Example 8 were divided into two groups, i.e., a low-value group and a high-value group, on the basis of the median value of the concentrations measured in a system having GT30 and GT607 in combination. The PFS or OS curves of low-GC33-exposed, high-GC33-exposed, and placebo groups, as shown in Example 9, are shown in FIGS. 7A to 7D. Likewise, the serum concentrations of free GPC3 were divided into two groups on the basis of the median value of the concentrations measured in a system having GT114 and GT165 in combination. The PFS or OS curves of these groups are shown in FIGS. 8A to 8D.

In all cases, the group with a low concentration of free GPC3 exhibited the low effect of prolonging the PFS and OS durations, whereas the high-GC33-exposed group with a high concentration of free GPC3 in serum exhibited significantly low hazard ratios of the PFS and OS durations to the low-GC33-exposed group or the placebo group.

As a result of evaluating the cutoff value of free GPC3 that achieved the smallest significant difference, the cutoff value was 175 pg/mL for the GT30-GT607 system and 259.7 pg/mL for the GT114-GT165 system. The PFS and OS curves of a patient group that exhibited a free GPC3 level higher than the cutoff value in each system are shown in FIGS. 7E and 7F and FIGS. 8E and 8F, respectively. In this case as well, a significantly low hazard ratio, i.e., the prolongation of each survival duration, was exhibited in the high-GC33-exposed group.

All publications, patents, and patent applications cited herein are incorporated herein by reference in their entirety.

INDUSTRIAL APPLICABILITY

The present invention contributes to improvement in the efficacy of GPC3-targeting drug therapy and improvement in QOL of a patient to be treated, and is useful in the treatment of cancer including liver cancer.

[Free Text for Sequence Listing]
SEQ ID NO: 44: Modified antibody fragment
SEQ ID NO: 45: Modified antibody fragment
SEQ ID NO: 46: Modified antibody fragment
SEQ ID NO: 47: Modified antibody fragment
SEQ ID NO: 48: Modified antibody fragment
SEQ ID NO: 49: Modified antibody fragment
SEQ ID NO: 50: Modified antibody fragment
SEQ ID NO: 51: Modified antibody fragment
SEQ ID NO: 52: Modified antibody fragment
SEQ ID NO: 53: Modified antibody fragment
SEQ ID NO: 54: Modified antibody fragment
SEQ ID NO: 55: Modified antibody fragment
SEQ ID NO: 56: Modified antibody fragment
SEQ ID NO: 57: Modified antibody fragment
SEQ ID NO: 58: Modified antibody fragment
SEQ ID NO: 59: Modified antibody fragment
SEQ ID NO: 60: Modified antibody fragment
SEQ ID NO: 61: Modified antibody fragment
SEQ ID NO: 62: Modified antibody fragment
SEQ ID NO: 63: Modified antibody fragment
SEQ ID NO: 64: Modified antibody fragment
SEQ ID NO: 65: Modified antibody fragment
SEQ ID NO: 66: Modified antibody fragment
SEQ ID NO: 67: Modified antibody fragment
SEQ ID NO: 68: Modified antibody fragment
SEQ ID NO: 69: Modified antibody fragment
SEQ ID NO: 70: Modified antibody fragment
SEQ ID NO: 71: Modified antibody fragment
SEQ ID NO: 72: Modified antibody fragment
SEQ ID NO: 73: Modified antibody fragment

The invention claimed is:

1. A method for determining the efficacy of anti-GPC3 antibody therapy for liver cancer in a patient, or determining whether anti-GPC3 antibody therapy for a liver cancer patient should be continued, said method comprising measuring the concentration of free GPC3 in a biological sample isolated from the patient before the start of anti-GPC3 antibody therapy and/or the patient treated with the anti-GPC3 antibody therapy, wherein (1) when the concentration of free GPC3 is greater than a predetermined value, and/or (2) when the concentration of free GPC3 in a biological sample isolated from the patient treated with the anti-GPC3 antibody therapy is greater than that in a biological sample isolated before the start of the anti-GPC3 antibody therapy from the patient, it is determined that the anti-GPC3 antibody therapy is effective, or that the anti-GPC3 antibody therapy should be continued, and wherein the concentration of free GPC3 is measured using at least one antibody selected from the group consisting of (a)-(c):

(a) an antibody comprising a heavy-chain variable (VH) region having the same complementarity-determining regions (CDRs) as the VH region set forth in SEQ ID NO: 83, and further comprising a light-chain variable (VL) region having the same CDRs as the VL region set forth in SEQ ID NO: 84;

(b) an antibody comprising a VH region having the same CDRs as the VH region set forth in SEQ TD NO: 87, and further comprising a VL region having the same CDRs as the VL region set forth in SEQ ID NO: 88; and (c) an antibody comprising a VH region having the same CDRs as the VH region set forth in SEQ TD NO: 89, and further comprising a VL region having the same CDRs as the VL region set forth in SEQ ID NO: 90, wherein said predetermined value is a value selected from within the range of 0.1 ng/mL to 100 ng/mL.

2. The method according to claim 1, wherein the concentration of free GPC3 is a concentration in a whole blood sample, a plasma sample, or a serum sample isolated from the patient.

3. The method according to claim 2, wherein the concentration of free GPC3 in the biological sample isolated from the patient is a concentration in the plasma sample or the serum sample.

4. The method according to claim 1, wherein the concentration of free GPC3 is measured using an immunological method.

5. The method according to claim 1, wherein the patient shows high expression of GPC3 in an immunohistochemical staining score.

6. The method according to claim 1, further comprising administering said anti-GPC3 antibody therapy to the liver cancer patient determined to have an effective response to anti-GPC3 antibody therapy, or to the liver cancer patient for whom it was determined that the anti-GPC3 antibody therapy should be continued, wherein the anti-GPC3 antibody therapy is administered to achieve a blood trough level of 200 µg/ml or higher.

7. The method according to claim 1, wherein the antibody of said anti-GPC3 antibody therapy has antibody-dependent cellular cytotoxicity (ADCC) activity and/or complement-dependent cytotoxicity (CDC) activity.

8. The method according to claim 1, wherein the antibody of said anti-GPC3 antibody therapy is an anti-GPC3 chimeric antibody or a humanized antiGPC3 antibody comprising any of the following (1) to (5):

(1) heavy chain CDR1, heavy chain CDR2, and heavy chain CDR3 represented by SEQ ID NOs: 4, 5, and 6, respectively, and light chain CDR1, light chain CDR2, and light chain CDR3 represented by SEQ TD NOs: 7, 8, and 9, respectively;

(2) heavy chain CDR1, heavy chain CDR2, and heavy chain CDR3 represented by SEQ ID NOs: 12, 13, and 14, respectively, and light chain CDR1, light chain CDR2, and light chain CDR3 represented by SEQ ID NOs: 15, 16, and 17, respectively;

(3) heavy chain CDR1, heavy chain CDR2, and heavy chain CDR3 represented by SEQ ID NOs: 20, 21, and 22, respectively, and light chain CDR1, light chain CDR2, and light chain CDR3 represented by SEQ TD NOs: 23, 24, and 25, respectively;

(4) heavy chain CDR1, heavy chain CDR2, and heavy chain CDR3 represented by SEQ ID NOs: 28, 29, and 30, respectively, and light chain CDR1, light chain CDR2, and light chain CDR3 represented by SEQ ID NOs: 31, 32, and 33, respectively; and (5) heavy chain CDR1, heavy chain CDR2, and heavy chain CDR3 represented by SEQ ID NOs: 36, 37, and 38, respectively, and light chain CDR1, light chain CDR2, and light chain CDR3 represented by SEQ ID NOs: 39, 40, and 41, respectively.

9. The method according to claim 1, wherein the antibody of said anti-GPC3 antibody therapy comprises any of the following (1) to (6):

(1) a heavy chain variable region selected from the group of heavy chain variable regions represented by SEQ ID NOs: 44, 45, 46, 47, 48, 49, and 50 and a light chain variable region represented by SEQ ID NO: 51;

(2) a heavy chain variable region selected from the group of heavy chain variable regions represented by SEQ ID NOs: 44, 45, 46, 4 7, 48, 49, and 50 and a light chain variable region selected from the group of light chain variable regions represented by SEQ ID NOs: 52, 53, 54, 55, 56, 57, 58, 59, 60, 61, 62, 63, 64, 65, and 66;

(3) a heavy chain variable region represented by SEQ ID NO: 67 and a light chain variable region represented by SEQ ID NO: 68;

(4) a heavy chain variable region represented by SEQ ID NO: 69 and a light chain variable region represented by SEQ ID NO: 70;

(5) a heavy chain variable region represented by SEQ ID NO: 71 and a light chain variable region represented by SEQ ID NO: 72; and (6) a heavy chain variable region represented by SEQ TD NO: 71 and a light chain variable region represented by SEQ ID NO: 73.

10. The method according to claim 1, wherein the antibody of said anti-GPC3 antibody therapy comprises an anti-GPC3 antibody conjugated with a cytotoxic substance.

11. A method for administering an anti-GPC3 antibody therapy to a liver cancer patient selected for initial or continued treatment with an anti-GPC3 antibody therapy, said method comprising:

(a) a patient selection step selected from (1)-(3):

(1) detecting, in a biological sample, a concentration of free GPC3 that is greater than a predetermined value, wherein the biological sample is from a liver cancer patient that has not started anti-GPC3 antibody therapy; and selecting the liver cancer patient for initial treatment with an anti-GPC3 antibody therapy based on said detected concentration being greater than said predetermined value;
(2) detecting, in a biological sample, a concentration of free GPC3 that is greater than a predetermined value, wherein the biological sample is from a liver cancer patient treated with anti-GPC3 antibody therapy; and selecting the liver cancer patient for continued treatment with the anti-GPC3 antibody therapy based on said detected concentration being greater than said predetermined value; or
(3) detecting, in a biological sample from a liver cancer patient treated with anti-GPC3 antibody therapy, a concentration of free GPC3 that is greater than the concentration of free GPC3 in a biological sample isolated from the liver cancer patient before the start of the anti-GPC3 antibody therapy; and selecting the liver cancer patient for continued treatment with the anti-GPC3 antibody therapy based on said detected concentration being greater than the concentration of free GPC3 in the biological sample isolated from the liver cancer patient before the start of the anti-GPC3 antibody therapy; and
(b) administering the anti-GPC3 antibody therapy to the liver cancer patient selected in step (a);
wherein said predetermined value is a value selected from within the range of 0.1 ng/mL to 100 ng/mL.

12. The method according to claim 11, wherein the concentration of free GPC3 is a concentration in a whole blood sample, a plasma sample, or a serum sample isolated from the patient.

13. The method according to claim 12, wherein the concentration of free GPC3 in the biological sample isolated from the patient is a concentration in the plasma sample or the serum sample.

14. The method according to claim 11, wherein the concentration of free GPC3 is measured using an immunological method.

15. The method according to claim 11, wherein the patient shows high expression of GPC3 in an immunohistochemical staining score.

16. The method according to claim 11, wherein the anti-GPC3 antibody is administered in step (b) to achieve a blood trough level of 200 µg/ml or higher in the liver cancer patient.

17. The method according to claim 11, wherein the antibody of said anti-GPC3 antibody therapy has antibody-dependent cellular cytotoxicity (ADCC) activity and/or complement-dependent cytotoxicity (CDC) activity.

18. The method according to claim 11, wherein the antibody of said anti-GPC3 antibody therapy is an anti-GPC3 chimeric antibody or a humanized antiGPC3 antibody comprising any of the following (I) to (5):
(1) heavy chain CDR1, heavy chain CDR2, and heavy chain CDR3 represented by SEQ ID NOs: 4, 5, and 6, respectively, and light chain CDR1, light chain CDR2, and light chain CDR3 represented by SEQ ID NOs: 7, 8, and 9, respectively;
(2) heavy chain CDR1, heavy chain CDR2, and heavy chain CDR3 represented by SEQ ID NOs: 12, 13, and 14, respectively, and light chain CDR1, light chain CDR2, and light chain CDR3 represented by SEQ ID NOs: 15, 16, and 17, respectively;
(3) heavy chain CDR1, heavy chain CDR2, and heavy chain CDR3 represented by SEQ ID NOs: 20, 21, and 22, respectively, and light chain CDR1, light chain CDR2, and light chain CDR3 represented by SEQ ID NOs: 23, 24, and 25, respectively;
(4) heavy chain CDR1, heavy chain CDR2 and heavy chain CDR3 represented by SEQ 1D NOs: 28, 29, and 30, respectively, and light chain CDR1, light chain CDR2, and light chain CDR3 represented by SEQ ID NOs: 31, 32, and 33, respectively; and
(5) heavy chain CDR1, heavy chain CDR2, and heavy chain CDR3 represented by SEQ ID NOs: 36, 37, and 38, respectively, and light chain CDR1, light chain CDR2, and light chain CDR3 represented by SEQ ID NOs: 39, 40, and 41, respectively.

19. The method according to claim 11, wherein the antibody of said anti-GPC3 antibody therapy comprises any of the following (1) to (6):
(1) a heavy chain variable region selected from the group of heavy chain variable regions represented by SEQ ID NOs: 44, 45, 46, 47, 48, 49, and 50 and a light chain variable region represented by SEQ TD NO: 51;
(2) a heavy chain variable region selected from the group of heavy chain variable regions represented by SEQ ID NOs: 44, 45, 46, 47, 48, 49, and 50 and a light chain variable region selected from the group of light chain variable regions represented by SEQ ID NOs: 52, 53, 54, 55, 56, 57, 58, 59, 60, 61, 62, 63, 64, 65, and 66;
(3) a heavy chain variable region represented by SEQ ID NO: 67 and a light chain variable region represented by SEQ ID NO: 68;
(4) a heavy chain variable region represented by SEQ 10 NO: 69 and a light chain variable region represented by SEQ TD NO: 70;
(5) a heavy chain variable region represented by SEQ ID NO: 71 and a light chain variable region represented by SEQ ID NO: 72; and
(6) a heavy chain variable region represented by SEQ ID NO: 71 and a light chain variable region represented by SEQ ID NO: 73.

20. The method according to claim 11, wherein the antibody of said anti-GPC3 antibody therapy comprises an anti-GPC3 antibody conjugated with a cytotoxic substance.

21. The method according to claim 11, wherein said predetermined value is a value greater than 0.1 ng/mL, but less than 1 ng/mL.

* * * * *